(12) United States Patent
Perez et al.

(10) Patent No.: US 9,187,438 B2
(45) Date of Patent: Nov. 17, 2015

(54) DERIVATIVES OF BENZOTHIAZINES, PREPARATION THEREOF AND APPLICATION THEREOF AS DRUGS

(75) Inventors: Michel Perez, Castres (FR); Marie Lamothe, Castres (FR); Didier Junquero, Castres (FR); Yves Rival, Lagarrigue (FR)

(73) Assignee: PIERRE FABRE MEDICAMENT, Boulogne-Billancourt (FR)

( * ) Notice: Subject to any disclaimer, the term of this patent is extended or adjusted under 35 U.S.C. 154(b) by 145 days.

(21) Appl. No.: 13/254,473

(22) PCT Filed: Mar. 2, 2010

(86) PCT No.: PCT/EP2010/052609
§ 371 (c)(1),
(2), (4) Date: Sep. 2, 2011

(87) PCT Pub. No.: WO2010/100139
PCT Pub. Date: Sep. 10, 2010

(65) Prior Publication Data
US 2011/0319326 A1    Dec. 29, 2011

(30) Foreign Application Priority Data
Mar. 3, 2009  (FR) ...................................... 09 51336

(51) Int. Cl.
| *A61K 38/28* | (2006.01) |
| *A61P 5/50* | (2006.01) |
| *A61K 38/26* | (2006.01) |
| *A61P 3/10* | (2006.01) |
| *A61P 7/12* | (2006.01) |
| *C07K 14/605* | (2006.01) |
| *A61K 31/54* | (2006.01) |
| *C07D 279/16* | (2006.01) |
| *C07D 275/06* | (2006.01) |

(52) U.S. Cl.
CPC .................................... *C07D 275/06* (2013.01)

(58) Field of Classification Search
CPC .................................................. C07D 275/06
See application file for complete search history.

(56) References Cited

U.S. PATENT DOCUMENTS

2006/0160870 A1    7/2006  Majka et al.

FOREIGN PATENT DOCUMENTS

| CA | 2101350 A1 * | 1/1994 |
| DE | 1943265 A1 * | 8/1970 |
| JP | 2007-197369 A | 8/2007 |
| WO | WO 0230914 A1 * | 4/2002 |

OTHER PUBLICATIONS

Kim et al "Discovery of cyclicsulfonamide derivatives as 11B-hydroxysteroid dehydrogenase 1 inhibitors" Bioorgan Med Chem Lett 20:1065-1069, published online Dec. 11, 2009.*
Obach et al "In Vitro Metabolism and Covalent Binding of Enol-Carboxamide Derivatives and Anti-Inflammatory Agents Sudoxicam and Meloxicam: Insights into the Hepatotoxicity of Sudoxicam" Chem. Res. Toxicol. 21:1890-1899. Published online Aug. 16, 2008.*
Kim et al "Discovery of cyclicsulfonamide derivatives as 11 B-hydroxysteroid dehydrogenase 1 inhibitors" Bioorganic & Medicinal Chemistry Letters 20:1065-1069. Published online Dec. 11, 2009.*
Zinnes et al "1,2-Benzothiazines. 6. 3-Carbamoyl-4-hydroxy-2H-1,2-benzothiazine 1,1-Dioxides as Antiinflammatory Agents" J Med Chem 16:44-48. Published 1973.*
Vippagunta et al. "Crystalline Solids" Advanced Drug Delivery Reviews 48:3-26. Published 2001.*
Mayo Clinic Staff "Diseases and Conditions Type 2 diabetes" http://www.mayoclinic.org/diseases-conditions/type-2-diabetes/basics/prevention/con-20031902?p=1 . Jul. 24, 2014.*
Abe et al., "A new method for the preparation of secondary amines. VIII. Syntheses of phenylalkanolamines", Database CA [Online], Chemical Abstract Service, XP002534571, May 19, 1957, pp. 1-3.
Dallman et al., "Feast and Famine: Critical Role of Glucocorticoids with Insulin in Daily Energy Flow", Frontiers in Neuroendocrinology, vol. 14, No. 4, 1993, pp. 303-347.
Despres et al., "Abdominal obesity and metabolic syndrome", Nature, vol. 444, Dec. 14, 2006, pp. 881-887.
Duplomb et al., "Increased expression and activity of 11β-HSD-1 in diabetic islets and prevention with troglitazone", Biochemical and Biophysical Research Communications, vol. 313, 2004, pp. 594-599.
Edwards et al., "Localisation of 11β-Hydroxysteroid Dehydrogenase-Tissue Specific Protector of the Mineralocorticoid Receptor", The Lancet, Oct. 29, 1988, pp. 986-989.
Grundy et al., "Diagnosis and Management of the Metabolic Syndrome: An American Heart Association/National Heart, Lung, and Blood Institute Scientific Statement", Journal of the American Heart Association, vol. 112, Sep. 12, 2005, pp. 2735-2752.
Grundy, "Drug therapy of the metabolic syndrome: minimizing the emerging crisis in polypharmacy", Nature Reviews/Drug Discovery, vol. 5, Apr. 2006, pp. 295-309.

(Continued)

*Primary Examiner* — James H Alstrum Acevedo
*Assistant Examiner* — Zachary J Miknis
(74) *Attorney, Agent, or Firm* — Birch, Stewart, Kolasch & Birch, LLP

(57) ABSTRACT

The object of the present invention is benzothiazine derivatives having the capability of inhibiting 11β-HSD1 not only at an enzymatic level but also at a cell level. The compounds of the present invention are of general formula (I). Wherein notably $R_1$ represents a hydrogen or OR1 represents an ester or an ether. $R_2$ represents a naphthyl or a 1,2,3,4-tetrahydronaphthalene or a biphenyl or phenyl pyridine or a substituted phenyl. $R_3$ represents a methyl or ethyl; $R_4$ and $R'_4$ represent a hydrogen.

(I)

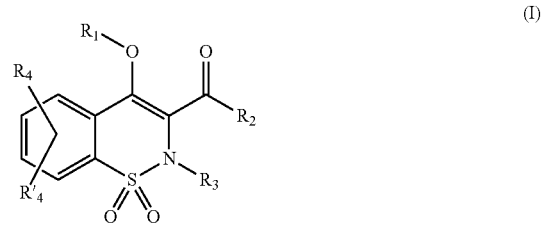

24 Claims, No Drawings

(56) References Cited

OTHER PUBLICATIONS

International Search Report dated May 11, 2010, for Application No. PCT/EP2010/052609.
Kotelevtsev et al., "11β-Hydroxysteroid dehydrogenase type 1 knockout mice show attenuated glucocorticoid-inducible responses and resist hyperglycemia on obesity or stress", Proc. Natl. Acad. Sci. USA, vol. 94, Dec. 1997, pp. 14924-14929.
Lazer et al., "Effect of Structural Modification of Enol-Carboxamide-Type Nonsteroidal Antiinflammatory Drugs on COX-2/COX-1 Selectivity". J. Med. Chem., vol. 40, 1997, XP-000974272, pp. 980-989.
Masuzaki et al., "A Transgenic Model of Visceral Obesity and the Metabolic Syndrome", Science, vol. 294, Dec. 7, 2001, pp. 2166-2170.
Mathis et al., "IP-one, a HTRF homogeneous assay to monitor functional activation of Gq coupled receptors in a HTS format", SBS, 12th Annual Conference, Seattle (USA), Sep. 2006, 1 page.
Monnier et al., "Type 2 diabetes: A well-characterised but suboptimally controlled disease. Can we bridge the divide?", Diabetes and Metabolism, vol. 34, 2008, pp. 207-216.
Mundt et al., "Development and Application of a Scintillation Proximity Assay (SPA) for Identification of Selective Inhibitors of 11β-Hydroxysteroid Dehydrogenase Type 1", ASSAY and Drug Development Technologies, vol. 3, No. 4, 2005, pp. 367-375.
Nathan et al., "Medical Management of Hyperglycemia in Type 2 Diabetes: A Consensus Algorithm for the Initiation and Adjustment of Therapy", Diabetes Care, vol. 32, No. 1, Jan. 2009, 193-203.
Pasquale et al., "Prospective Study of Type 2 Diabetes Mellitus and Risk of Primary Open-Angle Glaucoma in Women", Ophthalmology, vol. 113, No. 7, Jul. 2006, 1081-1086.
Reichard et al., "The Effect of Long-Term Intensified Insulin Treatment on the Development of Microvascular Complications of Diabetes Mellitus", The New England Journal of Medicine, vol. 329, No. 5, Jul. 29, 1993, pp. 304-309.

Solly et al., "High-Throughput Screening of 11β-Hydroxysteroid Dehydrogenase Type 1 in Scintillation Proximity Assay Format", Assay and Drug Developement Technologies, vol. 3, No. 4, 2005, pp. 377-384.
Strickler et al., "The Relation of Type 2 Diabetes and Cancer", Diabetes Technology and Therapeutics, vol. 3, No. 2, 2001, pp. 263-274.
Tokuda et al., "IC50 determination of Carberioxolene and Glycyrrhetinic acid on 11-beta hydroxysteroid dehydrogenase type 1 activity by HTRF", www.htrf-assays.com, Screentech, Mar. 2004, San Diego (USA), 1 page.
Wamil et al., "Inhibition of 11•-hydroxysteroid dehydrogenase type 1 as a promising therapeutic target", Drug Discovery Today, vol. 12, Nos. 13/14, Jul. 2007, pp. 504-520.
Wilcox et al., "Effects of Pioglitazone in Patents With Type 2 Diabetes With or Without Previous Stroke : Results From PROactive (PROspective pioglitAzone Clinical Trial in MacroVascular Events 04)", Journal of the American Heart Association, Stroke, vol. 38, Mar. 2007, pp. 865-873 (published online Feb. 2007).
Wilcox et al., "Effects of pioglitazone on major adverse cardiovascular events in high-risk patients with type 2 diabetes: Results from PROspective pioglitAzone Clinical Trial in macro Vascular Events (PROactive 10)", American Heart Journal, vol. 155, 2008, pp. 712-717.
Yoon et al., "Novel transition-metal catalyzed rearrangement of piroxicam, a benzothiazine carboxamide derivative", Database CA [Online], Chemical Abstracts Service, XP002534572, Accession No. 1991:607295, Jan. 1, 1990, pp. 1-2.
Zinnes et al., "1,2-Benzothiazines. 6.13-Carbamoyl-4-hydroxy-2H-1, 2-benzothiazine 1, 1-Dioxides as Antiinflammatory Agents", Journal of Medicinal Chemistry, vol. 16, No. 1, 1973, pp. 44-48.

* cited by examiner

DERIVATIVES OF BENZOTHIAZINES, PREPARATION THEREOF AND APPLICATION THEREOF AS DRUGS

The object of the present invention is derivatives of benzothiazine, the method for making them, the pharmaceutical compositions which contain them and their use as drugs intended for treating and/or preventing diabetes of type 2, obesity, dyslipidemias, arterial hypertension and atherosclerosis. These compounds may also find use in treating and/or preventing hyperglycemias, intolerance to glucose, insulin resistance, hypertriglyceridemias, hypercholesterolemias, restenoses, pancreatitises, retinopathies, nephropathies, neuropathies (Reichard et al., N. Engl. J. Med. 1993, 329:304-309), certain types of cancer (Strickler et al., Diabetes Technology & Therapeutics 2001, 3(2): 263-274) or glaucomas (Pascale et al., Ophtalmology 2006, 113(7): 1081-86).

The present invention also relates to the combinations between the described compounds and other agents used in the treatment of these pathologies. Indeed, the treatment of pathologies such as diabetes of type 2 often requires the combined use of several classes of compounds in order to attain the recommended values of glycemia and to keep it balanced (Nathan et al., Diabetes Care 2009 32:193-203). These associations may also relate to combined treatments of obesity and diabetes of type 2 (Grundy et al., Circulation 2005, 112: 2735-2752).

The metabolic syndrome is an early stage of several serious cardiovascular pathologies. It develops as a consequence of insulin-resistance and is characterized by visceral obesity (Després et al., Nature 2006 444(14): 881-87), associated with certain risk factors such as intolerance to glucose and certain dyslipidemias which may be associated with arterial hypertension (Grundy, Nat. Rev. Drug Discov. 2006, 5:295-309).

Diabetes of type 2 is a well-documented pathology since the glycemic disorders are explained by three main mechanisms: a deficiency of the function of the Langerhans β islets at the pancreas, a decrease in the use of glucose at the peripheral tissues and excess production of glucose by the liver (Monnier et al., Diabetes & Metabolism 2008, 34: 207-216). However, in spite of existing treatments, many patients affected with diabetes of type 2 do not reach the recommended glycemia target values (notably $HbA_{1c}$). Therefore, there is always a strong demand for treatments of this pathology based on new mechanisms.

Obesity is an ailment affecting an increasing number of persons worldwide. It is often associated with an increased risk of diabetes of type 2, of cardiovascular diseases, of cerebro-vascular strokes and of certain types of cancer. Obesity therefore represents a major risk factor for pathologies associated with a high level of morbidity or mortality.

Glucocorticoids (cortisol in humans, corticosterone in rodents) are ubiquitous hormones which play a predominant role in the regulation of energy metabolism. They promote gluconeogenesis and inhibit insulin secretion by beta pancreatic cells as well as peripheral recapture of glucose (Dallman et al., Front Neuroendocrinol. 1993, 14: 303-347).

It was recently demonstrated that 11β-hydroxysteroid dehydrogenases (11β-HSDs regulated the glucocorticoid levels in certain target tissues (liver, adipose tissue, kidney, brain . . . ). In humans, this mechanism may cause a local increase in cortisol. At the adipous tissue, this may lead to an increase in the visceral fatty mass due to the effect of glucocorticoids on the differentiation of pre-adipocytes into adipocytes and lipogenesis; in certain situations, glucocorticoids promote lipolysis and deleterious impacts of free plasma fatty acids at the liver, pancreas, skeletal muscle for example (lipotoxicity). At the liver, this generation of cortisol may cause an increase in glycemia which may develop into diabetes of type 2.

Two isoforms of 11β-HSD are known: type 1 and type 2. 11β-HSD2 is mainly localized in the kidneys. It catalyses the transformation of active glucocorticoids into inactive glucocorticoids (cortisol into cortisone in humans) and consequently it is essentially involved in the protection of the mineralocorticoid receptors (MR) towards activation by cortisol (Edwars et al., Lancet, 1988, 2: 986-989). Conversely, 11β-HSD1 predominantly acts like an 11-keto-reductase and transforms inactive glucocorticoids into active glucocorticoids in the tissues where it is strongly expressed (liver and adipous tissue). The inhibition of this enzyme at a hepatic and adipocyte level should therefore be expressed by a reduction of the effects mentioned earlier. Several studies conducted in animals have confirmed the implication of 11β-HSD1 in models of obesity and/or diabetes. Thus, the expression of 11β-HSD1 is increased in diabetic Zucker rats and this increase was correlated with the progression of the pathology (Duplomb et al., Biochem. Biophys. Res. Commun., 2004, 313: 594-599). Mice without any gene coding for 11β-HSD1 (KO mice) have proved to be resistant to hyperglycemia caused by obesity or stress (Kotelevtsev Y. et al. PNAS 1997, 94: 14924-14929). Conversely, transgenic mice selectively over-expressing 11β-HSD1 at the adipous tissue developed visceral obesity, insulin-resistant diabetes and hyperlipidemia (Masuzika et al., Science, 2001, 294: 2166-2170). These experimental data emphasize the inhibition advantage of 11β-HSD1 as a therapeutic target (Wamil et al., Drug Discovery Today, 2007, 12: 504-520)

The compounds of the present invention have the capability of selectively inhibiting 11β-HSD1 relatively to 11β-HSD2 which should be expressed in human by beneficial action on diabetes of type 2, obesity, hyperlipidemias, arterial hypertension, atherosclerosis and the whole of the pathologies which are associated therewith such as coronary strokes, cerebro-vascular strokes or arteritis of the lower limbs (Wilcox et al., Stroke, 2007, 38: 865-873; Wilcox et al., Am. Heart J. 2008, 155:712-7).

These compounds are distinguished from the prior art by their different chemical structure and their remarkable biological property.

The object of the present invention is benzothiazine derivatives having the capability of inhibiting 11β-HSD1 not only at an enzyme level but also at a cell level.

The compounds of the present invention are of the general formula (I):

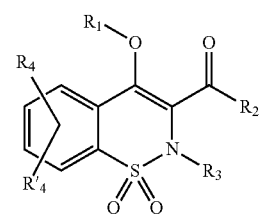

wherein:
$R_1$ represents:
  Hydrogen; $C_1$-$C_6$ alkyl; $COR_5$; $SO_2R_5$; $CO(CH_2)_mR_6$; $CO(CH_2)_mOR_6$; $(CH_2)_mR_6$; $(CH_2)_mCONR_7R_8$; $(CH_2)_nNR_7R_8$; $(CH_2)_nOR_6$; $CHR_7OR_9$; $(CH_2)_mR_{10}$
m represents:
  1 to 6
n represents:
  2 to 6

$R_2$ represents:

A phenyl substituted with one or more groups selected from a halogen, $C_1$-$C_6$ alkyl, CN, OH, $CF_3$, $OCF_3$, SMe, COMe, $CMe(OH)CF_3$, $CH(OH)CF_3$, $COOR_7$, $CONR_7R_{11}$; a naphthyl, 1,2,3,4-tetrahydro-naphthalene, biphenyl, phenyl pyridine or a heterocycle different from indole in the case where $R_1$, $R_4$ and $R'_4$ represent a hydrogen, either non-substituted or substituted with one or more groups selected from a halogen or $C_1$-$C_6$ alkyl, CN, OH, $CF_3$, $OCF_3$, OMe, SMe; a cycloalkyl either non-substituted or substituted with OH, $CONH_2$, $SO_2Me$, $SO_2NH_2$; a $C_1$-$C_6$ alkyl aryl or cycloalkyl aryl, Proviso:—the $R_2$ group is always bound to the carbonyl through a carbon atom.

When $R_2$ is a phenyl, the $COOR_7$ substituent is never in the position 4 relatively to the carbonyl.

$R_3$ represents:

Methyl or ethyl $R_4$ and $R'_4$, either identical or different, represent:

Hydrogen; halogen; $C_1$-$C_6$ alkyl; CN; $CF_3$; $OCF_3$; SMe; OMe; $NR_7R_8$; $SO_2Me$ $R_5$ represents:

$C_1$-$C_6$ alkyl; phenyl either non-substituted or substituted with one or more groups selected from a halogen, $C_1$-$C_6$ alkyl, CN, OH, $CF_3$, $OCF_3$, SMe; a naphthyl either non-substituted or substituted with one or more groups selected from halogen or $C_1$-$C_6$ alkyl, CN, OH, $CF_3$, $OCF_3$, SMe; a cycloalkyl either non-substituted or substituted with a $CONH_2$, $SO_2Me$, $SO_2NH_2$, heteroaryl either non-substituted or substituted with one or more groups selected from halogen, $C_1$-$C_6$ alkyl, CN, OH, $CF_3$, $OCF_3$, SMe $R_6$ represents:

Hydrogen; $C_1$-$C_6$ alkyl; phenyl either non-substituted or substituted with one or more groups selected from halogen, $C_1$-$C_6$ alkyl, CN, OH, $CF_3$, $OCF_3$, SMe; a naphthyl or heterocycle, either non-substituted or substituted with one or more groups selected from halogen or $C_1$-$C_6$ alkyl, CN, OH, $CF_3$, $OCF_3$, SMe; a cycloalkyl either non-substituted or substituted with $CONH_2$, $SO_2Me$, $SO_2NH_2$ $R_7$ represents:

Hydrogen, $C_1$-$C_6$ alkyl $R_8$ represents:

Hydrogen, $C_1$-$C_6$ alkyl, phenyl either non-substituted or substituted with one or more groups selected from halogen, $C_1$-$C_6$ alkyl, CN, OH, $CF_3$, $OCF_3$, SMe; a naphthyl or heterocycle, either non-substituted or substituted with one or more groups selected from halogen, $C_1$-$C_6$ alkyl, CN, OH, $CF_3$, $OCF_3$, SMe; a cycloalkyl either non-substituted or substituted with $CONH_2$, $SO_2Me$, $SO_2NH_2$ $R_7$ and $R_8$ taken together may form a cycle of 4-6 members with the nitrogen atom to which they are bound and which may contain one or more heteroatoms selected from N, S or O and may be either non-substituted or substituted with one or more groups selected from $C_1$-$C_6$ alkyl, $C_1$-$C_6$ alkyl aryl or aryl.

$R_9$ represents:

COOMe, COOEt $R_{10}$ represents:

Halogen, COOH, $COOR_7$ $R_{11}$ represents:

Hydrogen, $C_1$-$C_6$ alkyl, $C_1$-$C_6$ alkyl cycloalkyl, cycloalkyl, aryl, $C_1$-$C_6$ alkyl aryl as well as their stereoisomers, salts and solvates acceptable for therapeutic use.

In the foregoing definitions:

All the combinations of substituents or of variables are possible insofar that they lead to stable compounds.

The term « halogen » represents fluorine, chlorine, bromine or iodine.

The term « alkyl » represents saturated or unsaturated linear or branched, aliphatic hydrocarbon chains and comprising the specified number of carbon atoms.

The term « cycloalkyl » represents cyclic or polycyclic hydrocarbon chains comprising from 3-12 carbon atoms. As an example, mention may be made of adamantyl, cyclohexyl.

The term « aryl » represents any monocyclic or bicyclic carbon ring which may contain up to 7 atoms per ring and in which at least one of the rings is an aromatic ring. As an example, mention may be made of phenyl, biphenyl, naphthyl.

The term « heteroaryl » either represents a stable monocycle containing 5-7 atoms or a stable bicycle containing 8-11 atoms, unsaturated and consisting of carbon atoms and of one to four heteroatoms selected from N, O or S. As an example mention may be made of a furane, thiophene, pyridine, benzothiophene.

The term « heterocycle » either represents a stable monocycle containing from 5-7 atoms or a stable bicycle containing 8-11 atoms which may be either saturated or unsaturated, and consisting of carbon atoms and of one to four heteroatoms selected from N, O or S. Are also included in the bicycle definition, monocyclic heterocycles condensed with a benzene ring except for indole when in formula I, the radicals $R_1$, $R_4$ and $R'_4$ represent hydrogen. As an example, mention may be made of furane, pyrrole, thiophene, thiazole, isothiazole, oxadiazole, imidazole, oxazole, isoxazole, pyridine, pyrimidine, quinazoline, quinoline, quinoxaline, benzofurane, benzothiophene, indoline, indolizine, benzothiazole, benzothienyl, benzopyrane, benzoxazole, benzo[1,3]dioxole, benzoisoxazole, benzimidazole, chromane, chromene, dihydrobenzofurane, dihydrobenzothienyl, dihydroisoxazole, isoquinoline, dihydrobenzo[1,4]dioxin, imidazo[1,2-a]pyridine, furo[2,3-c]pyridine, 2,3-dihydro-1H-indene, [1,3]dioxolo[4,5-c]pyridine, pyrrolo[1,2-c]pyrimidine, pyrrolo[1,2-a]pyrimidine, tetrahydronaphthalene, benzo[b][1,4]oxazine.

By $OR_1$, being an ester or an ether, is meant in the sense of the present invention that $R_1$ represents: $C_1$-$C_6$ alkyl or $COR_5$ or $CO(CH_2)_mR_6$ or $CO(CH_2)_mOR_6$ or $(CH_2)_mR_6$ or $(CH_2)_mCONR_7R_8$ or $(CH_2)_nNR_7R_8$ or $(CH_2)_nOR_6$ or $CHR_7OR_9$ or $(CH_2)_nR_{10}$, as defined earlier.

The salts acceptable for therapeutic use of the compounds of the present invention comprise the conventional non-toxic salts of the compounds of the invention such as those formed from organic or inorganic acids or from organic or inorganic bases. As an example, mention may be made of the salts derived from inorganic acids such as hydrochloric, hydrobromic, phosphoric, sulfuric acids, and those derived from organic acids such as acetic, trifluoroacetic, propionic, succinic, fumaric, malic, tartaric, citric, ascorbic, maleic, glutamic, benzoic, salicylic, toluenesulfonic, methanesulfonic, stearic, lactic acids. As an example, mention may be made of the salts derived from inorganic bases such as soda, potash or calcium hydroxide and the salts derived from organic bases such as lysine or arginine.

These salts may be synthesized from the compounds of the invention containing a basic of acid portion and the corresponding acids or bases according to conventional chemical methods.

The solvates acceptable for therapeutic use of the compounds of the present invention comprise conventional solvates such as those formed during the last step of preparation of the compounds of the invention because of the presence of solvents. As an example, mention may be made of the solvates due to the presence of water or ethanol.

All the stereoisomers including all the optical isomers of the compounds of general formula (I) are also part of the present invention as well as their mixture in a racemic form.

According to a particular feature of the invention, the compounds of general formula (I) are those for which:

$R_2$ represents: A phenyl substituted with one or more groups selected from halogen, $C_1$-$C_6$ alkyl, CN, OH, $CF_3$, $OCF_3$, SMe; a naphthyl, 1,2,3,4-tetrahydro-naphthalene, biphenyl, or heterocycle different from indole in the case when $R_1$, $R_4$ and $R'_4$ represent a hydrogen atom, either non-substituted or substituted with one or more groups selected from a halogen or $C_1$-$C_6$ alkyl, CN, OH, $CF_3$, $OCF_3$, OMe, SMe; a cycloalkyl either non-substituted or substituted with $CONH_2$, $SO_2Me$, $SO_2NH_2$;

With the proviso: the group $R_2$ is always bound to the carbonyl through a carbon atom.

$R_4$ and $R'_4$, either identical or different, represent: hydrogen; halogen; $C_1$-$C_6$ alkyl; CN; $CF_3$; $OCF_3$; SMe; OMe; $NR_7R_8$;

$R_8$ represents:

A hydrogen, $C_1$-$C_6$ alkyl, a phenyl either non-substituted or substituted with one or more groups selected from a halogen, $C_1$-$C_6$ alkyl, CN, OH, $CF_3$, $OCF_3$, SMe; a naphthyl, or a heterocycle, either non-substituted or substituted with one or more groups selected from a halogen, $C_1$-$C_6$ alkyl, CN, OH, $CF_3$, $OCF_3$, SMe; a cycloalkyl either non-substituted or substituted with $CONH_2$, $SO_2Me$, $SO_2NH_2$ $R_7$ and $R_8$ taken together may form a ring with 4-6 members with the nitrogen atom to which they are bound and which may contain one or more heteroatoms selected from N, S or O and may either be non-substituted or substituted with one or more groups selected from a $C_1$-$C_6$ alkyl or aryl, with $R_1$ as defined earlier or as defined hereafter.

According to an embodiment of the invention, the compounds of general formula (I) are those for which $R_1$ represents a hydrogen.

According to another embodiment of the invention, the compounds of general formula (I) are those for which $OR_1$ represents an ester or an ether, with $R_1$ representing a $C_1$-$C_6$ alkyl or $COR_5$ or $CO(CH_2)_mR_6$ or $CO(CH_2)_mOR_6$ or $(CH_2)_mR_6$ or $(CH_2)_mCONR_7R_8$ or $(CH_2)_nNR_7R_8$ or $(CH_2)_nOR_6$ or $CHR_7OR_9$ or $(CH_2)_mR_{10}$.

According to a particular embodiment of the invention $OR_1$ represents an ester, with $R_1$ representing $COR_5$ or $CO(CH_2)_mR_6$ or $CO(CH_2)_mOR_6$.

The object of the present invention also relates to the compounds of general formula (I) for which $R_2$ represents a naphthyl or a 1,2,3,4-tetrahydro-naphthalene or biphenyl or a phenyl pyridine either non-substituted or substituted with one or more groups selected from a halogen, $C_1$-$C_6$ alkyl, CN, OH, $CF_3$, $OCF_3$, OMe, SMe; or a phenyl substituted with one or more halogens, CN, $CF_3$ or $C_1$-$C_6$ alkyl.

According to an embodiment of the invention, the compounds of general formula (I) are those for which $R_4$ and $R'_4$ represent a hydrogen.

Among the compounds of general formula (I) belonging to the present invention, an appreciated class of compounds corresponds to the compounds of general formula (I) wherein $R_1$ is a hydrogen and $R_2$ is a naphthyl or else a 1,2,3,4-tetrahydro-naphthalene.

Also, the present invention relates to the compounds of general formula (I) wherein $OR_1$ represents an ester or an ether and $R_2$ is a naphthyl or else a 1,2,3,4-tetrahydro-naphthalene.

Another appreciated class of compounds corresponds to the compounds of general formula (I) wherein $R_1$ is a hydrogen and $R_2$ is a phenyl substituted with one or more halogens, CN, $CF_3$ or $C_1$-$C_6$ alkyl.

Another appreciated class of compounds corresponds to the compounds of general formula (I) wherein $R_1$ is a hydrogen and $R_2$ is a biphenyl or a phenyl pyridine, either non-substituted or substituted as defined in the description of general formula (I).

Also, the present invention relates to the compounds of general formula (I) wherein $OR_1$ represents an ester or an ether and $R_2$ is a phenyl substituted with one or more halogen, CN, $CF_3$ or $C_1$-$C_6$ alkyl.

Another appreciated class of compounds corresponds to the compounds of general formula (I) wherein OR1 represents an ester or an ether and R2 is a biphenyl or a phenyl pyridine non-substituted or substituted as defined in the description of the general formula (I).

The present invention also relates to the preparation of the compounds of general formula (I) by general methods described in the following synthesis schemes if necessary completed with all the standard manipulations described in the literature or well-known to one skilled in the art or else still exemplified in the experimental part.

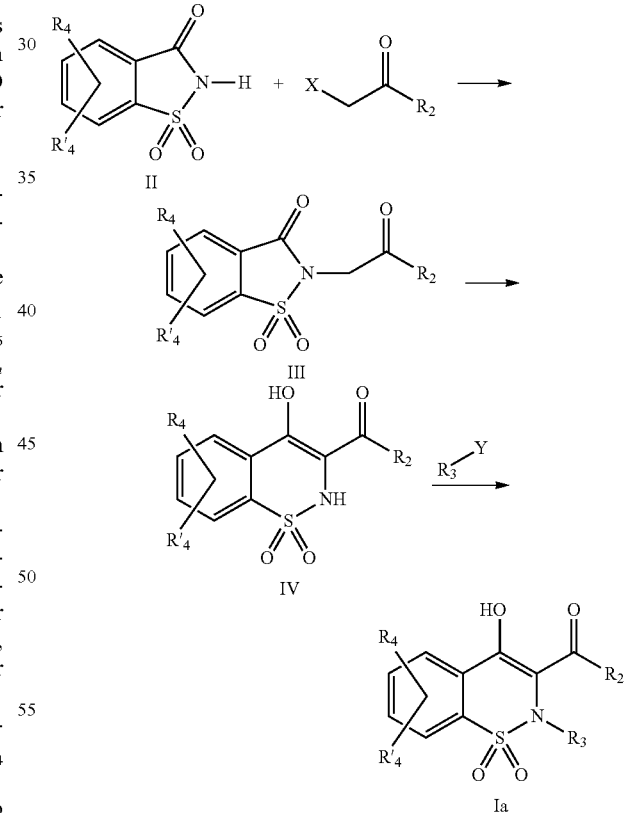

Scheme 1

Scheme 1 illustrates the first general method which may be used for preparing the compounds of general formula (Ia). In the general formulae above $R_2$, $R_3$, $R_4$ and $R'_4$, are defined as in the previous description of the general formula (I) and $R_1$ is equal to hydrogen. X may represent a leaving group such as for example Cl, Br, I, $OSO_2CH_3$, $OSO_2CF_3$ or O-tosyl. In this case, the reaction with the compound of general formula (II)

will be conducted in the presence of an inorganic base such as for example NaH in a polar anhydrous solvent such as THF or DMF at a temperature comprised between −20° and 100° C. The intermediate of general formula (III) is transformed into an intermediate of general formula (IV) by a rearrangement reaction in the presence of a base such as for example MeONa, EtONa in a polar anhydrous solvent such as MeOH or EtOH (possibly mixed with an a polar solvent such as toluene) at a temperature comprised between 25° and 100° C. The intermediate of general formula (IV) is transformed into a product of general formula (Ia) by reaction with $R_3Y$ wherein Y may represent a leaving group such as for example Cl, Br, I, $OSO_2CH_3$, $OSO_2CF_3$ or O-tosyl and $R_3$ is defined as earlier. In this case, the reaction with the compound of general formula (IV) will be conducted in the presence of an inorganic base such as for example NaH in a polar anhydrous solvent such as THF or DMF at a temperature comprised between −20° and 100° C.

Scheme 2 illustrates the general method which may be used for preparing the compounds of general formula (Ib). In the general formulae below, $R_1$, $R_2$, $R_3$, $R_4$ and $R'_4$, are defined as in the previous description of the general formula (I) except that $R_1$ is different from a hydrogen.

Scheme 2

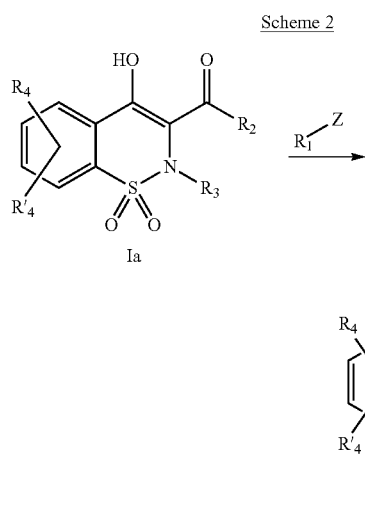

The intermediate of general formula (Ia) is transformed into a compound of general formula (Ib) by reaction with $R_1$—Z. When $R_1$ represents a $C_1$-$C_6$ alkyl, $(CH_2)_mR_6$, $(CH_2)_m CONR_7R_8$, $(CH_2)_nNR_7R_8$, $(CH_2)_nOR_6$, $CHR_7OR_9$ or $(CH_2)_mR_{10}$ with $R_6$, $R_7$, $R_8$, $R_9$, $R_{10}$, m and n defined as in the previous description of the general formula (I), except that $R_{10}$ does not represent an acid, and Z is a leaving group such as for example Cl, Br, I, $OSO_2CH_3$, $OSO_2CF_3$ or O-tosyl, the reaction with the enol of general formula (Ia) may be conducted in the presence of an organic or inorganic base such as for example $Et_3N$, $iPr_2NEt$, NaH, pyridine, $Cs_2CO_3$, $K_2CO_3$ in a polar anhydrous solvent such as THF, DMF, DMSO, acetone at a temperature comprised between −20° and 140° C., either in the presence or not of a salt as a catalyst and which may be KI, $Bu_4NI$, LiI, $AgBF_4$, $AgClO_4$, $Ag_2CO_3$, KF, $Bu_4NF$ or CsF. The reaction may also be conducted in a « sealed or threaded tube » heated by heat energy or microwave energy, at temperatures comprised between 80 and 180° C. Z may also represent an alcohol. In this case, the reaction with the intermediate (Ia) will be of the « Mitsunobu » type and may be conducted in the presence of diethylazodicarboxylate (DEAD) and of triphenylphosphine in a polar anhydrous solvent such as THF at a temperature comprised between 0 and 60° C. When $R_1$ represents $COR_5$, $SO_2R_5$ or $CO(CH_2)_mR_6$ with $R_5$, $R_6$ and m defined as in the previous description of the general formula (I) then Z may represent a chlorine. In this case, the reaction with the enol of general formula (Ia) boils down to the reaction between an acid chloride and a sulfonyl chloride and an alcohol. This reaction may be conducted in the presence of an organic or inorganic base such as for example $Et_3N$, $iPr_2NEt$, NaH, pyridine, $Cs_2CO_3$, $K_2CO_3$ in a polar anhydrous solvent such as THF, DMF, DMSO, dichloromethane at a temperature comprised between −20° and 140° C. When $R_1$ represents $COR_5$, $CO(CH_2)_mR_6$ or $CO(CH_2)_mOR_6$ with $R_5$, $R_6$ and m defined as in the previous description of the general formula (I) then Z may also represent a hydroxyl. In this case, the reaction with the enol of general formula (Ia) boils down to the reaction between an acid and an alcohol. This reaction may be conducted by methods and techniques well-known to one skilled in the art. A particularly appreciated method consists of producing this condensation in the presence of 1-(3-dimethylaminopropyl)-3-ethyl-carbodiimide (EDC), of 3-hydroxy-1,2,3-benzotriazin-4(3H)-one, of a tertiary amine such as diisopropylethylamine, in a polar aprotic solvent such as dichloromethane, at a temperature comprised between −15° C. and 40° C.

Scheme 3 illustrates the general method which may be used for preparing the compounds of general formula (Ic) wherein $R_1$ represents $(CH_2)_nNR_7R_8$ or $(CH_2)_nOR_6$ with $R_6$, $R_7$, $R_8$, n and $R_2$, $R_3$, $R_4$ and $R'_4$ defined as in the previous description of general formula (I). The intermediate of general formula (Ia) is transformed into an intermediate of general formula (V) by reaction with a reagent of general formula $X(CH_2)_nX'$ wherein X and X' represent a leaving group either identical or different such as for example Cl, Br, I, $OSO_2CH_3$, $OSO_2CF_3$ or O-tosyl and n is defined as earlier.

Scheme 3

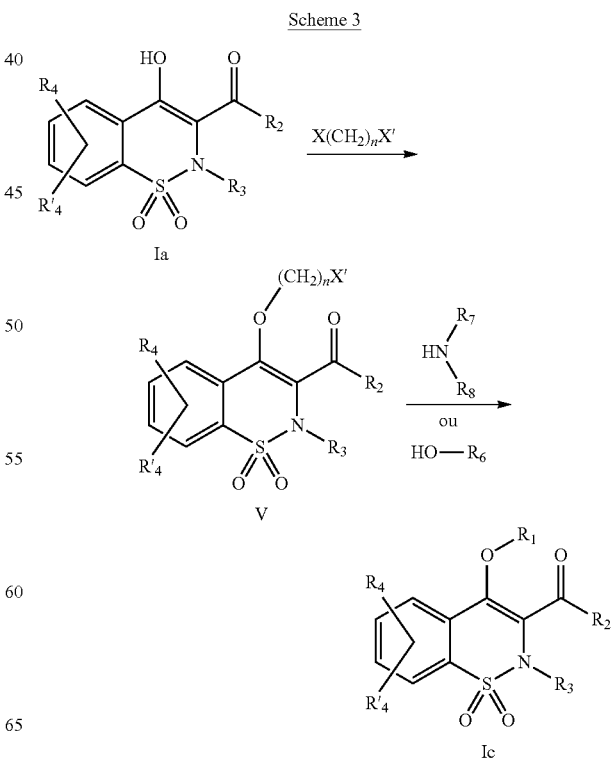

The reaction between this reagent and the enol of general formula (Ia) for leading to the intermediate of general formula (V) may be conducted in the presence of an organic or inorganic base such as for example $Et_3N$, $iPr_2NEt$, NaH, pyridine, $Cs_2CO_3$, $K_2CO_3$ in a polar anhydrous solvent such as THF, DMF, DMSO, acetone at a temperature comprised between $-20°$ and $140°$ C., either in the presence or not of a salt as a catalyst and which may be KI, $Bu_4NI$, LiI, $AgBF_4$, $AgClO_4$, $Ag_2CO_3$, KF, $Bu_4NF$ or CsF. This reaction may also be conducted without any solvent, with a large excess of reagent $X(CH_2)_nX'$. The reaction may also be conducted in a « sealed or threaded tube» heated by heat energy or microwave energy, at temperatures comprised between 80 and 180° C. X or X' may also represent an alcohol. In this case, the reaction with the intermediate (V) will be of the « Mitsunobu» type and may be conducted in the presence of diethylazodicarboxylate (DEAD) and of triphenylphosphine in a polar anhydrous solvent such as THF at a temperature comprised between 0 and 60° C.

The intermediate of general formula (V) is transformed into a product of general formula (Ic) by reaction with $HNR_7R_8$ or $HOR_6$ wherein $R_6$, $R_7$ and $R_8$ are defined as in the previous description of the general formula (I). This reaction may be conducted in the presence of an organic or inorganic base such as for example $Et_3N$, $iPr_2NEt$, NaH, pyridine, $Cs_2CO_3$, $K_2CO_3$ in a polar anhydrous solvent such as THF, DMF, DMSO, acetone at a temperature comprised between $-20°$ and $140°$ C., either in the presence or not of a solvent as a catalyst and which may be KI, $Bu_4NI$, LiI, $AgBF_4$, $AgClO_4$, $Ag_2CO_3$, KF, $Bu_4NF$ or CsF. The selection of the experimental conditions and of the reagents for conducting this reaction of course depends on the nature of the substituents $R_6$, $R_7$ and $R_8$ and will be performed according to the methods and techniques well-known to one skilled in the art.

Scheme 4 illustrates the general method which may be used for preparing the compounds of general formula (Id) wherein $R_1$ represents $(CH_2)_mCONR_7R_8$ with $R_7$, $R_8$, m and $R_2$, $R_3$, $R_4$ and $R'_4$, defined as in the previous description of general formula (I).

Scheme 4

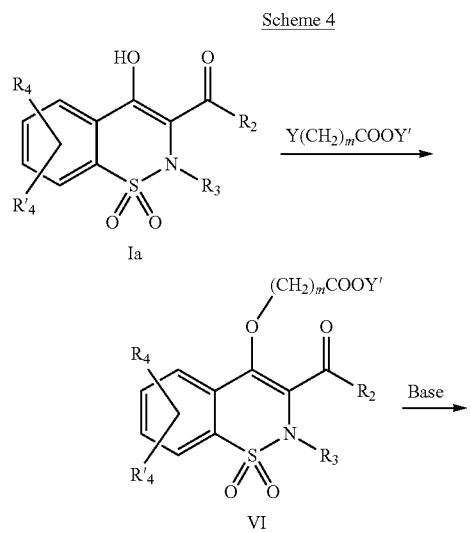

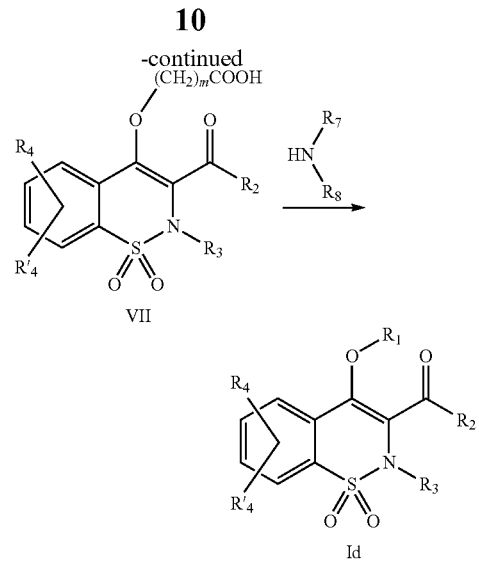

The intermediate of general formula (Ia) is transformed into an intermediate of general formula (VI) by reaction with a reagent of general formula $Y(CH_2)_mCOOY'$ wherein Y represents a leaving group such as for example Cl, Br, I, $OSO_2CH_3$, $OSO_2CF_3$ or O-tosyl, m is defined as earlier and Y' represents a $C_1$-$C_4$ alkyl radical. This reaction may be conducted in the presence of an organic or inorganic base such as for example $Et_3N$, $iPr_2NEt$, NaH, pyridine, $Cs_2CO_3$, $K_2CO_3$ in a polar anhydrous solvent such as THF, DMF, DMSO, acetone at a temperature comprised between $-20°$ and $140°$ C., either in the presence or not of a salt as a catalyst and which may be KI, $Bu_4NI$, LiI, $AgBF_4$, $AgClO_4$, $Ag_2CO_3$, KF, $Bu_4NF$ or CsF. The reaction may also be conducted in a « sealed or threaded tube» heated by heat energy or microwave energy, to temperatures comprised between 80 and 180° C. The intermediate of general formula (VI) is transformed into an intermediate of general formula (VII) by reaction with an inorganic base such as for example NaOH, KOH, LiOH in a polar solvent such as methanol, ethanol, THF and water, at a temperature comprised between 20° and 80° C. The obtained carboxylic acid (VII) may react with an amine in order to lead to the compounds of general formula (Id). This reaction may be conducted by the methods and techniques well-known to one skilled in the art. A particularly appreciated method consists of condensing these 2 entities in the presence of 1-(3-dimethylaminopropyl)-3-ethyl-carbodiimide (EDC), of 3-hydroxy-1,2,3-benzotriazin-4(3H)-one, of a tertiary amine such as diisopropylethylamine, in a polar aprotic solvent such as dichloromethane or DMF, at a temperature comprised between $-15°$ C. and 50° C. Or further, as an example, by using benzotriazol-1-yloxy-tris(dimethylamino) phosphonium hexafluorophosphate (BOP) in the presence of 1-hydroxybenzotriazole, of a tertiary amine such as diisopropylethylamine, in a polar solvent such as DMF, $CH_2Cl_2$ or DMSO at a temperature comprised between 10° and 50° C. Another particularly appreciated method consists of transforming the carboxylic acid into an acid chloride by reaction with oxalyl chloride or thionyl chloride in the absence or in the presence of a base such as pyridine or triethylamine with or without a solvent such as toluene or dichloromethane at a temperature comprised between 20 and 100° C. This acid chloride may then react with the amine $HNR_7R_8$ in the presence of a base such as pyridine or triethylamine in a solvent such as dichloromethane at a temperature comprised between 0 and 100° C.

Scheme 5 illustrates the general method which may be used for transforming the compounds of general formula (Ie) wherein $R_4$ represents a fluorine and $R_2$, $R_3$ and $R'_4$ are defined as in the previous description of the general formula (I) into compounds of general formula (If) wherein $R_4$ represents $NR_7R_8$ with $R_7$, $R_8$ and $R_2$, $R_3$ and $R'_4$ defined as in the previous description of the general formula (I).

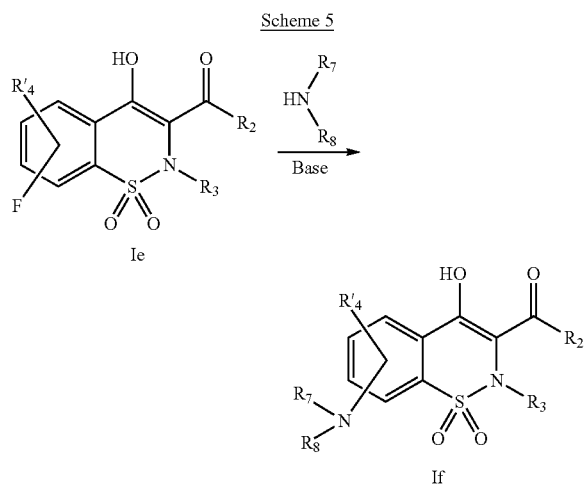

The compounds of general formula (Ie) may be transformed into compounds of general formula (If) by reaction with an amine of general formula $HNR_7R_8$ in the presence of an organic or inorganic base such as for example $Et_3N$, $iPr_2NEt$, NaH, $Cs_2CO_3$, $K_2CO_3$ in a polar anhydrous solvent such a DMF, DMSO at a temperature comprised between 20° and 140° C.

Scheme 6 illustrates the general method which may be used for transforming the compounds of general formula (Ig) wherein $R_3$, $R_4$ and $R'_4$ are defined as in the previous description of the general formula (I) and wherein $R_2$ represents a phenyl substituted with a group X representing a bromine, chlorine or an OTf, into compounds of general formula (Ih) where $R_2$ represents a biphenyl or a phenyl pyridine either substituted or not and wherein $R_3$, $R_4$ and $R'_4$ are defined as in the previous description of the general formula (I).

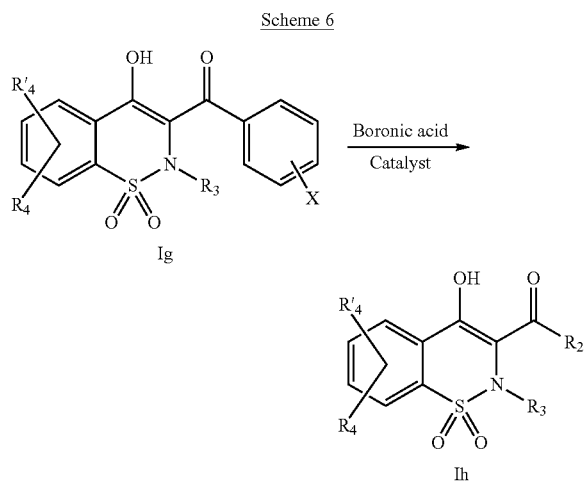

The compounds of general formula (Ig) may be transformed into compounds of general formula (Ih) by a Suzuki type reaction with a boronic acid in the presence of an organic or inorganic base such as for example $Et_3N$, NMP, $iPr_2NEt$, NaH, $Cs_2CO_3$, $K_2CO_3$, $K_3PO_4$ with a catalyst such as for example palladium acetate, palladium tetrakis triphenylphosphine, tris(dibenzilideneacetone)dipalladium in a polar solvent such as for example acetone, methyl ethyl ketone, ethanol, DME, water, dioxane, and optionally in the presence of a phosphine such as triphenylphosphine or tricyclohexylphosphine at a temperature comprised between 20° and 140° C.

Scheme 7 illustrates the general method which may be used for transforming the compounds of general formula (II) wherein $R_3$, $R_4$ and $R'_4$ are defined as in the previous description of general formula (I) and wherein $R_2$ represents a phenyl substituted with a CN group in the ortho or meta position into compounds of general formula (Ij) wherein $R_2$ represents a phenyl substituted with a carboxylic acid in the ortho or meta position and then into compounds of general formula (Ik) wherein $R_2$ represents a phenyl substituted with an amide of formula $CONR_7R_{11}$ and wherein $R_3$, $R_4$, $R_7$, $R_{11}$ and $R'_4$ are defined as in the previous description of the general formula (I).

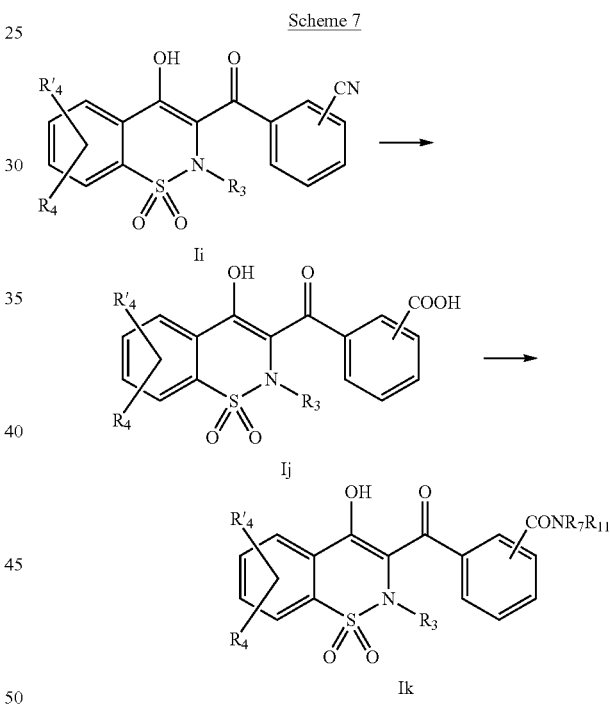

The compounds of general formula (II) may be transformed into compounds of general formula (Ij) by treatment with an inorganic base such as for example NaOH, KOH, LiOH in a polar solvent such as ethanol, methanol, THF, water at a temperature comprised between 20° and 140° C. followed by acidification by treatment with an acid such as HCl, $H_2SO_4$, HCOOH. The compounds of general formula (Ij) may be transformed into compounds of general formula (Ik) by reaction with an amine of formula $HNR_7R_{11}$. This reaction may be conducted with methods and techniques well-known to one skilled in the art. A particularly appreciated method consists of condensing these 2 entities in the presence of 1-(3-dimethylaminopropyl)-3-ethyl-carbodiimide (EDC), of 3-hydroxy-1,2,3-benzotriazin-4(3H)-one, of a tertiary amine such as diisopropylethylamine, in a polar aprotic solvent such as dichloromethane or DMF, at a temperature comprised between −15° C. and 50° C. Or further, as an example, by using benzotriazol-1-yloxy-tris(dimethylamino)phosphonium hexafluorophosphate (BOP) in the presence of 1-hydroxybenzotriazole, of a tertiary amine such as diisopropylethylamine, in a polar solvent such as DMF, $CH_2Cl_2$ or DMSO at a temperature comprised between 10° and 50° C. Another particularly appreciated method consists of transforming the carboxylic acid into an acid chloride by reaction with oxalyl chloride or thionyl chloride in the absence or in the presence of a base such as pyridine or triethylamine with or without a solvent such as toluene or dichloromethane at a temperature comprised between 20 and 100° C. This acid chloride may then react with the amine $HNR_7R_{11}$ in the presence of a base such as pyridine or triethylamine in a solvent such as dichloromethane at a temperature comprised between 0 and 100° C.

When it is desired to isolate a compound of general formula (I) containing at least one acid or basic function in the salt state by addition with a base or an acid, this may be achieved by treating the free base or acid of general formula (I) (wherein at least one acid or basic function exists) with a suitable base or acid, preferably in an equivalent amount.

The examples which follow illustrate the invention without however limiting the scope thereof.

Note: for the whole of the following compounds (except if mention otherwise) the HPLC purities were determined under the following conditions:
Column Waters XTerra MS $C_{18}$, 4.6×50 mm, 5 μm, λ=220 nm, Gradient 100% $H_2O$ (+0.05% TFA) at 100% $CH_3CN$ (+0.05% TFA) in 6 minutes, and then 1 minute at 100% $CH_3CN$ (+0.05% TFA). Pump Waters 600E, flow rate of 3 ml/min.

EXAMPLE 1

(4-Hydroxy-2-methyl-1,1-dioxo-2H-benzo[e][1,2]thiazin-3-yl)(naphthalen-2-yl)methanone

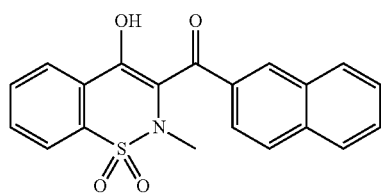 [SMILES: CN1C(C(=O)c2ccc3ccccc3c2)=C(O)c2ccccc2S1(=O)=O]

EXAMPLE 1A 2-(2-(naphthalen-2-yl)-2-oxoethyl)benzo[d]isothiazol-3(2H)-one-1,1-dioxide The saccharin (25 g, 136 mmol) and DMF (350 mL) are introduced into a three-neck flask equipped with a thermometer and a condenser. The medium is inertized by a vacuum/nitrogen succession (3×). Sodium hydride (6 g, 150 mmol) is slowly added, followed by 2-bromo-1-(naphthalen-2-yl)ethanone (37.4 g, 150 mmol). The reaction medium is heated to 65° C. for 4 hours, and then cooled to room temperature. The formed precipitate is filtered, rinsed with water and dried until constant weight for obtained 37 g of the product 1A as a pale being solid (HPLC: RT=4.97 min, 100%). A second product batch is obtained by adding water into the filtrate. The formed precipitate is filtered, rinsed with water and then with a minimum of ethyl in order to obtain after drying, 10 g of product (HPLC: RT=4.97 min, 93%). The global yield of this reaction is 96%.

$^1$H NMR, dmso-$d_6$, δ (ppm): 5.62 (s, 2H); 7.68 (t, 1H); 7.73 (t, 1H); 8.00-8.25 (m, 7H); 8.39 (d, 1H); 8.92 (s, 1H).

Mass spectrum (ESI+): m/z 352 (MH$^+$, 100%); 369 (MNH$_4^+$, 24%).

EXAMPLE 1B (4-hydroxy-1,1-dioxo-2H-benzo[e][1,2]thiazin-3-yl)(naphthalen-2-yl)methanone In a two-neck flask equipped with a condenser and under an inert atmosphere, ethanol (165 mL) is introduced followed by slow addition of sodium cut into thin slices and rinsed with heptane (8 g, 347 mmol). At the end of the addition, the reaction medium is heated to 70° C. until complete reaction of the sodium. The reaction is then cooled to room temperature, and the compound 1A (47 g, 131 mmol) is added rapidly. An intense vermilion red and then blood red coloration appears as well as a thick precipitate. The reaction medium is heated briefly to 60° C. where it solidifies. It is then cooled to room temperature and diluted in 500 mL of ethyl acetate. A 1N HCl aqueous solution is then added until a canary yellow suspension is obtained. The precipitate is filtered, rinsed with water and a minimum of a 50/50 water/EtOH mixture. It is then dried in vacuo until it has constant weight in order to obtain the product 1B as a canary yellow solid (40.9 g; 88%). HPLC: RT=5.15 min, 100%.

$^1$H NMR, dmso-$d_6$, δ (ppm): 7.66 (t, 1H); 7.72 (t, 1H); 7.95 (broad s, 3H); 8.05 (d, 2H); 8.11 (broad s, 2H); 8.22 (broad s, 1H); 8.64 (s, 1H); 9.99 (s, 1H); 15.59 (s, 1H).

Mass spectrum (ESI+): m/z 352 (MH$^+$, 100%); 369 (MNH$_4^+$, 31%).

EXAMPLE 1

(1,1-dioxo-4-hydroxy-2-methyl-2H-benzo[e][1,2]thiazin-3-yl)(naphthalen-2-yl)methanone In a two-neck flask under an inert atmosphere, the compound 1B (40.9 g, 116 mmol) is dissolved in DMF (409 mL). NaH (6.05 g, 151 mmol) is added. This reaction is slightly exothermic and the reaction medium assumes an intense blood red coloration. Methane iodide (10.8 mL, 174 mmol) is added and the reaction medium is stirred at room temperature for 2 hours. Water (10 mL) is added and the reaction medium is concentrated. The residue is taken up in ethyl acetate and the precipitate is filtered, washed with water and with a minimum of ethyl acetate (solid 1). The filtrate is washed twice with an aqueous solution half-saturated with NaCl, and then concentrated until half of the volume is obtained and filtered. The precipitate (solid 2) is rinsed with a minimum of 50/50 EtOAc/Et$_2$O. The filtrate is concentrated. The residue is filtered on silica (eluent: 50/50 heptane/CH$_2$Cl$_2$, and then 25/75 heptane/CH$_2$Cl$_2$), in order to obtain after evaporation of the solvents, a yellow powder (solid 3). The 3 solids are collected in order to obtain the product 1 as a canary yellow solid (40.1 g; 89%) HPLC: RT=5.65 min, 99%

$^1$H NMR, dmso-$d_6$, δ (ppm): 2.65 (s, 3H); 7.66 (t, 1H); 7.72 (t, 1H); 8.00 (broad s, 3H); 8.02 (d, 1H); 8.12 (broad s, 3H); 8.22 (broad s, 1H); 8.67 (s, 1H).

Mass spectrum (ESI+): m/z 366 (MH$^+$, 100%).

Preparation of the Sodium Salt of 4-hydroxy-2-methyl-1,1-dioxo-2H-benzo[e][1,2]-thiazin-3-yl)(naphthalen-2-yl)methanone A fraction of the compound 1 is dissolved and methanol and treated at room temperature with 1.05 equivalents of an aqueous 1N soda solution. The reaction medium is concentrated and the solid residue rinsed with a mixture of dichloromethane and ethyl ether. The thereby obtained canary yellow solid is dried in vacuo for several days.

HPLC: RT=11.73 min, 99.71% (column: XBridge C8, 5 µM, 4.6×250 mm (Waters); eluent: $CH_3CN/H_2O/KH_2PO_4$ 600/400/6.8 g, pH4, 25° C.; 1 mL/min; 220 nm)

$^1$H NMR, dmso-$d_6$, δ (ppm): 2.61 (s, 3H); 7.50 (broad s, 2H); 7.62 (broad s, 2H); 7.65-7.72 (m, 2H); 7.80 (d, 1H); 7.89 (broad s, 2H); 7.93-7.98 (m, 2H).

Mass spectrum (ESI+): m/z 366 ($MH^+$, 100%).

EXAMPLES 2 TO 12

The compounds 2 to 12 were synthesized according to the procedure used for preparing the derivative 1, from saccharin and various 2-bromo-1-(alkyl or aryl)ethanones in the first step and from methyl iodide or ethyl iodide in the third step. The rearrangement protocol in the second step is unchanged.

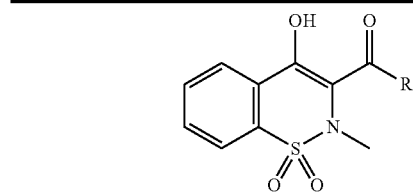

| Ex.** | R | Name of the compounds | HPLC | Yld. (3 steps) | Mass $MH^+$ |
|---|---|---|---|---|---|
| 2 | adamantan-1-yl | (4-hydroxy-2-methyl-2H-1,1-dioxo-benzo[e][1,2]thiazin-3-yl) (adamantan-1-yl)methanone | 6.11' 98.9% | 30% | 374 |
| 3 | 4-methyl-phenyl | (4-hydroxy-2-methyl-2H-1,1-dioxo-benzo[e][1,2]thiazin-3-yl) (4-methylphenyl)methanone | 5.33' 99% | 49% | 330 |
| 4 | 4-chloro-phenyl | (4-hydroxy-2-methyl-2H-1,1-dioxo-benzo[e][1,2]thiazin-3-yl) (4-chlorophenyl)methanone | 5.43' 99% | 38% | 350 |
| 5 | 4-cyano-phenyl | (4-hydroxy-2-methyl-2H-1,1-dioxo-benzo[e][1,2]thiazin-3-yl) (4-cyanophenyl)methanone | 4.97' 99% | 82% | 339* |
| 6 | biphenyl-4-yl | biphenyl-4-yl-(4-hydroxy-2-methyl-1,1-dioxo-2H-benzo[e][1,2]thiazin-3-yl)methanone | 5.86' 98% | 57% | 392 |
| 7 | 2,4-dichloro-phenyl | (4-hydroxy-2-methyl-1,1-dioxo-2H-benzo[e][1,2]thiazin-3-yl) (2,4-dichlorophenyl)methanone | 5.52' 98% | 14% | 384 |

* negative ESI (M – H).
** $^1$H NMR, dmso-$d_6$, Ex. 2: 1.72 (broad s, 6 H); 2.05 (broad s, 3 H); 2.10 (broad s, 6 H); 2.83 (s, 3 H); 7.91 (broad s, 3 H); 8.10 (t, 1 H); 16.1 (s, 1 H). Ex. 5: 2.63 (s, 3 H); 7.99 (s, 3 H); 8.11 (s, 4 H); 8.19 (broad s, 1 H); 14.5-15.5 (m, 1 H, exch). Ex. 6: 2.70 (s, 3 H); 7.46 (t, 1 H); 7.54 (t, 2 H); 7.82 (d, 2 H); 7.95-8.00 (m, 5 H); 8.18-8.23 (m, 3 H); 15.65 (broad s, 1 H, exch). Ex. 7: 2.67 (s, 3 H); 7.54-7.64 (m, 2 H); 7.83 (s, 1 H); 7.93 (broad s, 3 H); 8.11 (broad s, 1 H); 13.5-14.5 (broad s, 1 H).

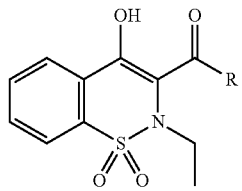

| Ex. * | R | Name of the compounds | HPLC | Yld. (3 steps) | Mass $(M + H)^+$ |
|---|---|---|---|---|---|
| 8 | adamantan-1-yl | (4-hydroxy-2-ethyl-1,1-dioxo-2H-benzo[e][1,2]thiazin-3-yl) (adamantan-1-yl)methanone | 6.24' 99% | 32% | 388 |
| 9 | naphthalen-2-yl | (4-hydroxy-2-ethyl-1,1-dioxo-2H-benzo[e][1,2]thiazin-3-yl) (naphthalen-2-yl)methanone | 5.72' 99% | 55% | 380 |
| 10 | 4-methyl-phenyl | (4-hydroxy-2-ethyl-1,1-dioxo-2H-benzo[e][1,2]thiazin-3-yl) (4-methylphenyl)methanone | 5.49' 99% | 40% | 344 |
| 11 | 4-chloro-phenyl | (4-hydroxy-2-ethyl-1,1-dioxo-2H-benzo[e][1,2]thiazin-3-yl) (4-chlorophenyl)methanone | 5.58' 99% | 35% | 364 |
| 12 | biphenyl-4-yl | biphenyl-4-yl-(4-hydroxy-2-ethyl-1,1-dioxo-2H-benzo[e][1,2]thiazin-3-yl)methanone | 6.06' 99% | 61% | 406 |

* $^1$H NMR, dmso-$d_6$, Ex. 8: 0.68 (t, 3 H); 1.71 (broad s, 6 H); 2.05 (broad s, 3 H); 2.09 (broad s, 6 H); 3.44 (q, 2 H); 7.89 (broad s, 3 H); 8.05 (broad s, 1 H); 15.00 (s, 1 H, exch.). Ex. 9: 0.51 (t, 3 H); 3.13 (q, 2 H); 7.66 (t, 1 H); 7.72 (t, 1 H); 7.99 (broad s, 3 H); 8.05 (d, 1 H); 8.12 (broad s, 2 H); 8.22 (broad s, 1 H); 8.64 (s, 1 H); 15.39 (s, 1 H, exch.). Ex. 11: 0.53 (t, 3 H); 3.13 (q, 2 H); 7.71 (d, 2 H); 7.98 (broad s, 3 H); 8.03 (d, 1 H); 8.19 (broad s, 1 H). Ex. 12: 0.56 (t, 3 H); 3.18 (q, 2 H); 7.45 (t, 1 H); 7.53 (t, 2 H); 7.82 (d, 2 H); 7.94-7.98 (m, 5 H); 8.16 (d, 2 H); 8.20-8.21 (m, 1 H); 15.46 (s, 1 H, exch.)

EXAMPLE 13

(5-Chloro-4-hydroxy-2-methyl-1,1-dioxo-2H-benzo[e][1,2]thiazin-3-yl)(naphthalen-2-yl)methanone

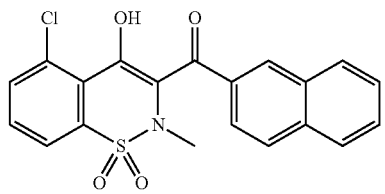 [SMILES: CN1C(C(=O)c2ccc3ccccc3c2)=C(O)c2c(Cl)cccc2S1(=O)=O]

EXAMPLE 13A

2-Chloro-6-sulfamoylbenzoic acid

In a three-neck flask provided with a condenser, 3-chloro-2-methylbenzenesulfonamide (13.27 g, 64.5 mmol) is introduced in the presence of 5% soda in water (385 mL). Potassium permanganate (25.5 g, 161 mmol) is slowly added and then the reaction mixture is heated to 100° C. for 4 hours. The reaction is returned to room temperature, filtered, acidified up to a pH of 1 and extracted 3 times with ethyl acetate. The organic phases are combined, washed once with an aqueous NaCl saturated solution, and then dried on magnesium sulfate, filtered and concentrated in order to obtain the product 13A as a white solid (12.87 g; 83%)

HPLC: RT=1.55 min, 98%

$^1$H NMR, dmso-d$_6$, δ (ppm): 7.48 (s, 2H, exch.); 7.62 (t, 1H); 7.75 (d, 1H); 7.87 (d, 1H); 11-15 (mL, 1H, exch.).

Mass spectrum (ESI−): m/z 234 (M-H$^-$, 55%).

EXAMPLE 13B 4-chlorosaccharin

The compound 13A (12.87 g, 54.6 mmol) is introduced into a flask followed by 38.8 mL of concentrated sulfuric acid. The reaction mixture is stirred at room temperature for 1.5 hours and then poured on a mixture of water and ice. The formed precipitate is filtered, rinsed with water and dried until its weight is constant in order to obtain the compound 13B as a white solid (9.16 g; 77%).

HPLC: RT=2.57 min, 100%

$^1$H NMR, dmso-d$_6$, δ (ppm): 7.91 (broad s, 2H); 8.08 (broad s, 1H).

EXAMPLE 13C 4-chloro-2-(2-(naphthalen-2-yl)-2-oxoethyl)benzo[d]isothiazol-3(2H)-one-1,1-dioxide The compound 13C was synthesized from the compound 13B (2.2 g, 10 mmol) according to the procedure used for preparing the derivative 1A in order to obtain the compound 13C as a pale beige solid (3.3 g; 84%).

HPLC: RT=5.11 min, 99%

$^1$H NMR, dmso-d$_6$, δ (ppm): 5.62 (s, 2H); 7.69 (t, 1H), 7.74 (t, 1H); 7.95-8.20 (m, 6H); 8.38 (d, 1H); 8.92 (s, 1H).

Mass spectrum (ESI+): m/z 386 (MH$^+$, 100%).

EXAMPLE 13D (5-chloro-1,1-dioxo-4-hydroxy-2H-benzo[e][1,2]thiazin-3-yl) (naphthalen-2-yl)methanone The compound 13D was synthesized from the compound 13C (3.3 g, 8.5 mmol) according to the procedure used for preparing the derivative 1B in order to obtain the compound 13D as a golden yellow solid (1.7 g; 51%).

HPLC: RT=5.3 min, 99%

$^1$H NMR, dmso-d$_6$, δ (ppm): 7.68 (t, 1H), 7.72 (t, 1H); 7.85-8.15 (m, 8H); 8.59 (s, 1H); 10.11 (s, 1H).

Mass spectrum (ESI+): m/z 386 (MH$^+$, 100%).

EXAMPLE 13

The compound 13 was synthesized from the compound 13D (3 g, 7.7 mmol) according to the procedure used for preparing the derivative 1 in order to obtain the compound 13 as a yellow solid (2.3 g; 70%).

HPLC: RT=5.75 min, 95%

$^1$H NMR, dmso-d$_6$, δ (ppm): 2.69 (s, 3H); 7.66 (t, 1H); 7.72 (t, 1H); 7.9-8.2 (m, 7H); 8.60 (broad s, 1H); 16.15 (broad s, 1H, exch.).

Mass spectrum (ESI+): m/z 400 (MH$^+$, 100%).

EXAMPLE 14

(5-Chloro-4-hydroxy-2-ethyl-1,1-dioxo-2H-benzo[e][1,2]thiazin-3-yl)(naphthalen-2-yl)methanone

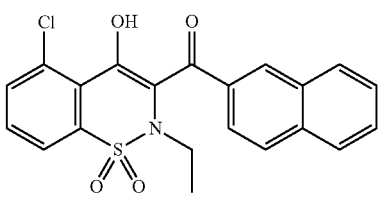 [SMILES: CCN1C(C(=O)c2ccc3ccccc3c2)=C(O)c2c(Cl)cccc2S1(=O)=O]

The compound 14 was synthesized from the compound 13D (1 g, 2.6 mmol) and from iodoethane according to the procedure used for preparing the derivative 1 in order to obtain 805 mg (60%) of the desired product.

HPLC: RT=5.77 min, 81%

A fraction of this product (200 mg) was purified on a column of 12 g of spherical silica (flow rate 12 mL/min, 100% heptane (2 min), EtOAc/heptane gradient from 0 to 50% (30 min), 50% EtOAc/heptane (5 min)), in order to obtain 64 mg of desired product as a yellow solid.

HPLC: RT=5.77 min, 97%

$^1$H NMR, dmso-d$_6$, δ (ppm): 0.51 (t, 3H); 3.11 (q, 2H); 7.66 (t, 1H); 7.72 (t, 1H); 7.85-8.2 (m, 7H); 8.60 (s, 1H); 15.9 (s, 1H, exch.).

Mass spectrum (ESI+): m/z 414 (MH$^+$, 100%).

EXAMPLE 15

(6-Fluoro-4-hydroxy-2-methyl-1,1-dioxo-2H-benzo[e][1,2]thiazin-3-yl)(naphthalen-2-yl)methanone

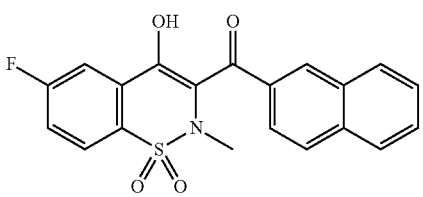 [SMILES: CN1C(C(=O)c2ccc3ccccc3c2)=C(O)c2cc(F)ccc2S1(=O)=O]

EXAMPLE 15A (6-fluoro-4-hydroxy-1,1-dioxo-2H-benzo[e][1,2]thiazin-3-yl) (naphthalen-2-yl)methanone The compound 15A was synthesized from the compound 4-fluoro-2-methylbenzenesulfonamide according to the same sequence of steps involved in preparing the compound 13D. The product is obtained as a yellow solid with an overall yield of 79%.

HPLC: RT=5.26 min, 96%

$^1$H NMR, dmso-d$_6$, δ (ppm): 7.66 (t, 1H); 7.72 (t, 1H); 7.80 (t, 1H); 7.94-8.11 (m, 6H); 8.64 (s, 1H); 10.18 (s, 1H, exch.); 15.2 (broad s, 1H, exch.).

Mass spectrum (ESI−): m/z 368 (M-H$^-$, 100%).

EXAMPLE 15

(6-fluoro-4-hydroxy-2-methyl-1,1-dioxo-2H-benzo[e][1,2]thiazin-3-yl)(naphthalen-2-yl)methanone The compound 15 was synthesized from the compound 15A (1.5 g, 4 mmol) according to the procedure used for preparing the derivative 1 in order to obtain 1.47 g (89%) of the desired product as a yellow solid.

HPLC: RT=5.6 min, 93%

A fraction of this product was recrystallized from ethanol in order to obtain 186 mg of compound 15 with greater purity (HPLC: RT=5.6 min, 99.4%).

$^1$H NMR, dmso-$d_6$, δ (ppm): 2.68 (s, 3H); 7.66 (t, 1H); 7.72 (t, 1H); 7.84 (t, 1H); 7.97 (d, 1H); 8.02-8.15 (m, 5H); 8.66 (s, 1H); 15.22 (broad s, 1H, exch.).

Mass spectrum (ESI+): m/z 384 (MH$^+$, 100%).

EXAMPLE 16

(6-Fluoro-4-hydroxy-2-ethyl-1,1-dioxo-2H-benzo[e][1,2]thiazin-3-yl)(naphthalen-2-yl)methanone

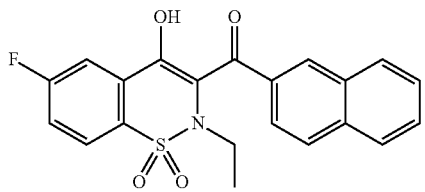 [SMILES: CCN1C(C(=O)c2ccc3ccccc3c2)=C(O)c2cc(F)ccc2S1(=O)=O]

The compound 16 was synthesized from the compound 15A (1.5 g, 4 mmol) and from iodoethane according to the procedure used for preparing the derivative 1 in order to obtain 520 mg (29%) of the desired product as a yellow solid.

HPLC: RT=5.8 min, 91%

A fraction of this product was recrystallized from ethanol in order to obtain 71 mg of compound 16 with greater purity.

HPLC: RT=5.8 min, 97%

$^1$H NMR, dmso-$d_6$, δ (ppm): 0.56 (t, 3H); 3.15 (q, 2H); 7.66 (t, 1H); 7.72 (t, 1H); 7.82 (t, 1H); 7.97 (d, 1H); 8.00-8.2 (m, 5H); 8.63 (s, 1H); 14.95 (broad s, 1H).

Mass spectrum (ESI+): m/z 398 (MH$^+$, 100%).

EXAMPLE 17

(7-Fluoro-4-hydroxy-2-methyl-1,1-dioxo-2H-benzo[e][1,2]thiazin-3-yl)(naphthalen-2-yl)methanone

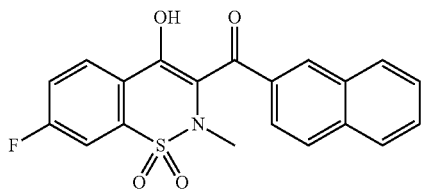 [SMILES: CN1C(C(=O)c2ccc3ccccc3c2)=C(O)c2ccc(F)cc2S1(=O)=O]

EXAMPLE 17A 5-fluoro-2-methylbenzenesulfonamide 5-fluoro-2-methylbenzenesulfonyl chloride (5.00 g, 23.9 mmol) is slowly added at 0° C. onto 23 mL of a concentrated ammonia solution. The reaction medium is then heated to 100° C. for 1 hour and then cooled to room temperature. The formed precipitate is filtered, rinsed with water and dried until it has constant weight. The compound 17A is obtained as a white powder (4.55 g; 100%).

HPLC: RT=3.10 min, 96%

$^1$H NMR, dmso-$d_6$, δ (ppm): 2.54 (s, 3H); 7.35-7.45 (m, 2H); 7.53 (broad s, 2H, exch.); 7.58 (de, 1H).

Mass spectrum (ESI-): m/z 188 (M-H$^-$, 100%).

EXAMPLE 17B (7-Fluoro-4-hydroxy-1,1-dioxo-2H-benzo[e][1,2]thiazin-3-yl)(naphthalen-2-yl)methanone The compound 17B was synthesized from the compound 17A according to the same sequence of steps involved in preparing the compound 13D. The product is obtained as a yellow solid with an overall yield of 73%.

HPLC: RT=5.18 min, 98%

$^1$H NMR, dmso-$d_6$, δ (ppm): 7.66 (t, 1H); 7.72 (t, 1H); 7.81 (t, 1H); 7.90 (d, 1H); 8.04 (d, 2H); 8.11 (broad s, 2H); 8.30 (dd, 1H); 8.63 (s, 1H); 10.19 (broad s, 1H); 15.63 (broad s, 1H).

Mass spectrum (ESI-): m/z 368 (M-H$^-$, 100%).
Mass spectrum (ESI+): m/z 370 (MH$^+$, 100%).

EXAMPLE 17

(7-Fluoro-4-hydroxy-2-methyl-1,1-dioxo-2H-benzo[e][1,2]thiazin-3-yl) (naphthalen-2-yl)methanone The compound 17 was synthesized from the compound 17B (4.00 g, 10.8 mmol) according to the procedure used for preparing the derivative 1 in order to obtain two batches of the desired product with different purities.

First batch: 3.79 g; pale brown solid; HPLC: RT=5.65 min, 94%.

Second batch: 320 mg; yellow solid; HPLC: RT=5.65 min, 99%.

The yield of this reaction is 93%.

$^1$H NMR, dmso-$d_6$, δ (ppm): 2.68 (s, 3H); 7.66 (t, 1H); 7.72 (t, 1H); 7.83 (t, 1H); 7.92 (d, 1H); 8.02-8.15 (m, 4H); 8.28 (dd, 1H); 8.62 (s, 1H); 15.62 (broad s, 1H, exch.).

Mass spectrum (ESI+): m/z 384 (MH$^+$, 100%).

EXAMPLE 18

(7-Fluoro-4-hydroxy-2-ethyl-1,1-dioxo-2H-benzo[e][1,2]thiazin-3-yl)(naphthalen-2-yl)methanone

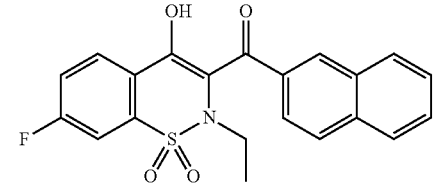 [SMILES: CCN1C(C(=O)c2ccc3ccccc3c2)=C(O)c2ccc(F)cc2S1(=O)=O]

The compound 18 was synthesized from the compound 17A (1.0 g, 2.7 mmol) and from iodoethane according to the procedure used for preparing the derivative 1 in order to obtain two batches of the desired product with different purities.

First batch: 716 mg; pale brown solid; HPLC: RT=5.78 min, 89%.

Second batch: 68 mg; yellow solid; HPLC: RT=5.78 min, 99%.

The yield of this reaction is 65%.

$^1$H NMR, dmso-$d_6$, δ (ppm): 0.54 (t, 3H); 3.14 (q, 2H); 7.66 (t, 1H); 7.71 (t, 1H); 7.82 (t, 1H); 7.92 (d, 1H); 8.00-8.15 (m, 4H); 8.29 (dd, 1H); 8.60 (s, 1H); 15.45 (broad s, 1H, exch.).

Mass spectrum (ESI+): m/z 398 (MH$^+$, 100%).

EXAMPLE 19

Benzoic acid 2-methyl-3-(naphthalene-2-carbonyl)-1,1-dioxo-2H-benzo[e][1,2]thiazin-4-yl ester

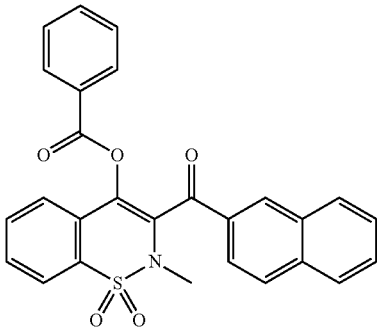 [SMILES: CN1C(C(=O)c2ccc3ccccc3c2)=C(OC(=O)c2ccccc2)c2ccccc2S1(=O)=O]

The compound 1 (86 mg, 0.18 mmol) is dissolved under an inert atmosphere in 0.5 mL of dichloromethane and 0.5 mL of pyridine. The reaction medium is cooled to 0° C. and then benzoyl chloride (33 µl, 0.27 mmol) is added. The cold bath is removed and the reaction is stirred for 4 hours at room temperature. As the reaction is incomplete, 16 µl (0.14 mmol) of benzoyl chloride are further added and the reaction medium is stirred at room temperature for a further 20 hours before being concentrated. The residue is taken up in ethyl acetate, washed once with water and once with an aqueous NaCl saturated solution, dried on sodium sulfate, filtered and concentrated. This second residue is co-evaporated three times with toluene in order to remove the remaining pyridine. The thereby obtained yellow syrup is purified on a column of 12 g of spherical silica (flow rate 12 mL/min, CH$_2$Cl$_2$/heptane gradient from 20 to 100% (30 min)), in order to obtain the compound 19 as a yellow foam (38 mg; 44%).

HPLC: RT=5.65 min, 96%

$^1$H NMR, dmso-d$_6$, δ (ppm): 3.10 (s, 3H); 7.32 (t, 2H); 7.55-7.30 (m, 6H); 7.86 (dd, 2H); 7.90-8.05 (m, 5H); 8.70 (s, 1H).

EXAMPLE 20

Cyclohexanecarboxylic acid 2-methyl-3-(naphthalene-2-carbonyl)-1,1-dioxo-2H-benzo[e][1,2]thiazin-4-yl ester

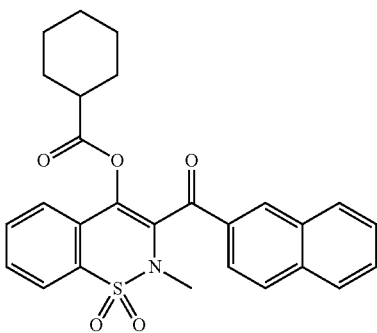 [SMILES: CN1C(C(=O)c2ccc3ccccc3c2)=C(OC(=O)C2CCCCC2)c2ccccc2S1(=O)=O]

The compound 1 (86 mg, 0.18 mmol) is st dissolved under an inert atmosphere in 0.5 mL de pyridine. The reaction medium is cooled to 0° C. and then cyclohexanecarbonyl chloride (62 µl, 0.46 mmol) is added. The cold bath is removed and the reaction is stirred for 18 hours at room temperature, and then heated to 60° C. for 8 hours. The reaction mixture is concentrated and co-evaporated three times with toluene. The thereby obtained residue is purified on a column of 12 g of spherical silica (flow rated 12 mL/min, CH$_2$Cl$_2$/heptane gradient from 20 to 100% (20 min)), in order to obtain the compound 20 as a yellow foam (65 mg; 28%).

HPLC: RT=5.99 min, 95%

$^1$H NMR, dmso-d$_6$, δ (ppm): 0.85-1.00 (m, 6H); 1.38 (de, 2H); 1.49 (de, 2H); 2.28 (tt, 1H); 3.06 (s, 3H); 7.66 (t, 2H); 7.75 (t, 1H); 7.83 (t, 1H); 7.88 (t, 1H); 7.95-8.15 (m, 5H); 8.66 (s, 1H).

Mass spectrum (ESI+): m/z 493 (MNH$_4^+$, 100%).

EXAMPLE 21 tertButylcarboxylic acid 2-methyl-3-(naphthalene-2-carbonyl)-1,1-dioxo-2H-benzo[e][1,2]thiazin-4-yl ester

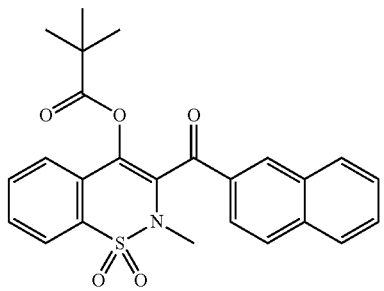 [SMILES: CN1C(C(=O)c2ccc3ccccc3c2)=C(OC(=O)C(C)(C)C)c2ccccc2S1(=O)=O]

The compound 1 (86 mg, 0.18 mmol) is dissolved under inert atmosphere in 0.5 mL of pyridine. The reaction medium is cooled to 0° C. and then tertbutylcarbonyl chloride (57 µl, 0.46 mmol) is added. The cold bath is removed and the reaction is stirred for 18 hours at room temperature. The reaction medium is concentrated and co-evaporated three times with toluene. The thereby obtained residue is purified on a column of 12 g of spherical silica (flow rate 12 mL/min, CH$_2$Cl$_2$/heptane gradient from 20 to 100% (20 min)), in order to obtain the compound 21 as a yellow foam (47 mg; 53%).

HPLC: RT=5.71 min, 98%

$^1$H NMR, dmso-d$_6$, δ (ppm): 0.88 (s, 9H); 3.07 (s, 3H); 7.59 (d, 1H); 7.66 (t, 1H); 7.75 (t, 1H); 7.84 (t, 1H); 7.89 (t, 1H); 8.00-8.09 (m, 4H); 8.12 (d, 1H); 8.69 (s, 1H).

Mass spectrum (ESI+): m/z 467 (MNH$_4^+$, 100%).

EXAMPLE 22

4-Methylbenzoic acid 2-methyl-3-(naphthalene-2-carbonyl)-1,1-dioxo-2H-benzo[e][1,2]thiazin-4-yl ester

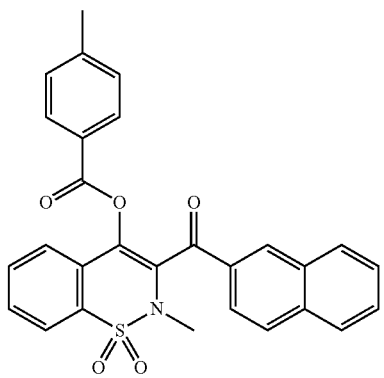 [SMILES: Cc1ccc(C(=O)OC2=C(C(=O)c3ccc4ccccc4c3)N(C)S(=O)(=O)c3ccccc32)cc1]

The compound 22 was synthesized according to the same procedure as for compound 21 from the compound 1 (86 mg, 0.18 mmol) and from 4-methylbenzoyl chloride (62 µl, 0.46 mmol). The product is obtained as a yellow foam (27 mg; 31%).

HPLC: RT=5.82 min, 95%

$^1$H NMR, dmso-d$_6$, δ (ppm): 2.28 (s, 3H); 3.10 (s, 3H); 7.11 (d, 2H); 7.54 (d, 2H); 7.65 (t, 1H); 7.73 (te, 2H); 7.86 (dd, 2H); 7.95 (d, 1H); 7.97-8.05 (m, 4H); 8.69 (s, 1H).

Mass spectrum (ESI+): m/z 501 (MNH$_4^+$, 100%).

EXAMPLE 23

4-Chlorobenzoic acid 2-methyl-3-(naphthalene-2-carbonyl)-1,1-dioxo-2H-benzo[e][1,2]thiazin-4-yl ester

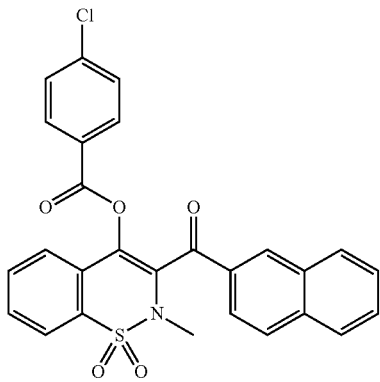 [SMILES: CN1C(C(=O)c2ccc3ccccc3c2)=C(OC(=O)c2ccc(Cl)cc2)c2ccccc2S1(=O)=O]

4-chlorobenzoic acid (87 mg, 0.55 mmol) is dissolved in 2 mL of toluene under an inert atmosphere. Oxalyl chloride (100 µl, 1.1 mmol) is added at room temperature. The reaction mixture is heated for 2 hours to 80° C., and then concentrated and co-evaporate three times with toluene. The residue is put back under an inert atmosphere and cooled to 0° C. The compound 1 (86 mg, 0.18 mmol) dissolved under an inert atmosphere in 0.5 mL of pyridine and cooled to 0° C. is added. The cold bath is removed and the reaction is stirred for 2 hours at room temperature. The reaction medium is concentrated and co-evaporated three times with toluene. The thereby obtained residue is purified on a column of 12 g of spherical silica (flow rate 12 mL/min, $CH_2Cl_2$/heptane gradient from 20 to 100% (20 min)), in order to obtain the compound 23 as a yellow foam (51 mg; 42%).

HPLC: RT=5.92 min, 97%

$^1$H NMR, dmso-$d_6$, δ (ppm): 3.10 (s, 3H); 7.37 (d, 2H); 7.63-7.67 (m, 3H); 7.72 (t, 1H); 7.79 (broad s, 1H); 7.86 (broad s, 2H); 7.94 (d, 1H); 7.95-8.07 (m, 4H); 8.66 (s, 1H).

Mass spectrum (ESI+): m/z 521 ($MNH_4^+$, 100%); 523 ($MNH_4^+$, 37%).

EXAMPLES 24 TO 27

The compounds 24 to 27 were synthesized according to the procedure described for preparing the compound 21, from the compound 15 and from various acid chlorides.

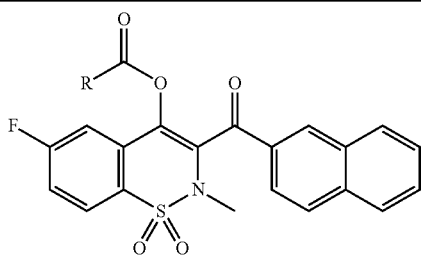

| Ex. * | R | Name of the compounds | HPLC | Yld. | Mass $MNH_4^+$ |
|---|---|---|---|---|---|
| 24 | tertButyl | tertButylcarboxylic acid 6-fluoro-2-methyl-3-(naphthalene-2-carbonyl)-1,1-dioxo-2H-benzo[e][1,2]thiazin-4-yl ester | 5.82' | 61% 98% | 485 |

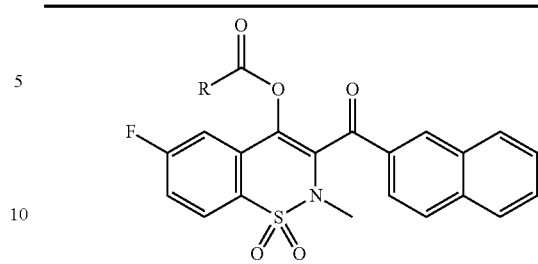

| Ex. * | R | Name of the compounds | HPLC | Yld. | Mass $MNH_4^+$ |
|---|---|---|---|---|---|
| 25 | Cyclohexane | Cyclohexanecarboxylic acid 6-fluoro-2-methyl-3-(napthalene-2-carbonyl)-1,1-dioxo-2H-benzo[e][1,2]thiazin-4-yl ester | 6.09' | 36% 90% | 511 |
| 26 | Phenyl | Benzoic acid 6-fluoro-2-methyl-3-(naphthalene-2-carbonyl)-1,1-dioxo-2H-benzo[e][1,2]thiazin-4-yl ester | 5.73' | 64% 96% | 505 |
| 27 | 4-methylphenyl | 4-methylbenzoic acid 6-fluoro-2-methyl-3-(naphthalene-2-carbonyl)-1,1-dioxo-2H-benzo[e][1,2]thiazin-4-yl ester | 5.91' | 56% 95% | 519 |

* $^1$H NMR, dmso-$d_6$, Ex. 24: 0.87 (s, 9 H); 3.08 (s, 3 H); 7.32 (d, 1 H); 7.63-7.80 (m, 3 H); 7.95-8.15 (m, 5 H); 8.69 (s, 1 H). Ex. 25: 0.80-1.10 (m, 5 H); 1.15-1.55 (m, 5 H); 2.39 (te, 1 H); 3.08 (s, 3 H); 7.56 (d, 1 H); 7.65-7.70 (m, 2 H); 7.76 (t, 1 H); 7.95-8.15 (m, 5 H); 8.67 (s, 1 H). Ex. 26: 3.12 (s, 3 H); 7.29 (t, 2 H); 7.55-7.75 (m, 7 H); 7.94 (d, 1 H); 7.98-8.15 (m, 3 H); 8.15 (dd, 1 H); 8.69 (s, 1 H). Ex. 27: 2.28 (s, 3 H); 3.11 (s, 3 H); 7.09 (d, 2 H); 7.51 (d, 2 H); 7.60-7.76 (m, 4 H); 7.94 (d, 1 H); 7.99-8.08 (m, 3 H); 8.13 (dd, 1 H); 8.69 (s, 1 H).

EXAMPLES 28 TO 31

The compounds 28 to 31 were synthesized according to the procedure described for preparing compound 21, from the compound 16 and various acid chlorides.

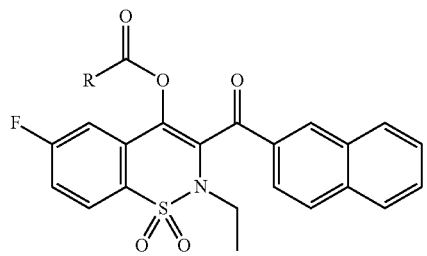

| Ex. * | R | Name of the compounds | HPLC | Yld | Mass $MNH_4^+$ |
|---|---|---|---|---|---|
| 28 | tertButyl | tertButylcarboxylic acid 6-fluoro-2-ethyl-3-(naphthalene-2-carbonyl)-1,1-dioxo-2H-benzo[e][1,2]thiazin-4-yl ester | 6.00' | 53% 98% | 499 |
| 29 | Cyclohexane | Cyclohexanecarboxylic acid 6-fluoro-2-ethyl-3-(naphthalene-2-carbonyl)-1,1-dioxo-2H-benzo[e][1,2]thiazin-4-yl ester | 6.26' | 42% 95% | 525 |
| 30 | Phenyl | Benzoic acid 6-fluoro-2-ethyl-3-(naphthalene-2-carbonyl)-1,1-dioxo-2H- | 5.90' | 40% 99% | 519 |

-continued

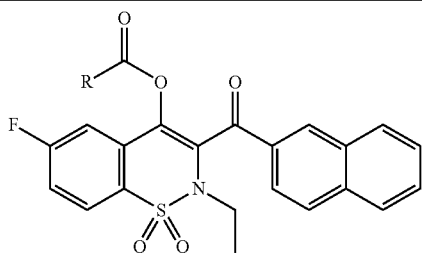

| Ex. * | R | Name of the compounds | HPLC | Yld | Mass MNH$_4^+$ |
|---|---|---|---|---|---|
| 31 | 4-methyl-phenyl | benzo[e][1,2]thiazin-4-yl ester 4-methylbenzoic acid 6-fluoro-2-ethyl-3-(naphthalene-2-carbonyl)-1,1-dioxo-2H-benzo[e][1,2]thiazin-4-yl ester | 6.08' 95% | 59% | 533 |

* $^1$H NMR, dmso-d$_6$, Ex. 28: 0.92 (broad s, 12 H); 3.56 (q, 2 H); 7.34 (d, 1 H); 7.63-7.80 (m, 3 H); 8.00-8.15 (m, 5 H); 8.68 (s, 1 H). Ex. 29: 0.80-1.10 (m, 8 H); 1.38 (broad s, 3 H); 1.53 (de, 2 H); 2.45 (te, 1 H); 3.55 (q, 2 H); 7.56 (d, 1 H); 7.65-7.70 (m, 2 H); 7.76 (t, 1 H); 7.95-8.15 (m, 5 H); 8.67 (s, 1 H). Ex. 30: 0.95 (t, 3 H); 3.58 (q, 2 H); 7.35 (t, 2 H); 7.55-7.75 (m, 7 H); 7.96 (d, 1 H); 7.98-8.10 (m, 3 H); 8.14 (dd, 1 H); 8.69 (s, 1 H). Ex. 31: 0.95 (t, 3 H); 2.30 (s, 3 H); 3.57 (q, 2 H); 7.15 (d, 2 H); 7.60-7.76 (m, 6 H); 7.95 (d, 1 H); 7.99-8.08 (m, 3 H); 8.14 (dd, 1 H); 8.68 (s, 1 H).

EXAMPLES 32 AND 33

The compounds 32 and 33 were synthesized according to the procedure described for preparing the compound 23, from 4-chlorobenzoic acid and from the compounds 15 and 16, respectively.

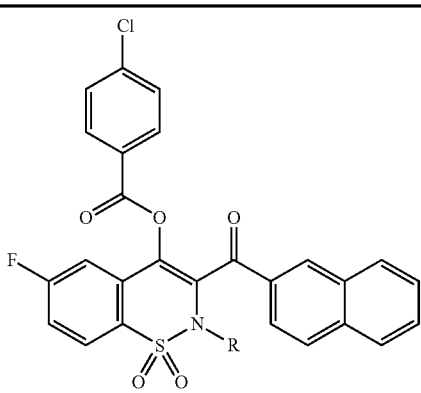

| Ex. * | R | Name of the compounds | HPLC | Yld | Mass MNH$_4^+$ |
|---|---|---|---|---|---|
| 32 | Methyl | 4-Chlorobenzoic acid 6-fluoro-2-methyl-3-(naphthalene-2-carbonyl)-1,1-dioxo-2H-benzo[e][1,2]thiazin-4-yl ester | 6.00' 95% | 18% | 539 |
| 33 | Ethyl | 4-Chlorobenzoic acid 6-fluoro-2-ethyl-3-(naphthalene-2-carbonyl)-1,1-dioxo-2H-benzo[e][1,2]thiazin-4-yl ester | 6.16' 95% | 19% | 553 |

* $^1$H NMR, dmso-d$_6$, Ex. 32: 3.12 (s, 3 H); 7.34 (d, 2 H); 7.55-7.76 (m, 6 H); 7.92 (d, 1 H); 7.95-8.05 (m, 3 H); 8.14 (dd, 1 H); 8.65 (s, 1 H). Ex. 33: 0.95 (t, 3 H); 3.58 (q, 2 H); 7.40 (d, 2 H); 7.60-7.80 (m, 6 H); 7.94 (d, 1 H); 7.00-8.05 (m, 3 H); 8.14 (dd, 1 H); 8.65 (s, 1 H).

EXAMPLE 34

Naphthalen-1-ylcarboxylic acid 2-methyl-3-(4-methylbenzoyl)-1,1-dioxo-2H-benzo[e][1,2]thiazin-4-yl ester

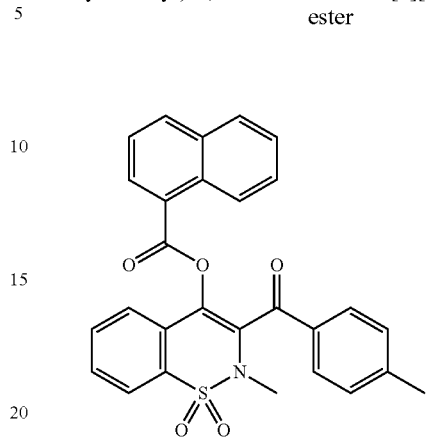

The compound 3 (150 mg, 0.455 mmol) is dissolved under an inert atmosphere in 3 mL of tetrahydrofurane. Sodium hydride (27 mg, 0.68 mmol) is added, followed by naphthalen-2-ylcarbonyl chloride (105 µl, 0.68 mmol) 30 minutes later. The reaction is stirred for 4 hours at room temperature. The reaction medium is neutralized with water and the aqueous phase is extracted twice with ethyl acetate. The organic phases are combined, dried on magnesium sulfate, filtered and concentrated. The thereby obtain residue is purified on a column of 12 g of spherical silica (flow rate 12 mL/min, gradient of 0 to 45% EtOAc in heptane (20 min)). The product is obtained as a yellow solid (134 mg; 61%).

HPLC: RT=6.59 min, 98%
$^1$H NMR, dmso-d$_6$, δ (ppm): 2.35 (s, 3H); 3.08 (s, 3H); 7.36 (d, 2H); 7.54 (t, 1H); 7.58-7.63 (m, 2H); 7.79-7.87 (m, 3H); 7.92 (d, 2H); 8.00 (d, 1H); 8.04-8.07 (m, 2H); 8.27 (d, 1H); 8.50-8.55 (m, 1H).
Mass spectrum (ESI+): m/z 501 (MNH$_4^+$, 100%).

EXAMPLES 35 TO 45

The compounds 35 to 45 were synthesized according to the procedure described for preparing the compound 34, from the compound 3 or from the compound 5 and from various acid chlorides.

In the examples 40 to 45, the acid chlorides required for the reaction are prepared in two steps from the corresponding aromatic alcohol. The preparation of (naphthalen-2-yloxy) acetyl chloride is given as an example:

In a two-neck flask provided with a condenser and placed under an inert atmosphere, 2-naphthol (3.0 g, 20 mmol) is dissolved in 95 mL of methylethylketone (MEK) in the presence of soda (40 g, 93 mmol), and then heated to 50° C. for 30 minutes. 2-bromoethanoic acid (5.76 g, 41 mmol) dissolved in 23 mL of MEK is added dropwise under hot conditions. The heating is maintained for a further 4 hours. The reaction medium is cooled to room temperature and then filtered. The solid collected by filtration is taken up in a mixture of ethyl acetate and of 1N HCl in water. Both phases are separated and the aqueous phase is extracted once with ethyl acetate. The organic phases are collected, dried on magnesium sulfate, filtered and concentrated until the first crystals appear. Heptane is added (about 20% of the remaining volume), and the formed precipitate is recovered, rinsed with heptane and dried until it has constant weight in order to obtain 3.04 g (72%) of (naphthalen-2-yloxy)acetic acid as a white solid.

HPLC: RT=4.10' min, 99%

$^1$H NMR, dmso-d$_6$, δ (ppm): 4.80 (s, 2H); 7.20 (dd, 1H); 7.26 (d, 1H); 7.35 (td, 1H); 7.45 (td, 1H); 7.79 (d, 1H); 7.80-7.86 (m, 2H); 13.07 (broad s, 1H, exch.).

Mass spectrum (ESI+): m/z 203 (MH$^+$, 100%).

Mass spectrum (ESI−): m/z 201 (M-H, 100%).

The acid formed earlier (3.04 g, 15 mmol) is partly dissolved under an inert atmosphere and at room temperature in 34 mL of dichloromethane. Oxalyl chloride (1.35 mL, 15.7 mmol) is added followed by 100 µl of DMF. Caution, a violent reaction occurs upon adding DMF. The reaction mixture is stirred for 1 hour and then concentrated, co-evaporated twice with toluene and dried until it has constant weight in order to obtain 3.4 g (100%) of (naphthalen-2-yloxy)acetyl chloride as an orangey solid. The thereby formed acid chloride was used as such in preparing the compounds 40 and 41.

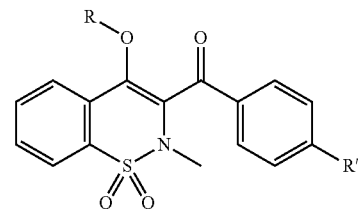

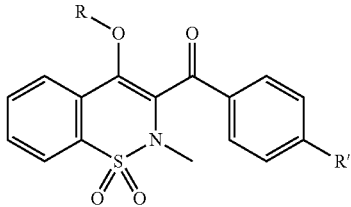

| Ex. * | R | R' | Name of the compounds | HPLC | Yld | Mass MNH$_4^+$ |
|---|---|---|---|---|---|---|
| 35 | Naphthalen-2-carbonyl | CH$_3$ | Naphthalen-2-ylcarboxylic acid 2-methyl-3-(4-methylbenzoyl)-1,1-dioxo-2H-benzo[e][1,2]thiazin-4-yl ester | 5.89' | 81% 99% | 501 |
| 36 | Naphthalen-1-carbonyl | CN | Napthalen-1-ylcarboxylic acid 2-methyl-3-(4-cyanobenzoyl)-1,1-dioxo-2H-benzo[e][1,2]thiazin-4-yl ester | 5.59' | 85% 98% | 512 |
| 37 | Naphthalen-2-carbonyl | CN | Naphthalen-2-ylcarboxylic acid 2-methyl-3-(4-cyanobenzoyl)-1,1-dioxo-2H-benzo[e][1,2]thiazin-4-yl ester | 5.58' | 30% 93% | 512 |
| 38 | 4-chloro benzoyl | CH$_3$ | 4-Chlorobenzoic acid 2-methyl-3-(4-methylbenzoyl)-1,1-dioxo-2H-benzo[e][1,2]thiazin-4-yl ester | 5.82' | 24% 96% | 485 |
| 39 | 4-chloro benzoyl | CN | 4-Chlorobenzoic acid 2-methyl-3-(4-cyanobenzoyl)-1,1-dioxo-2H-benzo[e][1,2]thiazin-4-yl ester | 5.48' | 19% 91% | 496 |
| 40 | (Naphthalen-2-yloxy) acetyl | CH$_3$ | (Naphthalene-2-yloxy)acetic acid 2-methyl-3-(4-methylbenzoyl)-1,1-dioxo-2H-benzo[e][1,2]thiazin-4-yl ester | 5.87' | 85% 98% | 531 |
| 41 | (Naphthalen-2-yloxy) acetyl | CN | (Naphthalene-2-yloxy)acetic acid 2-methyl-3-(4-cyanobenzoyl)-1,1-dioxo-2H-benzo[e][1,2]thiazin-4-yl ester | 5.59' | 21% 98% | 542 |
| 42 | (Naphthalen-1-yloxy) acetyl | CH$_3$ | (Naphthalene-1-yloxy)acetic acid 2-methyl-3-(4-methylbenzoyl)-1,1-dioxo-2H-benzo[e][1,2]thiazin-4-yl ester | 5.89' | 60% 98% | 531 |
| 43 | (Napthalen-1-yloxy) acetyl | CN | (Naphthalene-1-yloxy)acetic acid 2-methyl-3-(4-cyanobenzoyl)-1,1-dioxo-2H-benzo[e][1,2]thiazin-4-yl ester | 5.64' | 29% 97% | 542 |
| 44 | (4-chloro phenoxy) acetyl | CH$_3$ | (4-Chlorophenoxy)acetic acid 2-methyl-3-(4-methylbenzoyl)-1,1-dioxo-2H-benzo[e][1,2]thiazin-4-yl ester | 5.76' | 64% 99% | 515 |
| 45 | (4-chloro phenoxy) acetyl | CN | (4-Chlorophenoxy)acetic acid 2-methyl-3-(4-cyanobenzoyl)-1,1-dioxo-2H-benzo[e][1,2]thiazin-4-yl ester | 5.50' | 31% 90% | 526 |

* $^1$H NMR, dmso-d$_6$, Ex. 35: 2.34 (s, 3 H); 3.07 (s, 3 H); 7.35 (d, 2 H); 7.65 (t, 1 H); 7.72 (t, 1 H); 7.75-7.92 (m, 6 H); 7.95-8.06 (m, 4 H); 8.39 (s, 1 H). Ex. 36: 3.07 (s, 3 H); 7.58 (t, 1 H); 7.61-7.68 (m, 2 H); 7.89 (broad s, 3 H); 7.98 (d, 2 H); 8.00-8.10 (m, 5 H); 8.31 (d, 1 H); 8.60 (dd, 1 H). Ex. 37: 3.08 (s, 3 H); 7.67 (t, 1 H); 7.71-7.79 (m, 2 H); 7.90 (broad s, 3 H); 7.99-8.11 (m, 8 H); 8.40 (s, 1 H). Ex. 38: 2.38 (s, 3 H); 3.04 (s, 3 H); 7.35 (d, 2 H); 7.58 (d, 2 H); 7.70-7.80 (m, 3 H); 7.83-8.88 (m,4 H); 8.02 (broad s, 1 H). Ex. 39: 3.04 (s, 3 H); 7.59 (d, 2 H); 7.83-7.90 (m, 3 H); 7.99-8.07 (m, 5 H). Ex. 40: 2.38 (s, 3 H); 2.97 (s, 3 H); 5.10 (s, 2 H); 7.13 (dd, 1 H); 7.20 (d, 1 H); 7.36-7.41 (m, 3 H); 7.48 (t, 1 H); 7.67 (d, 1 H); 7.80-7.99 (m, 7 H); 8.00 (broad s, 1 H). Ex. 41: 2.94 (s, 3 H); 5.14 (s, 2 H); 7.15 (dd, 1 H); 7.25 (d, 1 H); 7.38 (t, 1 H); 7.47 (t, 1 H); 7.69 (d, 1 H); 7.81-7.94 (m, 5 H); 7.99-8.10 (m, 5 H). Ex. 42: 2.38 (s, 3 H); 2.99 (s, 3 H); 5.14 (s, 2 H); 6.70 (d, 1 H); 7.28 (t, 1 H); 7.40 (d, 2 H); 7.47-7.55 (m, 3 H); 7.81-7.88 (m, 4 H); 7.92 (d, 2 H); 8.00 (d, 1 H); 8.08 (d, 1 H). ). Ex. 43: 2.96 (s, 3 H); 5.20 (s, 2 H); 6.82 (d, 1 H); 7.34 (t, 1 H); 7.49-7.56 (m, 3 H); 7.88-7.56 (m, 4 H); 8.00-8.02 (m, 1 H); 8.05-8.11 (m, 5 H). Ex. 44: 2.42 (s, 3 H); 2.97 (s, 3 H); 4.98 (s, 2 H); 6.81 (d, 2 H); 7.23 (d, 2 H); 7.42 (d, 2 H); 7.81-7.92 (m, 5 H); 7.99 (d, 1 H). Ex. 45: 2.95 (s, 3 H); 5.01 (s, 2 H); 6.90 (d, 2 H); 7.28 (d, 2 H); 7.85-8.15 (m, 8 H).

EXAMPLE 46

Acetic acid 2-methyl-3-(naphthalene-2-carbonyl)-1,1-dioxo-2H-benzo[e][1,2]thiazin-4-yl ester

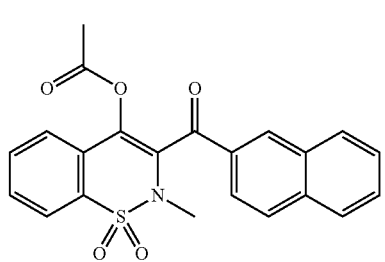 [SMILES: CC(=O)OC1=C(C(=O)c2ccc3ccccc3c2)N(C)S(=O)(=O)c2ccccc21]

The compound 1 (100 mg, 0.274 mmol) is dissolved under an inert atmosphere in 2 mL of dichloromethane. Triethylamine (230 μl, 1.64 mmol) is added at 0° C., followed by acetyl chloride (78 μl, 1.09 mmol). The reaction medium is stirred at room temperature for 18 hours and then concentrated. The thereby obtained residue is purified on a column of 12 g of spherical silica in order to obtain the compound 46 (21 mg; 30%).

HPLC: RT=5.34 min, 97%.

$^1$H NMR, dmso-$d_6$, δ (ppm): 1.96 (s, 3H); 3.03 (s, 3H); 7.66 (t, 1H); 7.75 (t, 1H); 7.80-7.91 (m, 3H); 7.99-8.08 (m, 4H); 8.12 (d, 1H); 8.67 (s, 1H).

Mass spectrum (ESI+): m/z 425 (MNH$_4^+$, 100%).

EXAMPLES 47 TO 54

The compounds 47 to 54 were synthesized according to the procedure described for preparing the compound 46, from the compound 1 and from various acid chlorides.

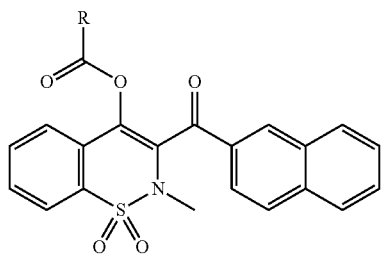

| Ex. | R | Name of the compounds | HPLC | Yld. | Mass MNH$_4^+$ |
|---|---|---|---|---|---|
| 47 | 2,4-dichloro-phenyl | 2,4-Dichlorobenzoic acid 2-methyl-3-(naphthalene-2-carbonyl)-1,1-dioxo-2H-benzo[e][1,2]thiazin-4-yl ester | 6.05' | 47% 98% | 555 |
| 48 | 4-fluoro-phenyl | 4-Fluorobenzoic acid 2-methyl-3-(naphthalene-2-carbonyl)-1,1-dioxo-2H-benzo[e][1,2]thiazin-4-yl ester | 5.86' | 69% 98% | 505 |
| 49 | Cyclo-pentyl | Cyclopentanoic acid 2-methyl-3-(naphthalene-2-carbonyl)-1,1-dioxo-2H-benzo[e][1,2]thiazin-4-yl ester | 5.99' | 48% 91% | 479 |
| 50 | Furan-2-yl | 2-Furanoic acid 2-methyl-3-(napthalene-2-carbonyl)-1,1-dioxo-2H-benzo[e][1,2]thiazin-4-yl ester | 5.33' | 68% 97% | 477 |
| 51 | Thiophen-2-yl | Thiophen-2-carboxylic acid 2-methyl-3-(naphthalene-2-carbonyl)-1,1-dioxo-2H-benzo[e][1,2]thiazin-4-yl ester | 5.68' | 61% 99% | 493 |
| 52 | 3-chloro-phenyl | 3-Chlorobenzoic acid 2-methyl-3-(naphthalene-2-carbonyl)-1,1-dioxo-2H-benzo[e][1,2]thiazin-4-yl ester | 5.87' | 45% 98% | 521 |
| 53 | 2-chloro-phenyl | 2-Chlorobenzoic acid 2-methyl-3-(naphthalene-2-carbonyl)-1,1-dioxo-2H-benzo[e][1,2]thiazin-4-yl ester | 5.74' | 63% 96% | 521 |

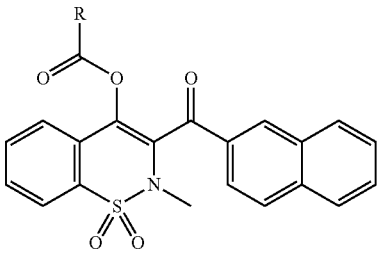

| Ex. | R | Name of the compounds | HPLC | Yld. | Mass MNH$_4^+$ |
|---|---|---|---|---|---|
| 54 | Phenoxy-methyl | Phenoxyacetic acid 2-methyl-3-(naphthalene-2-ylcarbonyl)-1,1-dioxo-2H-benzo[e][1,2]thiazin-4-yl ester | 5.63' | 71% 97% | 517 |

* $^1$H NMR, dmso-$d_6$, Ex. 47: 3.11 (s, 3 H); 7.29 (d, 1 H); 7.58 (d, 1 H); 7.62-7.68 (m, 2 H); 7.72 (t, 1 H); 7.82-7.92 (m, 3 H); 7.95-8.09 (m, 5 H); 8.66 (s, 1 H). Ex. 48: 3.10 (s, 3 H); 7.15 (t, 2 H); 7.63-8.08 (m, 12 H); 8.67 (s, 1 H). Ex. 49: 1.20-1.31 (m, 6 H); 1.50-1.58 (m, 2 H); 2.75 (quintet, 1 H); 3.07 (s, 3 H); 7.64-7.70 (m, 2 H); 7.74 (t, 1 H); 7.84 (t, 1 H); 7.89 (t, 1 H); 7.99-8.08 (m, 4 H); 8.12 (d, 1 H); 8.67 (s, 1 H). Ex. 50: 3.08 (s, 3 H); 6.60 (d, 1 H); 7.19 (d, 1 H); 7.65 (t, 1 H); 7.72-7.77 (m, 2 H); 7.88 (broad s, 2 H); 7.95-8.08 (m, 6 H); 8.69 (s, 1 H). Ex. 51: 3.09 (s, 3 H); 7.09 (dd, 1 H); 7.62-8.04 (m, 12 H); 8.20 (s, 1 H). Ex. 52: 3.12 (s, 3 H); 7.6 (t, 1 H); 7.41 (s, 1 H); 7.60-7.67 (m, 3 H); 7.72 (t, 1 H); 7.82-8.08 (m, 8 H); 8.69 (s, 1 H). Ex. 53: 3.11 (s, 3 H); 7.20 (t, 1 H); 7.49-7.57 (m, 3 H); 7.65 (t, 1 H); 7.73 (t, 1 H); 7.80 (d, 1 H); 7.85-7.93 (m, 2 H); 7.98-8.09 (m, 5 H); 8.71 (s, 1 H). Ex. 51: (t, 2 H); 7.65 (t, 1 H); 7.76 (t, 1 H); 7.83-7.92 (m, 3 H); 8.03-8.09 (m, 4 H); 8.14 (d, 1 H); 8.71 (s, 1 H).

EXAMPLE 55

(4-Methoxy-2-methyl-1,1-dioxo-2H-benzo[e][1,2]thiazin-3-yl)(naphthalen-2-yl)methanone

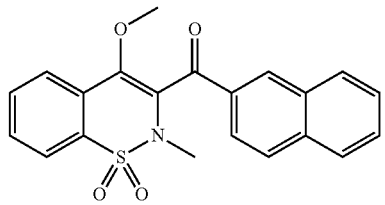 [SMILES: COC1=C(C(=O)c2ccc3ccccc3c2)N(C)S(=O)(=O)c2ccccc21]

The compound 1 (159 mg, 0.435 mmol) is dissolved under an inert atmosphere in 2 mL of DMF. Sodium hydride (26 mg, 0.65 mmol) is added, followed by methane iodide (30 μl, 0.48 mmol) 30 minutes later. The reaction is stirred for 2 hours at room temperature, and then for 26 hours at 60° C. At this stage, the reaction is still incomplete. Cesium carbonate (213 mg, 0.65 mmol) and methane iodide (150 μl, 2.1 mmol) are added. The reaction medium is stirred for 24 hours at room temperature and then neutralized with water, and the aqueous phase is extracted twice with ethyl acetate. The organic phases are combined, dried on magnesium sulfate, filtered and concentrated. The thereby obtained residue is purified on a column of 12 g of spherical silica (flow rate 12 mL/min, gradient of 20 to 60% dichloromethane in heptane), in order to obtain the compound 55 as a yellow foam (70 mg; 38%).

HPLC: RT=5.27 min, 90%

Mass spectrum (ESI+): m/z 380 (MH$^+$, 100%).

EXAMPLES 56 TO 58

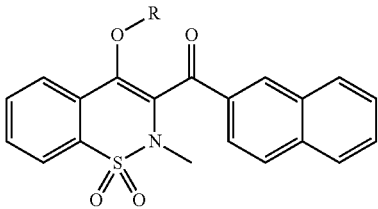

The compounds 56 to 58 were prepared according to the following procedure:

The compound 1 (150 mg, 0.42 mmol) is dissolved under an inert atmosphere in 0.3 mL of DMF. Cesium carbonate (201 mg, 0.61 mmol) and the require alkyl iodide (4 mmol) are added. The reaction medium is stirred for 18 hours at room temperature, for 4 hours at 50° C. and then neutralized with water, and the aqueous phase is extracted twice with ethyl acetate. The organic phases are combined, dried on magnesium sulfate, filtered and concentrated. The thereby obtained residues are purified on columns of 12 g of spherical silica (flow rate 12 mL/min, gradient of 20 to 60% dichloromethane in heptane), in order to obtain the desired products.

| Ex. | R | Name of the compounds | HPLC | Yld. | Mass MH+ |
|---|---|---|---|---|---|
| 56 | Ethyl | (4-ethoxy-2-methyl-1,1-dioxo-2H-benzo[e][1,2]thiazin-3-yl)(naphthalen-2-yl)methanone | 5.43' | 66% 99% | 394 |
| 57 | n-Propyl | (4-propyloxy-2-methyl-1,1-dioxo-2H-benzo[e][1,2] thiazin-3-yl)(naphthalen-2-yl)methanone | 5.61' | 65% 99% | 408 |
| 58 | n-Butyl | (4-butyloxy-2-methyl-1,1-dioxo-2H-benzo[e][1,2] thiazin-3-yl)(naphthalen-2-yl)methanone | 5.81' | 24% 97% | 422 |

* $^1$H NMR, dmso-d$_6$, Ex. 56: 0.87 (t, 3H); 2.98 (s, 3H); 3.74 (q, 2H); 7.64 (t, 1H); 7.72 (t, 1H); 7.80-7.93 (m, 3H); 7.95-8.15 (m, 5H); 8.67 (s, 1H). Ex. 57: 0.49 (t, 3H); 1.28 (sextet, 2H); 2.97 (s, 3H); 3.63 (t, 2H); 7.64 (t, 1H); 7.72 (t, 1H); 7.80-7.93 (m, 3H); 7.95-8.15 (m, 5H); 8.68 (s, 1H). Ex. 58: 0.50 (t, 3H); 0.89 (sextet, 2H); 1.23 (quintet, 2H); 2.97 (s, 3H); 3.66 (t, 2H); 7.64 (t, 1H); 7.72 (t, 1H); 7.80-7.93 (m, 3H); 7.95-8.15 (m, 5H); 8.67 (s, 1H).

EXAMPLE 59

(4-(2-Chloroethoxy)-2-methyl-1,1-dioxo-2H-benzo[e][1,2]thiazin-3-yl)(p-tolyl)methanone

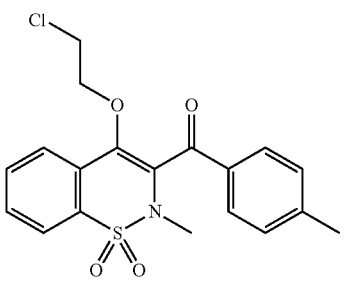 [SMILES: Cc1ccc(C(=O)C2=C(OCCCl)c3ccccc3S(=O)(=O)N2C)cc1]

The compound 3 (100 mg, 0.3 mmol) is dissolved in 3 mL of THF, under an inert atmosphere and in the presence of 2-chloroethanol (100 µl, 1.5 mmol). The reaction mixture is cooled to 0° C., and then triphenylphosphine (318 mg, 1.2 mmol) and diethyldiazene-1,2-dicarboxylate (DEAD, 211 mg, 1.2 mmol) are successively added dropwise. Stirring is continued for 20 hours at room temperature, and then the reaction is neutralized with an aqueous solution saturated with ammonium chloride. This aqueous phase is extracted twice with ethyl acetate. The organic phases are combined, dried on magnesium sulfate, filtered and concentrated. The thereby obtained residue is purified on a column of 35 g of silica (flow rate 20 mL/min, gradient of 0 to 100% ethyl acetate in heptane), in order to obtain the compound 59 (70 mg; 58%).

HPLC: RT=5.28 min, 99%

$^1$H NMR, dmso-d$_6$, δ (ppm): 2.41 (s, 3H); 2.91 (s, 3H); 3.57 (t, 2H); 3.92 (t, 2H); 7.40 (d, 2H,); 7.75-7.98 (m, 6H).

Mass spectrum (ESI+): m/z 392 (MH$^+$, 100%); 394 (MH$^+$, 42%).

EXAMPLE 60

(4-[2-(Naphthalen-2-yloxy)ethoxy]-2-methyl-1,1-dioxo-2H-benzo[e][1,2]thiazin-3-yl)(p-tolyl)methanone

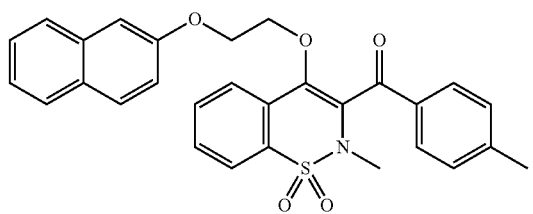 [SMILES: Cc1ccc(C(=O)C2=C(OCCOc3ccc4ccccc4c3)c3ccccc3S(=O)(=O)N2C)cc1]

The compound 59 (70 mg, 0.17 mmol) is dissolved in 2 mL of DMF, under an inert atmosphere and in the presence of potassium carbonate (64 mg, 0.53 mmol), potassium iodide (31 mg, 0.19 mmol) and 2-naphthol (38 mg, 0.27 mmol). The reaction medium is heated to 65° C., for 22 hours, and then neutralized with water and extracted twice with ethyl acetate. The organic phases are combined, dried on magnesium sulfate, filtered and concentrated. The thereby obtained residue is purified by semi-preparative HPLC on a Waters Sunfire column (19×100 mm, 5 µm), with a flow of 20 mL/min and a 15 minute gradient of 10 to 100% acetonitrile in water (0.1% TFA buffer), in order to obtain the compound 60 (30 mg; 29%).

HPLC: RT=5.95 min, 99%

$^1$H NMR, dmso-d$_6$, δ (ppm) 2.26 (s, 3H); 2.90 (s, 3H); 4.03 (d, 2H); 4.10 (d, 2H); 6.92 (dd, 1H); 7.06 (d, 1H); 7.24 (d, 2H); 7.33 (t, 1H); 7.44 (t, 1H); 7.70-7.90 (m, 7H); 7.94-7.98 (m, 2H).

Mass spectrum (ESI+): m/z 500 (MH$^+$, 100%).

EXAMPLE 61

(4-(2-Phenoxy-ethoxy)-2-methyl-1,1-dioxo-2H-benzo[e][1,2]thiazin-3-yl)(naphthalen-2-yl)methanone

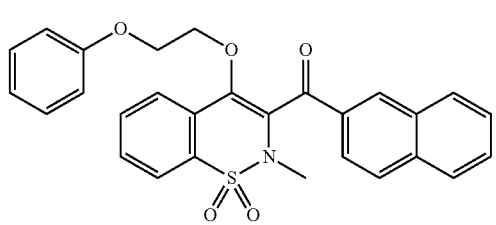 [SMILES: CN1C(C(=O)c2ccc3ccccc3c2)=C(OCCOc2ccccc2)c2ccccc2S1(=O)=O]

The compound 1 (100 mg, 0.274 mmol) is dissolved in 0.5 mL of DMF in presence of potassium carbonate (90 mg, 0.55 mmol) and 2-phenoxyethyl bromide (110 mg, 0.55 mmol). The reaction medium is heated in a sealed tube, to 80° C. for 16 hours. The medium is taken up in ethyl acetate and then washed with water and with a saturated NaCl solution. The organic phases are combined, dried on sodium sulfate, filtered and concentrated. The thereby obtained residue is purified on a column of 12 g of silica (flow rate 20 mL/min, gradient of 0 to 10% dichloromethane in heptane), in order to obtain the compound 61 as a yellow syrup (45 mg; 34%).

HPLC: RT=5.88 min, 98%

$^1$H NMR, dmso-$d_6$, δ (ppm) 2.97 (s, 3H); 3.85-3.87 (m, 2H); 4.01-4.05 (m, 2H); 6.59 (d, 2H); 6.82 (t, 1H); 7.11 (t, 2H); 7.62 (t, 1H); 7.71 (t, 1H); 7.83 (t, 1H); 7.88 (t, 1H); 7.91-8.04 (m, 6H); 8.62 (s, 1H).

Mass spectrum (ESI+): m/z 486 (MH$^+$, 100%).

EXAMPLE 62

Methyl 2-(2-methyl-3-(4-methylbenzoyl)-1,1-dioxo-2H-benzo[e][1,2]thiazin-4-yloxy)acetate

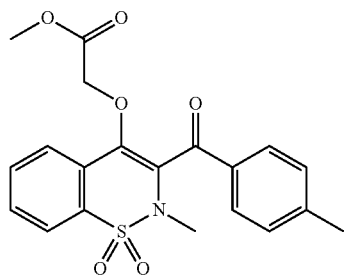 [SMILES: COC(=O)COC1=C(C(=O)c2ccc(C)cc2)N(C)S(=O)(=O)c2ccccc21]

The compound 62 was synthesized according to the same procedure as the compound 59 from the compound 3 (300 mg, 0.91 mmol) and from methyl glycolate (350 μl, 4.5 mmol) in order to obtain 300 mg (79%) of the desired product as a yellow syrup.

HPLC: RT=4.97 min, 97%

$^1$H NMR, dmso-$d_6$, δ (ppm): 2.42 (s, 3H); 2.88 (s, 3H); 3.47 (s, 3H); 4.42 (s, 2H); 7.40 (d, 2H,); 7.75-7.98 (m, 6H).

Mass spectrum (ESI+): m/z 402 (MH$^+$, 100%); 419 (MNH$_4^+$, 42%).

EXAMPLE 63

(2-Methyl-3-(4-methylbenzoyl)-1,1-dioxo-2H-benzo[e][1,2]thiazin-4-yloxy)acetic acid

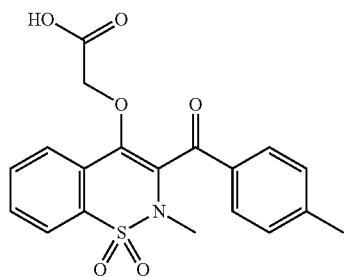 [SMILES: Cc1ccc(C(=O)C2=C(OCC(=O)O)c3ccccc3S(=O)(=O)N2C)cc1]

The compound 62 (75 mg, 0.18 mmol) is dissolved in 1 mL of THF, and lithium hydroxide (1M/H$_2$O, 0.37 mmol) is added. The reaction medium is stirred at room temperature for 2 hours, and then diluted in water and extracted twice with dichloromethane. The organic phases are combined, dried on magnesium sulfate, filtered and concentrated in order to obtain 22 mg of the desired product (HPLC: RT=4.55 min, 97%). The yield of this operation is 30%.

$^1$H NMR, dmso-$d_6$, δ (ppm) 2.41 (s, 3H); 2.88 (s, 3H); 4.28 (s, 2H); 7.39 (d, 2H); 7.81 (t, 1H); 7.85-7.95 (m, 5H); 12.96 (se, 1H, exch.).

Mass spectrum (ESI+): m/z 388 (MH$^+$, 100%); 405 (MNH$_4^+$, 54%

EXAMPLES 64 TO 66

The compound 63 (110 mg, 0.28 mmol) is dissolved in 3 mL of DMF. Different amines (0.23 mmol), DIEA (82 μl, 0.472 mmol), HOOBT (35 mg, 0.26 mmol) EDCI (50 mg, 0.26 mmol) are added. The reaction medium is stirred for 18 hours at room temperature. The medium is taken up in dichloromethane and then washed with 1N soda, water, and a saturated NaCl solution. The organic phases are combined, dried on magnesium sulfate, filtered and concentrated. The thereby obtained residues are purified on columns of 12 g of spherical silica (flow rate 12 mL/min, 0 to 50% AcOEt in heptane), in order to obtain the desired products.

| Ex. | R1R2N | Name of the compounds | HPLC | Yld | Mass MNH$_4^+$ |
|---|---|---|---|---|---|
| 64 | Naphthalen-1-yl | 2-(2-methyl-3-(4-methylbenzoyl)-1,1-dioxo-2H-benzo[e][1,2]thiazin-4-yloxy)-N-(naphthalen-1-yl)acetamide | 5.45' 95% | 40% | 530 |
| 65 | Adamantan-1-yl | 2-(2-methyl-3-(4-methylbenzoyl)-1,1-dioxo-2H-benzo[e][1,2]thiazin-4-yloxy)-N-(adamantan-1-yl)acetamide | 5.90' 99% | 72% | 538 |
| 66 | Adamantan-2-yl | 2-(2-methyl-3-(4-methylbenzoyl)-1,1-dioxo-2H-benzo[e][1,2]thiazin-4-yloxy)-N-(adamantan-2-yl)acetamide | 5.83' 99% | 85% | 538 |

* $^1$H NMR, dmso-$d_6$, Ex. 64: 2.33 (s, 3 H); 2.93 (s, 3 H); 4.55 (s, 2 H); 7.35 (d, 2 H); 7.43-7.55 (m, 4 H); 7.76 (d, 1 H); 7.82-7.85 (m, 2 H); 7.91-7.99 (m, 5 H); 8.12 (d, 1 H); 7.76 (s, 1 H, exch). 65: 1.51-1.59 (m, 6 H); 1.71 (s, 6 H); 1.94 (s, 3 H); 2.41 (s, 3 H); 2.88 (s, 3 H); 4.05 (s, 2 H); 6.78 (s, 1 H); 7.42 (s, 2 H); 7.81 (t, 1 H); 7.87-7.95 (m, 4 H); 7.99 (d, 1 H). 66: 1.39-1.41 (m, 2 H); 1.64-1.77 (m, 12 H); 2.41 (s, 3 H); 2.88 (s, 3 H); 3.65-3.75 (m, 1 H); 4.21 (s, 2 H); 7.39 (d, 3 H); 7.81 (t, 1 H); 7.87-7.95 (m, 4 H); 8.0 (d, 1 H).

EXAMPLE 67

Methyl 2-(2-methyl-3-(4-methylbenzoyl)-1,1-dioxo-2H-benzo[e][1,2]thiazin-4-yloxy)acetate

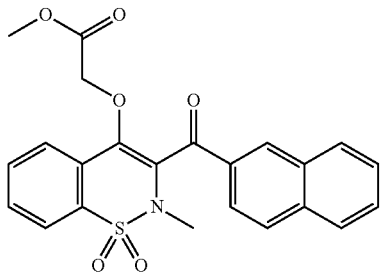 [SMILES: COC(=O)COC1=C(C(=O)c2ccc3ccccc3c2)N(C)S(=O)(=O)c2ccccc21]

The compound 1 (1.0 g, 2.74 mmol) is dissolved in 2 mL of DMF in the presence of potassium carbonate (682 mg, 4.1 mmol) and methyl bromoacetate (1.26 mL, 13.68 mmol). The reaction medium is stirred at room temperature for 5 hours and then the same amount of methyl bromoacetate is added again. After one night at room temperature, the mixture is taken up in ethyl acetate and then washed with water and with a saturated NaCl solution. The organic phases are combined, dried on sodium sulfate, filtered and concentrated. The thereby obtained residue is purified on a column of 90 g of silica (flow rate 32 mL/min, gradient of 40 to 100% dichloromethane in heptane), in order to obtain the compound 67 as a yellow syrup (486 mg; 41%).

HPLC: RT=5.23 min, 86%

$^1$H NMR, dmso-d$_6$, δ (ppm) 2.95 (s, 3H); 3.39 (s, 3H); 4.45 (s, 2H); 7.64 (t, 1H); 7.72 (t, 1H); 7.81-7.89 (m, 1H); 7.93 (d, 2H); 7.97 (d, 1H); 7.99-8.11 (m, 4H); 8.66 (s, 1H).

Mass spectrum (ESI+): m/z 438 (MH$^+$, 100%).

EXAMPLE 68

2-(2-methyl-3-(4-methylbenzoyl)-1,1-dioxo-2H-benzo[e][1,2]thiazin-4-yloxy)acetic acid

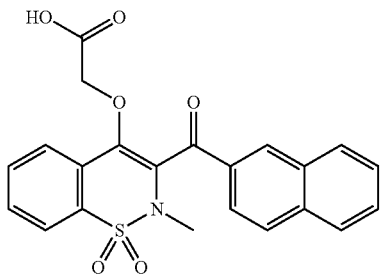 [SMILES: CN1C(C(=O)c2ccc3ccccc3c2)=C(OCC(=O)O)c2ccccc2S1(=O)=O]

The compound 67 (480 mg, 1.1 mmol) is dissolved in THF/water 5:1 mixture (6 mL) and then treated with LiOH (103 mg, 4.39 mmol) at room temperature for 15 minutes. The medium is taken up in ethyl acetate and then washed with 1N HCl, water and with a saturated NaCl solution. The organic phases are combined, dried on sodium sulfate, filtered and concentrated. The thereby obtained residue is purified on a column of 30 g of silica (dichloromethane/methanol/acetic acid 95/4.5/0 eluent), in order to obtain the compound 68 as a yellow foam (321 mg; 69%).

HPLC: RT=4.86 min, 99%

$^1$H NMR, dmso-d$_6$, δ (ppm) 2.93 (s, 3H); 4.29 (s, 2H); 7.64 (t, 1H); 7.72 (t, 1H); 7.83 (t, 1H); 7.89-8.09 (m, 7H); 8.66 (s, 1H).

Mass spectrum (ESI+): m/z 424 (MH$^+$, 100%).

EXAMPLES 69 TO 71

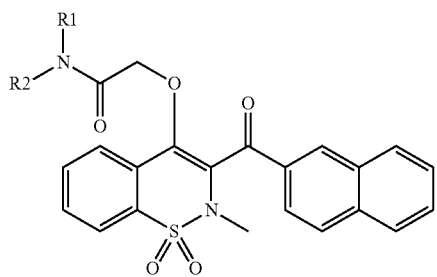

The compounds 69 to 71 were prepared according to the following procedure:

The compound 1 (100 mg, 0.23 mmol) is dissolved in 1.5 mL of dichloromethane. Different amines (0.23 mmol), DIEA (82 μl, 0.472 mmol), HOOBT (35 mg, 0.26 mmol) and EDCI (50 mg, 0.26 mmol) are added. The reaction mixture is stirred for 24 hours at room temperature and then amine in excess is added (0.07 mmol) and the medium is stirred for a further 5 hours. The medium is taken up in dichloromethane and washed with 1N soda, water and with a saturated NaCl solution. The organic phases are combined, dried on sodium sulfate, filtered and concentrated. The thereby obtained residues are purified on columns of 12 g of spherical silica (flow rate 12 mL/min, 1% of a methanol/ammonia 9:1 mixture in dichloromethane), in order to obtain the desired products.

| Ex. | NR$_1$R$_2$ | Name of the compounds | HPLC | Yld | Mass MH$^+$ |
|---|---|---|---|---|---|
| 69 | piperidine | 2-[2-Methyl-3-(naphthalene-2-carbonyl)-1,1-dioxo-2H-benzo[e][1,2]thiazin-4-yloxy]-1-piperidin-1-yl-ethanone | 5.26' 98% | 49% | 491 |
| 70 | 4-methylpiperazine | 2-[2-Methyl-3-(naphthalene-2-carbonyl)-1,1-dioxo-2H-benzo[e][1,2]thiazin-4-yloxy]-1-(4-methyl-piperazin-1-yl)-ethanone | 3.93' 98% | 47% | 506 |

| Ex. | NR₁R₂ | Name of the compounds | HPLC | Yld | Mass MH⁺ |
|---|---|---|---|---|---|
| 71 | (4-benzylpiperazin-1-yl) | 1-(4-Benzyl-piperazin-1-yl)-2-[2-methyl-3-(naphthalene-2-carbonyl)-1,1-dioxo-2H-benzo[e][1,2]thiazin-4-yloxy]-ethanone | 4.28' | 20% 98% | 582 |

*¹H NMR, dmso-d₆, Ex. 69: 1.08-1.31 (m, 6 H); 2.87 (t, 2 H); 2.95 (s, 3 H); 3.04 (t, 2 H); 4.41 (s, 2 H); 7.64 (t, 1 H); 7.72 (t, 1 H); 7.84 (m, 1 H); 7.92 (d, 2 H); 7.97-8.10 (m, 5 H); 8.65 (s, 1 H). Ex. 70: 1.85 (t, 2 H): 1.92 (t, 2 H); 1.95 (s, 3 H); 2.94 (broad s, 5 H); 3.04 (broad s, 2 H); 4.44 (s, 2 H); 7.64 (t, 1 H); 7.72 (t, 1 H); 7.84 (m, 1 H); 7.92 (m, 2 H); 7.97-8.10 (m, 5 H); 8.65 (s, 1 H). Ex. 71: 1.88 (broad s, 2 H); 1.96 (broad s, 2 H); 2.92 (m, 5 H); 3.08 (broad s, 2 H); 3.22 (s, 2 H); 4.42 (s, 2 H); 7.16 (d, 2 H); 7.21-7.31 (m, 3 H); 7.63 (t, 1 H); 7.72 (t, 1 H); 7.82 (m, 1 H); 7.78 (m, 2 H); 7.97-8.09 (m, 5 H); 8.65 (s, 1 H).

EXAMPLES 72 TO 74

The compounds 72 to 74 were synthesized according to the procedure described for preparing the compound 46, from the compound 1 and from various acid chlorides.

| Ex. | R | Name of the compounds | HPLC | Yld. | Mass MNH₄⁺ |
|---|---|---|---|---|---|
| 72 | 4-chloro-phenyl-oxy-acetyl | (4-Chloro-phenoxy)-acetic acid 2-methyl-3-(naphthalene-2-carbonyl)-1,1-dioxo-2H-benzo[e][1,2]thiazin-4-yl ester | 6.02' | 77% 94% | 551 |
| 73 | Naphthalen-1-yloxy-acetyl | (Naphthalen-1-yloxy)-acetic acid 2-methyl-3-(naphthalene-2-carbonyl)-1,1-dioxo-2H-benzo[e][1,2]thiazin-4-yl ester | 6.16' | 84% 98% | 567 |
| 74 | Naphthalen-2-yloxy-acetyl | (Naphthalen-2-yloxy)-acetic acid 2-methyl-3-(naphthalene-2-carbonyl)-1,1-dioxo-2H-benzo[e][1,2]thiazin-4-yl ester | 6.11' | 83% 96% | 567 |

*¹H NMR, dmso-d₆, Ex. 72: 3.04 (s, 3 H); 4.94 (s, 2 H); 6.67 (d, 2 H); 7.07 (d, 2 H); 7.64 (t, 1 H); 7.72 (t, 1 H); 7.84-7.93 (m, 3 H); 8.02 (m, 3 H); 8.08 (d, 1 H); 8.14 (d, 1 H); 8.69 (s, 1 H). Ex. 73: 3.05 (s, 3 H); 5.10 (s, 2 H); 6.59 (d, 1 H); 7.12 (t, 1 H); 7.38-7.41 (m, 2 H); 7.49 (t, 1 H); 7.66 (t, 1 H); 7.75 (t, 1 H); 7.81-7.90 (m, 4 H); 7.98 (d, 1 H); 8.02-8.08 (m, 4 H); 8.13 (d, 1 H); 8.72 (s, 1 H). Ex. 74: 3.02 (s, 3 H); 5.07 (s, 2 H); 7.01 (dd, 1 H); 7.12 (d, 1 H); 7.32-7.41 (m, 2 H); 7.57 (d, 1 H); 7.63 (t, 1 H); 7.70-7.79 (m, 3 H); 7.85-7.94 (m, 3 H); 8.02-8.12 (m, 5 H); 8.71 (s, 1 H).

EXAMPLES 75 AND 76

The compounds 75 and 76 were synthesized according to the procedure described for preparing the compound 60, from the compound 59 and various alcohols.

| Ex. | R | Name of the compounds | HPLC | Yld. | Mass MH⁺ |
|---|---|---|---|---|---|
| 75 | Naphthalen-1-yl | (4-[2-(naphthalen-1-yloxy)ethoxy]-2-methyl-1,1-dioxo-2H-benzo[e][1,2]thiazin-3-yl)(p-tolyl) methanone | 6.00' | 38% 97% | 500 |
| 76 | 4-Chlorophenyl | (4-[2-(4-chlorophenyl-oxy)ethoxy]-2-methyl-1,1-dioxo-2H-benzo[e][1,2]thiazin-3-yl)(p-tolyl) methanone | 5.87' | 48% 98% | 484 |

*¹H NMR, dmso-d₆, Ex. 75: 2.31 (s, 3 H); 2.90 (s, 3 H); 4.10-4.20 (m, 4 H); 6.75 (d, 1 H); 7.21 (d, 2 H); 7.33 (t, 1 H); 7.40-7.44 (m, 2 H); 7.51 (t, 1 H); 7.78-7.85 (m, 6 H); 7.97 (t, 2 H). Ex. 76: 2.37 (s, 3 H); 2.89 (s, 3 H); 3.85-3.95 (m, 2 H); 4.00-4.05 (m, 2 H); 6.69 (d, 2 H); 7.23 (d, 2 H); 7.29 (d, 2 H); 7.78-7.96 (m, 6 H).

EXAMPLES 77 AND 78

The compounds 77 and 78 were synthesized according to the procedure described for preparing the compound 34, from the compound 3 and from acetyl chloride and propanoyl chloride respectively.

| Ex. | R | Name of the compounds | HPLC | Yld. | MNH₄⁺ |
|---|---|---|---|---|---|
| 77 | Methyl | Acetic acid 2-methyl-3-(4-methylbenzoyl)-1,1-dioxo-2H-benzo[e][1,2]thiazin-4-yl ester | 5.05' | 81% 99% | 389 |

-continued

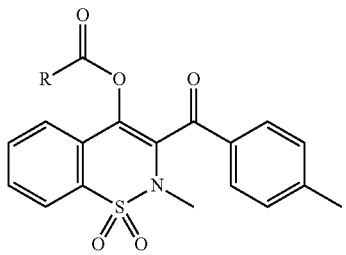

| Ex. | R | Name of the compounds | HPLC | Yld. | MNH₄⁺ |
|---|---|---|---|---|---|
| 78 | Ethyl | Propanoic acid 2-methyl-3-(4-methylbenzoyl)-1,1-dioxo-2H-benzo[e][1,2]thiazin-4-yl ester | 5.25' | 88% | 403 |
|  |  |  | 99% |  |  |

*¹H NMR, dmso-d₆, Ex. 77: 2.04 (s, 3 H); 2.42 (s, 3 H); 2.98 (s, 3 H); 7.42 (d, 2 H); 7.76-7.90 (m, 5 H); 7.98 (d, 1 H). Ex. 78: 0.86 (t, 3 H); 2.33 (q, 2 H); 2.42 (s, 3 H); 2.99 (s, 3 H); 7.41 (d, 2 H); 7.73 (d, 1 H); 7.79-7.89 (m, 4 H); 7.98 (d, 1 H).

EXAMPLES 79 AND 80

The compounds 79 et 80 were synthesized according to the procedure described for preparing the compound 59, from the compound 3 and from methanol and ethanol respectively.

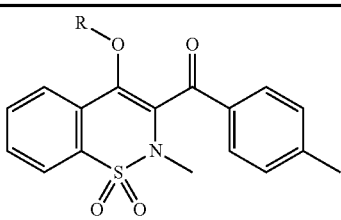

| Ex. | R | Name of the compounds | HPLC | Yld. | Mass MH⁺ |
|---|---|---|---|---|---|
| 79 | Methyl | (4-methyloxy-2-methyl-1,1-dioxo-benzo[e][1,2]thiazin-3-yl)(p-tolyl)methanone | 5.13' 98% | 58% | 344 |
| 80 | Ethyl | (4-ethyloxy-2-methyl-1,1-dioxo-2H-benzo[e][1,2]thiazin-3-yl)(p-tolyl)methanone | 5.29' 99% | 63% | 358 |

*¹H NMR, dmso-d₆, Ex. 79: 2.42 (s, 3 H); 2.91 (s, 3 H); 3.50 (s, 3 H); 7.41 (d, 2 H); 7.78-7.95 (m, 6 H). Ex. 80: 0.93 (t, 3 H); 2.41 (s, 3 H); 2.90 (s, 3 H); 3.73 (q, 2 H); 7.40 (d, 2 H); 7.78-7.94 (m, 6 H).

EXAMPLE 81

[4-(2-Bromo-ethoxy)-2-methyl-1,1-dioxo-2H-benzo[e][1,2]thiazin-3-yl]-naphthalen-2-yl-methanone

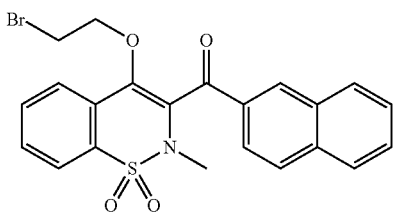 [SMILES: CN1C(C(=O)c2ccc3ccccc3c2)=C(OCCBr)c2ccccc2S1(=O)=O]

The compound 1 (150 mg, 0.41 mmol) is dissolved in methylethylketone (3 mL) and then treated with dibromoethane (71 µl, 0.82 mmol) in the presence of K₂CO₃ (170 mg, 1.02 mmol). The reaction is heated with microwave energy in a sealed tube at 130° C. for 4 h 30 min. The medium is taken up in ethyl acetate and then washed with water and with a saturated NaCl solution. The organic phases are combined, dried on sodium sulfate, filtered and concentrated. The thereby obtained residue (brown syrup, 197 mg) is directly engaged into the next reaction.

EXAMPLE 82

{4-[2-(4-Chloro-phenoxy)-ethoxy]-2-methyl-1,1-dioxo-2H-benzo[e][1,2]thiazin-3-yl}-naphthalen-2-yl-methanone

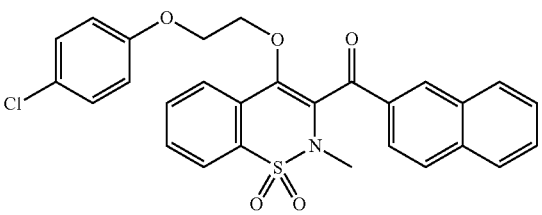 [SMILES: CN1C(C(=O)c2ccc3ccccc3c2)=C(OCCOc2ccc(Cl)cc2)c2ccccc2S1(=O)=O]

The compound 81 (197 mg, 0.41 mmol) is dissolved in methylethylketone (1.5 mL) and then treated with 4-chlorophenol (107 µl, 0.82 mmol) in the presence of K₂CO₃ (173 mg, 1.04 mmol). The reaction is heated with microwave energy in a sealed tube at 130° C. for 2 hours. The medium is taken up in ethyl acetate and then washed with water and with a saturated NaCl solution. The organic phases are combined, dried on sodium sulfate, filtered and concentrated. The thereby obtained residue is purified on a column of 12 g of silica (flow rate 12 mL/min, gradient of 10 to 100% dichloromethane in heptane), in order to obtain the compound 82 as a yellow syrup (21 mg; 14%).

HPLC: RT=6.10 min, 89%

¹H NMR, dmso-d₆, δ (ppm) 2.96 (s, 3H); 3.85 (m, 2H); 3.97 (m, 2H); 6.57 (d, 2H); 7.08 (d, 2H); 7.61 (t, 1H); 7.70 (t, 1H); 7.83 (t, 1H); 7.89-8.02 (m, 7H); 8.60 (s, 1H).

Mass spectrum (ESI+): m/z 520 (MH⁺, 66%).

EXAMPLE 83

Carbonic acid ethyl ester 1-[2-methyl-3-(naphthalene-2-carbonyl)-1,1-dioxo-2H-benzo[e][1,2]thiazin-4-yloxy]-ethyl ester

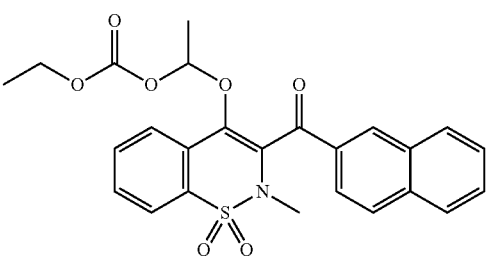 [SMILES: CCOC(=O)OC(C)OC1=C(C(=O)c2ccc3ccccc3c2)N(C)S(=O)(=O)c2ccccc21]

The compound 1 (100 mg, 0.27 mmol) is dissolved in DMF (1 mL) and then treated with ethyl 2-chloropropanoate (110 µl, 0.82 mmol) in the presence of K₂CO₃ (91 mg, 0.55 mmol). The reaction is heated in a sealed to 60° C. overnight and then the same amount of ethyl 2-chloropropanoate is added and the reaction is stirred for a further 24 hours. The medium is taken up into ethyl acetate and then washed with water and with a saturated NaCl solution. The organic phases are combined, dried on sodium sulfate, filtered and concentrated. The thereby obtained residue is purified on a column of 12 g of silica (flow rate 12 mL/min, gradient of 25 to 80% dichloromethane in heptane), in order to obtain the compound 83 as a yellow syrup (100 mg; 76%).

HPLC: RT=5.55 min, 97%

$^1$H NMR, dmso-d$_6$, δ (ppm) 0.94 (t, 3H); 1.25 (d, 3H); 2.94 (s, 3H); 3.80-3.93 (m, 2H); 5.99 (q, 1H); 7.65 (t, 1H); 7.73 (t, 1H); 7.85 (m, 1H); 7.90 (d, 2H); 7.97 (d, 1H); 8.01-8.11 (m, 4H); 8.69 (s, 1H).

Mass spectrum (ESI+): m/z 504 (MNa$^+$, 100%).

EXAMPLE 84

[2-Methyl-1,1-dioxo-4-(2-piperidin-1-yl-ethoxy)-1,2-dihydro-2H-benzo[e][1,2]thiazin-3-yl]-naphthalen-2-yl-methanone

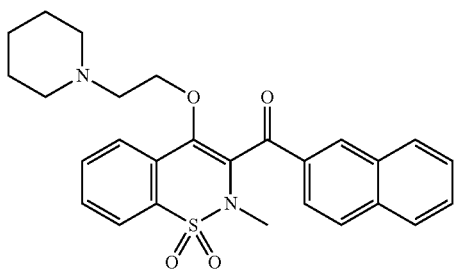 [SMILES: CN1C(C(=O)c2ccc3ccccc3c2)=C(OCCN2CCCCC2)c2ccccc2S1(=O)=O]

The compound 1 (100 mg, 0.27 mmol) is dissolved in methylethylketone (0.5 mL) and then treated with 1-(2-chloroethyl)piperidine (252 mg, 1.37 mmol) in the presence of K$_2$CO$_3$ (159 mg, 0.96 mmol). The reaction is heated to 80° C. overnight. The medium is further taken up with ethyl acetate and then washed with water and with a saturated NaCl solution. The organic phases are combined, dried on sodium sulfate, filtered and concentrated. The thereby obtained residue is purified on a 12 g silica column (flow rate 12 mL/min, dichloromethane/MeOH/NH$_4$OH 99/09/01), in order to obtain the compound 84 as a yellow syrup (50 mg; 43%).

HPLC: RT=4.17 min, 92%

$^1$H NMR, dmso-d$_6$, δ (ppm): 1.21 (broad s, 6H); 1.99 (broad s, 4H); 2.19 (t, 2H); 2.98 (s, 3H); 3.72 (t, 2H); 7.64 (t, 1H); 7.72 (t, 1H); 7.83 (t, 1H); 7.90 (t, 1H); 7.97 (d, 1H); 8.01-8.11 (m, 5H); 8.66 (s, 1H).

Mass spectrum (ESI+): m/z 477 (MH$^+$, 100%).

EXAMPLES 85 TO 96

The compounds 85 to 96 were synthesized according to the following procedure:

The compounds 13, 15, or 17 (100 mg) are dissolved under an inert atmosphere in 2 mL of dichloromethane in the presence or triethylamine (6 eq.) and then treated with various acid chlorides (4 eq.) at 0° C. The reaction mixtures are stirred for 2 hours at 0° C. and then at room temperature for 20 hours. The media are taken up in ethyl acetate and then washed with water and with a saturated NaCl solution. The organic phases are combined, dried on sodium sulfate, filtered and concentrated. The thereby obtained residues are purified on a column of 12 g of silica (flow rate 12 mL/min, gradient of 0 to 20% ethyl acetate in heptane), in order to obtain the expected compounds.

| Ex. | R1 | R2 | Name of the compounds | HPLC | Yld. | Mass MH$^+$/MNa$^+$ |
|---|---|---|---|---|---|---|
| 85 | 4-chlorophenyl | 5-Cl | 4-Chloro-benzoic acid 5-chloro-2-methyl-3-(naphthalene-2-carbonyl)-1,1-dioxo-2H-benzo[e][1,2]thiazin-4-yl ester | 6.43' | 29% 96% | 555 |
| 86 | Cyclohexyl | 5-Cl | Cyclohexanecarboxylic acid 5-chloro-2-methyl-3-(naphthalene-2-carbonyl)-1,1-dioxo-2H-benzo[e][1,2]thiazin-4-yl ester | 6.50' | 26% 98% | 527 |
| 87 | Phenyl | 5-Cl | Benzoic acid 5-chloro-2-methyl-3-(naphthalene-2-carbonyl)-1,1-dioxo-2H-benzo[e][1,2]thiazin-4-yl ester | 6.11' | 65% 92% | 521 |
| 88 | 4-Chlorophenyl | 6-F | 4-Chloro-benzoic acid 6-fluoro-2-methyl-3-(naphthalene-2-carbonyl)-1,1-dioxo-2H-benzo[e][1,2]thiazin-4-yl ester | 6.30' | 40% 99% | 539 |
| 89 | Cyclohexyl | 6-F | Cyclohexanecarboxylic acid 6-fluoro-2-methyl-3-(naphthalene-2-carbonyl)-1,1-dioxo-2H-benzo[e][1,2]thiazin-4-yl ester | 6.30' | 55% 97% | 511 |
| 90 | Phenyl | 6-F | Benzoic acid 6-fluoro-2-methyl-3-(naphthalene-2-carbonyl)-1,1-dioxo-2H-benzo[e][1,2]thiazin-4-yl ester | 5.90' | 50% 94% | 505 |
| 91 | 4-chlorophenyl | 7-F | 4-Chloro-benzoic acid 7-fluoro-2-methyl-3-(naphthalene-2-carbonyl)-1,1-dioxo-2H-benzo[e][1,2]thiazin-4-yl ester | 6.20' | 60% 98% | 539 |
| 92 | Cyclohexyl | 7-F | Cyclohexanecarboxylic acid 7-fluoro-2-methyl-3-(naphthalene-2-carbonyl)-1,1-dioxo-2H-benzo[e][1,2]thiazin-4-yl ester | 6.37' | 19% 98% | 511 |
| 93 | Phenyl | 7-F | Benzoic acid 7-fluoro-2-methyl-3-(naphthalene-2-carbonyl)-1,1-dioxo-2H-benzo[e][1,2]thiazin-4-yl ester | 5.91' | 69% 93% | 505 |
| 94 | Methyl | 7-F | Acetic acid 7-fluoro-2-methyl-3-(naphthalene-2-carbonyl)-1,1-dioxo-2H-benzo[e][1,2]thiazin-4-yl ester | 5.46' | 62% 97% | 448 |
| 95 | Phenoxymethyl | 7-F | Phenoxy-acetic acid 7-fluoro-2-methyl-3-(naphthalene-2-carbonyl)-1,1-dioxo-2H-benzo[e][1,2]thiazin-4-yl ester | 5.89' | 50% 92% | 540 |

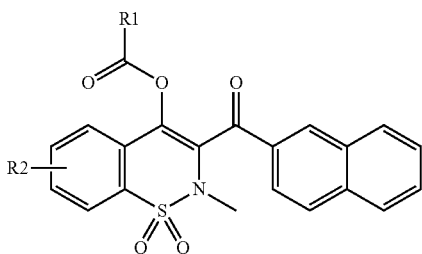

| Ex. | R1 | R2 | Name of the compounds | HPLC | Yld. | Mass MH+/ MNa+ |
|---|---|---|---|---|---|---|
| 96 | 4-Cl-phenoxy-methyl | 7-F | (4-Chloro-phenoxy)-acetic acid 7-fluoro-2-methyl-3-(naphthalene-2-carbonyl)-1,1-dioxo-2H-benzo[e][1,2]thiazin-4-yl ester | 6.10' 93% | 18% | 574 |

EXAMPLES 97 TO 104

The compounds 97 to 104 were synthesized according to the procedure used for preparing examples 56 to 58 from the compound 13, 15, or 17 and from corresponding alkyl iodides or sulfates.

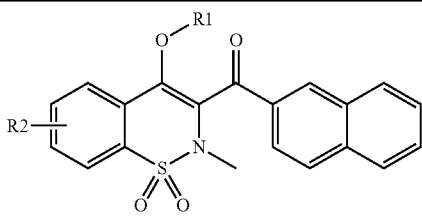

| Ex. | R1 | R2 | Name of the compounds | HPLC | Yld. | Mass MH+/ MNH4+ |
|---|---|---|---|---|---|---|
| 97 | Ethyl | 5-Cl | (5-Chloro-4-ethoxy-2-methyl-1,1-dioxo-2H-benzo[e][1,2]thiazin-3-yl)-naphthalen-2-yl-methanone | 5.61' 97% | 11% | 428 |
| 98 | Propyl | 5-Cl | (5-Chloro-4-propoxy-2-methyl-1,1-dioxo-2H-benzo[e][1,2]thiazin-3-yl)-naphthalen-2-yl-methanone | 6.02' 96% | 44% | 442 |
| 99 | Methyl | 6-F | (6-Fluoro-4-methoxy-2-methyl-1,1-dioxo-2H-benzo[e][1,2]thiazin-3-yl)-naphthalen-2-yl-methanone | 5.65' 93% | 34% | 398 |
| 100 | Ethyl | 6-F | (6-Fluoro-4-ethoxy-2-methyl-1,1-dioxo-2H-benzo[e][1,2]thiazin-3-yl)-naphthalen-2-yl-methanone | 5.72' 97% | 52% | 429 |
| 101 | Propyl | 6-F | (6-Fluoro-4-propoxy-2-methyl-1,1-dioxo-2H-benzo[e][1,2]thiazin-3-yl)-naphthalen-2-yl-methanone | 5.92' 97% | 56% | 426 |

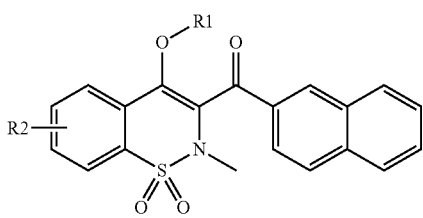

| Ex. | R1 | R2 | Name of the compounds | HPLC | Yld. | Mass MH+/ MNH4+ |
|---|---|---|---|---|---|---|
| 102 | Methyl | 7-F | (7-Fluoro-4-methoxy-2-methyl-1,1-dioxo-2H-benzo[e][1,2]thiazin-3-yl)-naphthalen-2-yl-methanone | 5.56' 97% | 20% | 398 |
| 103 | Ethyl | 7-F | (7-Fluoro-4-ethoxy-2-methyl-1,1-dioxo-2H-benzo[e][1,2]thiazin-3-yl)-naphthalen-2-yl-methanone | 5.77' 95% | 47% | 412 |
| 104 | Propyl | 7-F | (7-Fluoro-4-propoxy-2-methyl-1,1-dioxo-2H-benzo[e][1,2]thiazin-3-yl)-naphthalen-2-yl-methanone | 5.90' 98% | 52% | 426 |

EXAMPLE 105

[7-Fluoro-2-methyl-3-(naphthalene-2-carbonyl)-1,1-dioxo-2H-benzo[e][1,2]thiazin-4-yloxy]-acetic acid methyl ester

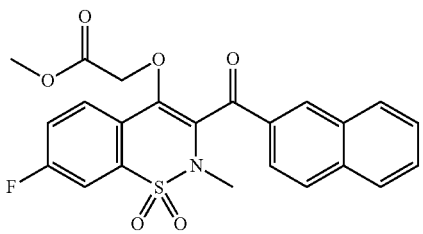 [SMILES: COC(=O)COC1=C(C(=O)c2ccc3ccccc3c2)N(C)S(=O)(=O)c2cc(F)ccc21]

The compound 105 was synthesized according to the procedure used for preparing example 67 from the compound 17 (1 g, 2.61 mmol). The product is obtained as a yellow syrup (810 mg; 68%).

HPLC: RT=5.37 min, 95%

$^1$H NMR, dmso-$d_6$, δ (ppm): 2.95 (s, 3H); 3.40 (s, 3H); 4.45 (s, 2H); 7.64 (t, 1H); 7.70 (t, 1H); 7.80 (dt, 1H); 7.91 (dd, 1H); 7.99-8.10 (m, 5H); 8.65 (s, 1H).

Mass spectrum (ESI+): m/z 456 (MH+, 100%).

EXAMPLE 106

[7-Fluoro-2-methyl-3-(naphthalene-2-carbonyl)-1,1-dioxo-2H-benzo[e][1,2]thiazin-4-yloxy]-acetic acid methyl ester

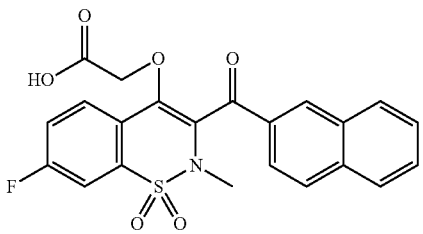 [SMILES: CN1C(C(=O)c2ccc3ccccc3c2)=C(OCC(=O)O)c2ccc(F)cc2S1(=O)=O]

The compound 106 was synthesized according to the procedure used for preparing example 68 from the compound 105 (598 mg, 1.31 mmol). The product is obtained as a beige powder (262 mg; 45%).

HPLC: RT=4.92 min, 97%

Mass spectrum (ESI+): m/z 442 (MH$^+$, 100%).

EXAMPLES 107 TO 109

The compounds 107 to 109 were synthesized according to the procedure used for preparing examples 69 to 71 from the compound 106 and the corresponding amines.

EXAMPLE 110

Benzenesulfonic acid 7-fluoro-2-methyl-3-(naphthalene-2-carbonyl)-1,1-dioxo-2H-benzo[e][1,2]thiazin-4-yl ester

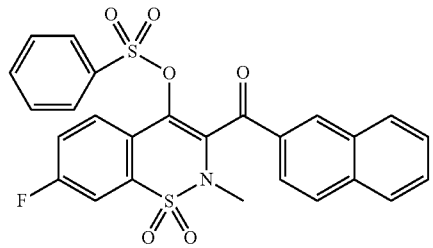 [SMILES: CN1C(C(=O)c2ccc3ccccc3c2)=C(OS(=O)(=O)c2ccccc2)c2ccc(F)cc2S1(=O)=O]

The compound 17 (200 mg, 0.52 mmol) is dissolved in dichloromethane (2 mL) and then treated at 0° C. with benzene sulfonyl chloride (67 µl, 0.52 mmol) in the presence of Et$_3$N (145 µl, 1.04 mmol). The reaction is stirred from 0° C. to room temperature for 4 hours and then the medium is taken up in dichloromethane and washed with water and with a saturated NaCl solution. The organic phases are combined, dried on magnesium sulfate, filtered and concentrated. The thereby obtained residue is purified on a column of 12 g of silica (flow rate 12 mL/min, gradient of 20 to 50% dichloromethane in heptane), in order to obtain the compound 110 as a cream-colored powder (177 mg; 65%).

HPLC: RT=5.72 min, 94%

$^1$H NMR, dmso-d$_6$, δ (ppm): 2.98 (s, 3H); 7.40 (t, 2H); 7.54-7.61 (m, 4H); 7.66 (t, 1H); 7.75 (m, 2H); 7.84-7.90 (m, 2H); 8.04-8.09 (m, 3H); 8.57 (s, 1H).

Mass spectrum (ESI+): m/z 541 (MNH$_4^+$, 100%).

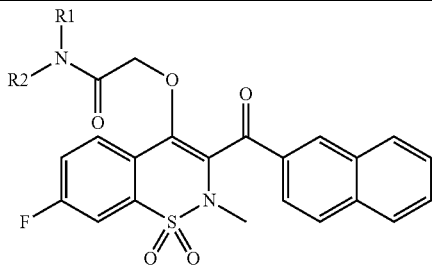

| Ex. | NR$_1$R$_2$ | Name of the compounds | HPLC | Yld. | Mass MH$^+$ |
|---|---|---|---|---|---|
| 107 | piperidine | 2-[7-Fluoro-2-methyl-3-(naphthalene-2-carbonyl)-1,1-dioxo-2H-benzo[e][1,2]thiazin-4-yloxy]-1-piperidin-1-yl-ethanone | 5.40' | 64% | 509 |
|  |  |  | 91% |  |  |
| 108 | 4-methyl-piperazine | 2-[7-Fluoro-2-methyl-3-(naphthalene-2-carbonyl)-1,1-dioxo-2H-benzo[e][1,2]thiazin-4-yloxy]-1-(4-methyl-piperazin-1-yl)-ethanone | 3.99' | 67% | 524 |
|  |  |  | 99% |  |  |
| 109 | 4-benzyl-piperazine | 1-(4-Benzyl-piperazin-1-yl)-2-[7-fluoro-2-methyl-3-(naphthalene-2-carbonyl)-1,1-dioxo-2H-benzo[e][1,2]thiazin-4-yloxy]-ethanone | 4.35' | 69% | 600 |
|  |  |  | 98% |  |  |

*$^1$H NMR, dmso-d$_6$, Ex. 107: 1.09-1.14 (m, 4 H); 1.31 (m, 2 H); 2.87 (t, 2 H); 2.95 (s, 3 H); 3.05 (t, 2 H); 4.41 (s, 2 H); 7.64 (t, 1 H); 7.72 (t, 1 H); 7.79 (dt, 1 H); 7.89 (dd, 1 H); 7.99-8.10 (m, 5 H); 8.64 (s, 1 H). Ex. 108: 1.86 (t, 2 H); 1.92 (t, 2 H); 1.96 (s, 3 H); 2.92-2.95 (m, 5 H); 3.05 (t, 2 H); 4.44 (s, 2 H); 7.64 (t, 1 H); 7.72 (t, 1 H); 7.79 (dt, 1 H); 7.90 (dd, 1 H); 7.98-8.10 (m, 5 H); 8.64 (s, 1 H). Ex. 109: 1.90 (broad s, 2 H); 1.97 (broad s, 2 H); 2.92 (broad s, 2 H); 2.95 (s, 3 H); 3.09 (broad s, 2 H); 3.22 (s, 2 H); 4.43 (s, 2 H); 7.16 (d, 2 H); 7.21-7.31 (m, 3 H); 7.64 (t, 1 H); 7.72 (t, 1 H); 7.80 (dt, 1 H); 7.90 (dd, 1 H); 7.98-8.09 (m, 5 H); 8.64 (s, 1 H).

EXAMPLES 111 TO 117

The compounds 111 to 117 were synthesized according to the procedure used for preparing example 110 from the compound 1 or 17 and the corresponding sulfonyl chlorides.

| Ex. | R1 | R2 | Name of the compounds | HPLC | Yld. | Mass MH+/ MNa+ |
|---|---|---|---|---|---|---|
| 111 | H | H | Benzenesulfonic acid 2-methyl-3-(naphthalene-2-carbonyl)-1,1-dioxo-2H-benzo[e][1,2]thiazin-4-yl ester | 5.59' 99% | 71% | 506 |
| 112 | H | Cl | 4-Chloro-benzenesulfonic acid 2-methyl-3-(naphthalene-2-carbonyl)-1,1-dioxo-2H-benzo[e][1,2]thiazin-4-yl ester | 5.84' 99% | 94% | 540 |
| 113 | H | Me | 4-Methyl-benzenesulfonic acid 2-methyl-3-(naphthalene-2-carbonyl)-1,1-dioxo-2H-benzo[e][1,2]thiazin-4-yl ester | 5.74' 99% | 93% | 520 |
| 114 | H | CN | 4-Cyano-benzenesulfonic acid 2-methyl-3-(naphthalene-2-carbonyl)-1,1-dioxo-2H-benzo[e][1,2]thiazin-4-yl ester | 5.50' 99% | 89% | 531 |
| 115 | F | Cl | 4-Chloro-benzenesulfonic acid 7-fluoro-2-methyl-3-(naphthalene-2-carbonyl)-1,1-dioxo-2H-benzo[e][1,2]thiazin-4-yl ester | 5.96' 96% | 55% | 558 580 |
| 116 | F | Me | 4-Methyl-benzenesulfonic acid 7-fluoro-2-methyl-3-(naphthalene-2-carbonyl)-1,1-dioxo-2H-benzo[e][1,2]thiazin-4-yl ester | 5.88' 97% | 59% | 538 560 |
| 117 | F | CN | 4-Cyano-benzenesulfonic acid 7-fluoro-2-methyl-3-(naphthalene-2-carbonyl)-1,1-dioxo-2H-benzo[e][1,2]thiazin-4-yl ester | 5.59' 97% | 56% | 549 571 |

EXAMPLE 118

(4-Hydroxy-2-methyl-7-piperidin-1-yl-1,1-dioxo-2H-benzo[e][1,2]thiazin-3-yl)-naphthalen-2-yl-methanone

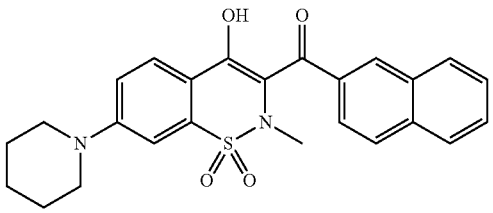 [SMILES: CN1C(C(=O)c2ccc3ccccc3c2)=C(O)c2ccc(N3CCCCC3)cc2S1(=O)=O]

The compound 17 (200 mg, 0.52 mmol) is dissolved in DMSO (2 mL) in the presence of $K_2CO_3$ (144 mg, 1.04 mmol) and then treated at room temperature with piperidine (154 μl, 1.56 mmol). The reaction is stirred at 100° C. for 20 hours and then the medium is taken up in ethyl acetate and washed with water and with a saturated NaCl solution. The organic phases are combined, dried on magnesium sulfate, filtered and concentrated. The thereby obtained residue is purified on a column of 12 g of silica (flow rate 12 mL/min, gradient of 0 to 50% ethyl acetate in heptane) in order to obtain the compound 118 as a yellow powder (22 mg; 9.5%).

HPLC: RT=6.39 min, 96%

$^1$H NMR, dmso-$d_6$, δ (ppm): 1.64 (broad s, 6H); 2.63 (s, 3H); 3.57 (broad s, 4H); 7.22 (d, 1H); 7.34 (dd, 1H); 7.65-7.70 (m, 2H); 7.96 (d, 1H); 8.03 (d, 1H); 8.09-8.11 (m, 3H); 8.62 (s, 1H).

Mass spectrum (ESI+): m/z 449 (MH+, 100%).

EXAMPLES 119 TO 121

The compounds 119 to 121 were synthesized according to the procedure used for preparing example 118 from the compound 17 and the corresponding amines.

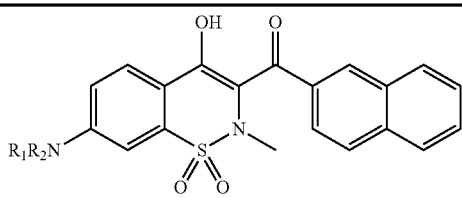

| Ex. | NR₁R₂ | Name of the compounds | HPLC | Yld. | Mass MH+/ M − H⁻ |
|---|---|---|---|---|---|
| 119 | NMe₂ | (7-Dimethylamino-4-hydroxy-2-methyl-1,1-dioxo-2H-benzo[e][1,2]thiazin-3-yl)-naphthalen-2-yl-methanone | 5.86' 100% | 35% | 409 |

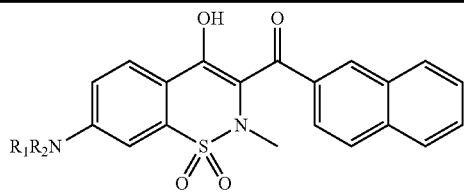

| Ex. | NR$_1$R$_2$ | Name of the compounds | HPLC | Yld. | Mass MH$^+$/M − H$^−$ |
|---|---|---|---|---|---|
| 120 | pyrrolidin-1-yl | (4-Hydroxy-2-methyl-7-pyrrolidin-1-yl-1,1-dioxo-2H-benzo[e][1,2]thiazin-3-yl)-naphthalen-2-yl-methanone | 6.18' | 13% | 435 |
| | | | 100% | | |
| 121 | 4-phenyl-piperazin-1-yl | [4-Hydroxy-2-methyl-7-(4-phenyl-piperazin-1-yl)-1,1-dioxo-2H-benzo[e][1,2]thiazin-3-yl]-naphthalen-2-yl-methanone | 6.18' | 93% | 524 |
| | | | 94% | | |

EXAMPLE 122

(7-tertButyl-4-hydroxy-2-methyl-1,1-dioxo-2H-benzo[e][1,2]thiazin-3-yl)(naphthalen-2-yl)methanone

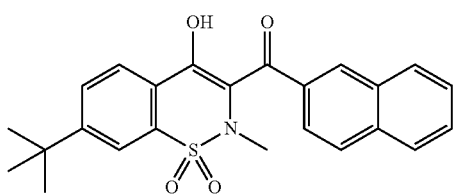 [SMILES: CN1C(C(=O)c2ccc3ccccc3c2)=C(O)c2ccc(C(C)(C)C)cc2S1(=O)=O]

The compound 122 was synthesized from 2-methyl-5-tertbutylbenzenesulfonyl chloride according to the same sequence of steps involved in preparing the compound 17. The compound is obtained as a yellow solid with an overall yield of 10%.

HPLC: RT=6.33 min, 95%

$^1$H NMR, dmso-d$_6$, δ (ppm): 1.38 (s, 9H); 2.65 (s, 3H); 7.66 (t, 1H); 7.72 (t, 1H); 7.88 (s, 1H); 8.05 (d, 2H); 8.12-8.17 (m, 4H); 8.65 (s, 1H); 15.69 (s, 1H, exch).

Mass spectrum (ESI+): m/z 422 (MH$^+$, 100%).

EXAMPLES 123 TO 130

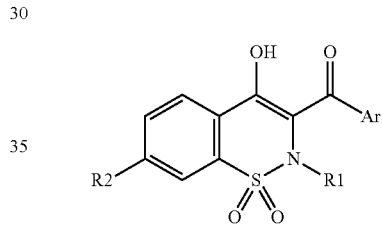

The compounds 123 to 130 were synthesized from saccharine and from corresponding 2-bromo-1-arylethanones according to the same sequence of steps described for preparing the compound 1 (for 123, 125, 127 and 128) from the compound 8 (for 124 and 126) and from the compound 17 (for 129 and 130)

| Ex. | R1 | R2 | Ar | Name of the compounds | HPLC | Yld.$^1$ | Mass MH$^+$/M-H$^−$ |
|---|---|---|---|---|---|---|---|
| 123 | Me | H | 3,4-dichlorophenyl | (4-hydroxy-2-methyl-1,1-dioxo-2H-benzo[e][1,2]thiazin-3-yl) (3,4-dichlorophenyl)methanone | 5.88' | 60% | 382 & 384 |
| | | | | | | 99% | |
| 124 | Et | H | 3,4-dichlorophenyl | (4-hydroxy-2-ethyl-1,1-dioxo-2H-benzo[e][1,2]thiazin-3-yl) (3,4-dichlorophenyl)methanone | 6.07' | 64% | 396 & 398 |
| | | | | | | 99% | |
| 125 | Me | H | benzofuran-2-yl | (4-hydroxy-2-methyl-1,1-dioxo-2H-benzo[e][1,2]thiazin-3-yl) (benzofuran-2-yl)methanone | 5.31' | 68% | 356 |
| | | | | | | 99% | |
| 126 | Et | H | benzofuran-2-yl | (4-hydroxy-2-ethyl-1,1-dioxo-2H-benzo[e][1,2]thiazin-3-yl) (benzofuran-2-yl)methanone | 5.54' | 63% | 370 |
| | | | | | | 99% | |

-continued

| Ex. | R1 | R2 | Ar | Name of the compounds | HPLC | Yld.[1] | Mass MH+/M-H- |
|---|---|---|---|---|---|---|---|
| 127 | Me | H | 5,6,7,8-tetrahydro-naphthalen-2-yl | (4-Hydroxy-2-methyl-1,1-dioxo-2H-benzo[e][1,2]thiazin-3-yl)-(5,6,7,8-tetrahydro-naphthalen-2-yl)-methanone | 6.04' | 60% 100% | 370 |
| 128 | Me | H | 5,5,8,8-tetramethyl-5,6,7,8-tetrahydro-naphthalen-2-yl | (4-Hydroxy-2-methyl-1,1-dioxo-2H-benzo[e][1,2]thiazin-3-yl)-(5,5,8,8-tetramethyl-5,6,7,8-tetrahydro-naphthalen-2-yl)-methanone | 6.66' | 70% 100% | 426 |
| 129 | Me | F | 5,6,7,8-tetrahydro-naphthalen-2-yl | (7-Fluoro-4-hydroxy-2-methyl-1,1-dioxo-2H-benzo[e][1,2]thiazin-3-yl)-(5,6,7,8-tetrahydro-naphthalen-2-yl)-methanone | 6.14' | 68% 95% | 386 |
| 130 | Me | F | 5,5,8,8-tetramethyl-5,6,7,8-tetrahydro-naphthalen-2-yl | (7-Fluoro-4-hydroxy-2-methyl-1,1-dioxo-2H-benzo[e][1,2]thiazin-3-yl)-(5,5,8,8-tetramethyl-5,6,7,8-tetrahydro-naphthalen-2-yl)-methanone | 6.75' | 80% 93% | 442 |

[1] Overall yield for the 3 steps.
* $^1$H NMR, dmso-$d_6$,
Ex. 123: 2.68 (s, 3H); 7.95 (d, 1H); 7.98-8.00 (m, 4H); 8.16 (d, 1H); 8.19-8.21 (m, 1H); 14.93 (s, 1H, exch).
Ex. 124: 0.55 (t, 3H); 3.16 (q, 2H); 7.92 (d, 1H); 7.97-7.98 (m, 4H); 8.16 (d, 1H); 8.19-8.20 (m, 1H); 14.77 (s, 1H, exch).
Ex. 125: 2.98 (s, 3H); 7.43 (t, 1H); 7.62 (dt, 1H); 7.80 (d, 1H); 7.99-8.04 (m, 4H); 8.20 (se, 1H); 8.34 (s, 1H); 15.56 (se, exch., 1H).
Ex. 126: 0.67 (t, 3H); 3.57 (q, 2H); 7.43 (t, 1H); 7.63 (dt, 1H); 7.80 (d, 1H); 7.96-8.18 (m, 4H); 8.20 (se, 1H); 8.31 (s, 1H); 15.33 (se, exch., 1H).
Ex. 127: 1.78 (s, 4H); 2.64 (s, 3H); 2.81 (s, 4H); 7.30 (d, 1H); 7.45 (s, 1H); 7.86 (d, 1H); 7.98 (m, 3H); 8.18-8.21 (m, 1H); 15.75 (s, 1H).
Ex. 128: 1.30 (d, 12H); 1.70 (s, 4H); 2.64 (s, 3H); 7.58 (d, 1H); 7.78 (d, 1H); 7.98 (m, 3H); 8.18-8.21 (m, 1H); 8.25 (d, 1H); 15.62 (s, 1H).
Ex. 129: 1.77 (broad s, 4H) ; 2.67 (s, 3H) ; 2.80 (broad s, 4H); 7.23 (broad s, 1H); 7.60-7.85 (m, 4H); 8.21 (m, 1H); 15.85 (s, 1H).
Ex. 130: 1.28 (d, 12H); 1.69 (s, 4H); 2.65 (s, 3H); 7.51 (d, 1H); 7.66 (d, 1H); 7.88 (m, 2H); 8.08 (broad s, 1H) ; 8.21 (q, 1H) ; 15.65 (s, 1H).

EXAMPLES 131 TO 143

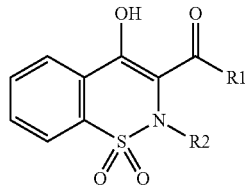

The compounds 131 to 143 were synthesized from saccharine and from the corresponding 2-bromo-1-arylethanones according to the same sequence of steps described for preparing the compound 1 (R2=Me) or the compound 8 (R2=Et).

| Ex.* | R1 | R2 | Name of the compounds | HPLC | Yld.[1] | MH+ |
|---|---|---|---|---|---|---|
| 131 | (2,3-dihydro-benzofuran-5-yl) | Me | (2,3-Dihydro-benzofuran-5-yl)-(4-hydroxy-2-methyl-1,1-dioxo-1,2-dihydro-2H-benzo[e][1,2]thiazin-3-yl)-methanone | 5.59' | 24% 98% | 358 |
| 132 | (2,3-dihydro-benzofuran-5-yl) | Et | (2,3-Dihydro-benzofuran-5-yl)-(4-hydroxy-2-ethyl-1,1-dioxo-1,2-dihydro-2H-benzo[e][1,2]thiazin-3-yl)-methanone | 5.75' | 23% 98% | 372 |

-continued

| Ex.* | R1 | R2 | Name of the compounds | HPLC | Yld.[1] | MH+ |
|---|---|---|---|---|---|---|
| 133 | 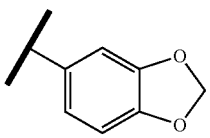 | Me | Benzo[1,3]dioxol-5-yl-(4-hydroxy-2-methyl-1,1-dioxo-1,2-dihydro-2H-benzo[e][1,2]thiazin-3-yl)-methanone | 5.50' | 34% 99% | 360 |
| 134 | 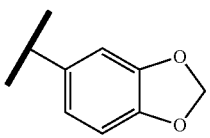 | Et | Benzo[1,3]dioxol-5-yl-(4-hydroxy-2-ethyl-1,1-dioxo-1,2-dihydro-2H-benzo[e][1,2]thiazin-3-yl)-methanone | 5.66' | 34% 97% | 374 |
| 135 | 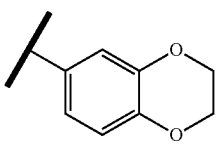 | Me | (2,3-Dihydro-benzo[1,4]dioxin-6-yl)-(4-hydroxy-2-methyl-1,1-dioxo-1,2-dihydro-2H-benzo[e][1,2]thiazin-3-yl)-methanone | 5.53' | 45% 96% | 374 |
| 136 | 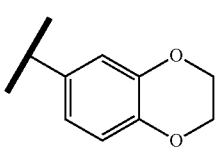 | Et | (2,3-Dihydro-benzo[1,4]dioxin-6-yl)-(4-hydroxy-2-ethyl-1,1-dioxo-1,2-dihydro-2H-benzo[e][1,2]thiazin-3-yl)-methanone | 5.68' | 42% 99% | 388 |
| 137 | 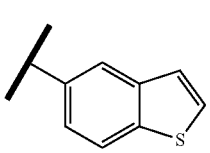 | Me | Benzo[b]thiophen-5-yl-(4-hydroxy-2-methyl-1,1-dioxo-1,2-dihydro-2H-benzo[e][1,2]thiazin-3-yl)-methanone | 5.56' | 31% 99% | 372 |
| 138 | 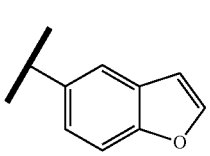 | Me | Benzofuran-5-yl-(4-hydroxy-2-methyl-1,1-dioxo-1,2-dihydro-2H-benzo[e][1,2]thiazin-3-yl)-methanone | 5.34' | 36% 99% | 356 |
| 139 | 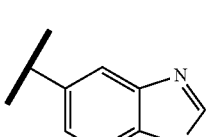 | Me | (4-Hydroxy-2-methyl-1,1-dioxo-1,2-dihydro-2H-benzo[e][1,2]thiazin-3-yl)-(1-methyl-1H-benzoimidazol-5-yl)-methanone | 3.72' | 5% 99% | 370 |
| 140 | 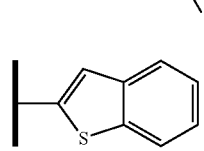 | Me | Benzo[b]thiophen-2-yl-(4-hydroxy-2-methyl-1,1-dioxo-1,2-dihydro-2H-benzo[e][1,2]thiazin-3-yl)-methanone | 5.89' | 48% 99% | 372 |
| 141 | 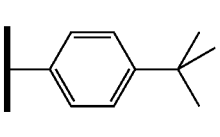 | Me | (4-tert-Butyl-phenyl)-(4-hydroxy-2-methyl-1,1-dioxo-1,2-dihydro-2H-benzo[e][1,2]thiazin-3-yl)-methanone | 6.97' | 32% 99%** | 372 |
| 142 | 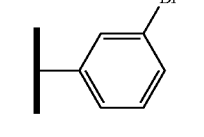 | Me | (3-Bromo-phenyl)-(4-hydroxy-2-methyl-1,1-dioxo-1,2-dihydro-2H-benzo[e][1,2]thiazin-3-yl)-methanone | 6.47' | 57% 99%** | 394/396 |

| Ex.* | R1 | R2 | Name of the compounds | HPLC | Yld.[1] | MH+ |
|---|---|---|---|---|---|---|
| 143 | 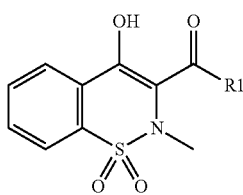 | Me | 3-(4-Hydroxy-2-methyl-1,1-dioxo-1,2-dihydro-2H-benzo[e][1,2]thiazine-3-carbonyl)-benzonitrile | 5.84' 93%** | 37% | 358 |

[1]Overall yield for the 3 steps.
*$^1$H NMR, dmso-d$_6$, Ex. 131: 2.68 (s, 3 H); 3.33 (m, 2 H); 4.69 (t, 2 H); 7.02 (d, 1 H); 7.97-7.98 (m, 3 H); 8.03 (s, 1 H); 8.08 (dd, 1 H); 8.18-8.20 (m, 1 H); 16.03 (s, 1 H, exch). Ex. 132: 0.55 (t, 3 H); 3.18 (q, 2 H); 3.28-3.34 (m, 2 H); 4.69 (t, 2 H); 7.00 (d, 1 H); 7.94-7.98 (m, 4 H); 8.03 (d, 1 H); 8.17-8.19 (m, 1 H); 15.77 (s, 1 H, exch). Ex. 133: 2.69 (s, 3 H); 6.21 (s, 2 H); 7.19 (d, 1 H); 7.56 (d, 1 H); 7.82 (dd, 1 H); 7.96-7.99 (m, 3 H); 8.18-8.20 (m, 1 H); 15.66 (s, 1 H, exch). Ex. 134: 0.56 (t, 3 H); 3.18 (q, 2 H); 6.20 (s, 2 H); 7.18 (d, 1 H); 7.53 (d, 1 H); 7.77 (dd, 1 H); 7.94-7.96 (m, 3 H); 8.17-8.19 (m, 1 H); 15.39 (s, 1 H, exch). Ex. 135: 0.55 (t, 3 H); 3.18 (q, 2 H); 4.33 (t, 2 H); 4.37 (t, 2 H); 7.09 (d, 1 H); 7.64 (d, 1 H); 7.67 (dd, 1 H); 7.94-7.96 (m, 3 H); 8.17-8.19 (m, 1 H); 15.55 (s, 1 H, exch). Ex. 136: 0.55 (t, 3 H); 3.18 (q, 2 H); 4.33 (t, 2 H); 4.37 (t, 2 H); 7.09 (d, 1 H); 7.64 (d, 1 H); 7.67 (dd, 1 H); 7.94-7.96 (m, 3 H); 8.17-8.19 (m, 1 H); 15.55 (s, 1 H, exch). Ex. 137: 2.65 (s, 3 H); 7.69 (d, 1 H); 7.96 (d, 1 H); 7.98-8.00 (m, 3 H); 8.07 (d, 1 H); 8.21-8.23 (m, 1 H); 8.28 (s, 1 H); 8.60 (s, 1 H); 15.69 (s, 1 H, exch). Ex. 138: 2.64 (s, 3 H); 7.22 (d, 1 H); 7.86 (d, 1 H); 7.98-8.00 (m, 3 H); 8.09 (dd, 1 H); 8.19 (d, 1 H); 8.21-8.45 (m, 1 H); 8.45 (s, 1 H); 15.71 (s, 1 H, exch). Ex. 139: 2.63 (s, 3 H); 3.92 (s, 3 H); 7.81 (d, 1 H); 7.98-8.05 (m, 4 H); 8.20-8.23 (m, 1 H); 8.52 (s, 1 H); 8.52 (s, 1 H); 15.87 (s, 1 H, exch). Ex. 140: 2.97 (s, 3 H); 7.53 (t, 1 H); 7.61 (t, 1 H); 8.00-8.02 (m, 3 H); 8.17-8.22 (m, 3 H); 8.67 (s, 1 H); 15.70 (s, 1 H, exch). Ex. 141: 1.34 (s, 9 H); 2.66 (s, 3 H); 7.66 (d, 2 H); 7.98-8.00 (m, 3 H); 8.06 (d, 2 H); 8.18-8.21 (m, 1 H); 15.71 (s, 1 H, exch). Ex. 142: 2.65 (s, 3 H); 7.60 (t, 1 H); 7.90 (d, 1 H); 7.95-8.05 (m, 4 H); 8.11 (s, 1 H); 8.19 (broad s, 1 H); 15.06 (s, 1 H, exch). Ex. 143: 2.65 (s, 3 H); 7.84 (t, 1 H); 7.95-8.00 (m, 3 H); 8.15-8.21(m, 2 H); 8.28-8.31 (m, 2 H); 14.86 (broad s, 1 H, exch).
**XBridge column

EXAMPLES 144 TO 146

The compounds 144 to 146 were synthesized from saccharine and from the corresponding 2-bromo-1-arylethanones according to the same sequence of steps described for the preparation of the compound 1.

The 2-bromo-1-arylethanones were prepared by bromination of the corresponding arhylethanones, according to the procedure described for preparing the compound 144A: 1-(3,4-dimethylphenyl)ethanone (2.5 g, 16.9 mmol) is dissolved under a nitrogen atmosphere in 42 mL of THF at room temperature. Trifluoroacetic acid (1.5 mL, 16.9 mmol) is added followed by pyridinium tribromide (6.5 g, 20.2 mmol). The solution turns vermilion red and a white precipitate gradually appears. After three hours of stirring at room temperature, the reaction is neutralized by adding 50 mL of water, and then extracted with 100 mL of ethyl acetate. The organic phase is washed with 40 mL of a saturated $CuSO_4$ solution, 40 mL of a saturated NaCl solution, and then dried on magnesium sulfate, filtered and concentrated under reduced pressure. The residue is purified on a column of 130 of silica with a gradient of 0% to 5% ethyl acetate in heptane in order to obtain two batches of 2-bromo-1-(3,4-dimethyl-phenyl)-ethanone (144A, 57%).

Batch 1: 1.25 g; HPLC: RT=4.90 min, 90%.
Batch 2: 1.90 g; HPLC: RT=4.90 min, 70%.

| Ex.* | R1 | Name of the compounds | HPLC | Yld.[1] | MH+ |
|---|---|---|---|---|---|
| 144 | 3,4-dimethylphenyl | (3,4-Dimethyl-phenyl)-(4-hydroxy-2-methyl-1,1-dioxo-1,2-dihydro-2H-benzo[e][1,2]thiazin-3-yl)-methanone | 5.62' 99% | 27% | 344 |
| 145 | 3-CF3-phenyl | (4-Hydroxy-2-methyl-1,1-dioxo-1,2-dihydro-2H-benzo[e][1,2]thiazin-3-yl)-(3-trifluoromethyl-phenyl)-methanone | 6.56' 99%** | 23% | 384 |
| 146 | 4-CF3-phenyl | (4-Hydroxy-2-methyl-1,1-dioxo-1,2-dihydro-2H-benzo[e][1,2]thiazin-3-yl)-(4-trifluoromethyl-phenyl)-methanone | 6.64' 99%** | 17% | 384 |

[1]Overall yield for the 4 steps.
*$^1$H NMR, dmso-d$_6$, Ex. 144: 2.33 (s, 3H); 2.34 (s, 3H); 2.63 (s, 3H); 7.40 (d, 1H); 7.82 (s, 1H); 7.90 (d, 1H); 7.98-8.00 (m, 3H); 8.18-8.21 (m, 1H); 15.73 (s, 1H, exch). Ex. 145: 2.65 (s, 3H); 7.89 (t, 1H); 8.00-8.01 (m, 3H); 8.08 (d, 1H); 8.20-8.22 (m, 1H); 8.30 (broad s, 2H), 15.00 (broad s, 1H, exch). Ex. 146: 2.64 (s, 3H); 8.00-8.03 (m, 5H); 8.17-8.21 (m, 3H); 15.06 (broad s, 1H, exch).
**XBridge column.

EXAMPLE 147

Adamantan-2-yl-(4-hydroxy-2-methyl-1,1-dioxo-1,2-dihydro-2H-benzo[e][1,2]thiazin-3-yl)-methanone

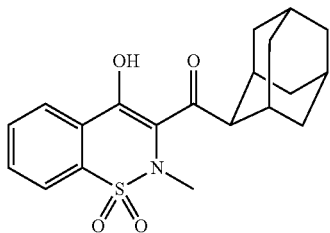 [SMILES: CN1C(C(=O)C2C3CC4CC(C3)CC2C4)=C(O)c2ccccc2S1(=O)=O]

EXAMPLE 147A

Adamantane-2-carbonitrile

Adamantanone (2.5 g, 16.6 mmol) is dissolved under an nitrogen atmosphere under 58 mL of 1,2-dimethoxyethane (DME) in the presence of ethanol (1.7 mL) and of TosMIC (4.22 g, 21.6 mmol). The reaction medium is cooled with an ice bath. Potassium tert-butylate (5.72 g, 51 mmol) is slowly added, while maintaining the temperature of the reaction medium between 2° C. and 11° C. The reaction is stirred for 30 minutes between 5° C. and 12° C. before being brought back to room temperature and stirring is continued for 2 hours. The reaction medium is filtered and the white precipitate is rinsed with DME. The filtrate is concentrated. The thereby obtained residue is purified on silica (5% ethyl acetate in heptane), in order to obtain the compound 147A as a white solid (2.38 g, 88%).

$^1$H NMR, dmso-$d_6$, δ (ppm): 1.65-1.95 (m, 12H); 2.07 (broad s, 2H); 3.14 (broad s, 1H).

Mass spectrum (ESI+): m/z 162 (MH$^+$, 20%); 194 (MH$^+$.MeOH, 100%).

EXAMPLE 147B

1-Adamantan-2-yl-ethanone

The compound 147A (4.63 g, 28.7 mmol) is dissolved under a nitrogen atmosphere in 61 mL of ether, and then cooled with an ice bath. Methyllithium (27 mL, 1.6 M/Et$_2$O, 43 mmol) is added dropwise while maintaining the reaction medium between 5° C. and 12° C. As soon as the addition is finished, the cold bath is removed and stirring is continues for 30 minutes at room temperature. The reaction medium is then neutralized with 46 ml of water. The organic phase is recovered, dried on magnesium sulfate, dried and concentrated under reduced pressure. The residue is taken up in 28 mL of acetone and 28 mL of 6N HCl, and then refluxed for heating for 80 minutes. The acetone is then evaporated and the residual aqueous phase is extracted twice with ethyl acetate. The organic phases are combined, dried on magnesium sulfate, filtered and concentrated. The thereby obtained residue is purified on a column of 90 g of silica (32 mL/min, 6% ethyl acetate in heptane), in order to obtain the compound 147B as a yellow solid (3.66 g, 71%).

$^1$H NMR, dmso-$d_6$, δ (ppm): 1.45-1.55 (m, 2H); 1.65-1.90 (m, 10H); 2.09 (s, 3H); 2.29 (broad s, 2H); 2.54 (broad s, 1H).

Mass spectrum (ESI+): m/z 179 (MH$^+$, 100%).

EXAMPLE 147C

1-Adamantan-2-yl-2-bromo-ethanone

The compound 147B (500 mg, 2.8 mmol) is dissolved in 8.6 mL of methanol under a nitrogen atmosphere, and then cooled to 0° C. Bromine (151 μl, 2.94 mmol) is slowly added. The reaction medium is stirred for 1 h 40 min at 0° C. and then neutralized with water and extracted twice with ethyl acetate. The organic phases are combined, dried on magnesium sulfate, filtered and concentrated. The thereby obtained residue is purified on a column of 35 g of silica (20 mL/min, gradient of 0% to 15% ethyl acetate in heptane in 25 minutes), in order to obtain the compound 147C (1.37 g, 85%).

$^1$H NMR, dmso-$d_6$, (ppm): 1.5-1.6 (m, 2H); 1.65-1.90 (m, 10H); 2.38 (broad s, 2H); 2.86 (broad s, 1H); 4.45 (s, 2H).

EXAMPLE 147

Adamantan-2-yl-(4-hydroxy-2-methyl-1,1-dioxo-1,2-dihydro-2H-benzo[e][1,2]thiazin-3-yl)-methanone The compound 147 was synthesized from saccharin and from the compound 147C according to the same sequence of steps described for preparing the compound 1 with a yield of 11% for the three steps.

White Solid

HPLC: RT=6.28 min, 97%

$^1$H NMR, dmso-$d_6$, δ (ppm): 1.54-1.61 (m, 2H); 1.68-1.93 (m, 8H); 2.05-2.25 (m, 2H); 2.36 (broad s, 2H); 2.89 (s, 3H); 3.27 (s, 1H); 7.93-7.96 (m, 3H); 8.08-8.11 (m, 1H); 15.22 (s, 1H, exch).

Mass spectrum (ESI−): m/z 372 (M-H$^-$, 100%).

EXAMPLE 148

Chroman-6-yl-(4-hydroxy-2-methyl-1,1-dioxo-1,2-dihydro-2H-benzo[e][1,2]thiazin-3-yl)-methanone

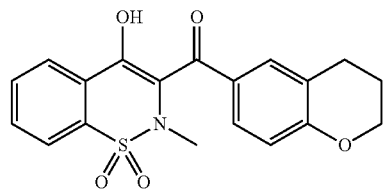 [SMILES: CN1C(C(=O)c2ccc3c(c2)CCCO3)=C(O)c2ccccc2S1(=O)=O]

EXAMPLE 148A

Chromane 4-chromanone (5.0 g, 33.7 mmol) is dissolved in 102 mL of THF under a nitrogen atmosphere. BF$_3$.OEt$_2$ (12.8 mL, 101 mmol) is added at room temperature and sodium cyanoborohydride (4.33 g, 67.4 mmol) is added slowly (violent reaction). The thereby obtained white suspension is heated to 65° C. of 18 hours, and then neutralized with water. The reaction mixture is extracted twice with ethyl acetate. The organic phases are combined, successively washed with a saturated NaHCO$_3$ solution and a saturated NaCl solution, and then dried on magnesium sulfate, filtered and concentrated under reduced pressure. The thereby obtained residue is purified on silica (gradient of 0% to 50% dichloromethane in heptane, and then 10% ethyl acetate in heptane), in order to obtain the partly purified compound 148A (3.34 g, 61%).

HPLC: RT=4.56 min, 83%

$^1$H NMR, dmso-d$_6$, δ (ppm): 1.91 (q, 2H); 2.72 (t, 2H); 4.11 (t, 2H); 6.70 (d, 1H); 6.80 (t, 1H); 7.0-7.05 (m, 2H).

EXAMPLE 148B

1-Chroman-6-yl-ethanone

Chromane (4.64 g, 29.4 mmol) is dissolved in 30 mL of anhydrous dichloromethane (DCM) under a nitrogen atmosphere. The reaction medium is cooled to −30° C., and then a cold solution (−10° C.) of ethanoyl chloride (4.75 mL, 67 mmol) in 20 mL of anhydrous DCM is added within 5 minutes. The mixture is stirred for 45 min at −15° C., and then poured over a mixture of 100 g of ice and 50 mL of concentrated HCl and extracted three times with DCM. The organic phases are combined, dried on magnesium sulfate, filtered and concentrated under reduced pressure. The thereby obtained residue is purified on a column of 120 g of silica (gradient of 0% to 20% EtOAc in heptane in 60 minutes), in order to obtain two batches of compound 148B (70%).

Batch 1: 2.25 g; HPLC: RT=4.09 min, 96.6%.

$^1$H NMR, dmso-d$_6$, δ (ppm): 1.93 (q, 2H); 2.49 (s, 3H); 2.79 (t, 2H); 4.21 (t, 2H); 6.81 (d, 1H); 7.65-7.75 (m, 2H).

Mass spectrum (ESI+): m/z 177 (MH$^+$, 100%).

Batch 2: 1.79 g; HPLC: RT=4.09 min, 81%.

EXAMPLE 148C

2-Bromo-1-chroman-6-yl-ethanone

The compound 148C was synthesized from the compound 148B according to the procedure for preparing the compound 144A, with a yield of 65%.

HPLC: RT=4.59 min, 74%.

$^1$H NMR, dmso-d$_6$, (ppm): 1.95 (q, 2H); 2.80 (t, 2H); 4.20 (t, 2H); 4.80 (s, 2H); 6.85 (d, 1H); 7.70-7.85 (m, 2H).

EXAMPLE 148

Chroman-6-yl-(4-hydroxy-2-methyl-1,1-dioxo-1,2-dihydro-2H-benzo[e][1,2]thiazin-3-yl)-methanone The compound 148 was synthesized from saccharin and from the compound 148C according to the same sequence of steps described for preparing the compound 1, with an overall yield of 36%.

HPLC: RT=5.45 min, 98%

$^1$H NMR, dmso-d$_6$, δ (ppm): 1.98 (t, 2H); 2.69 (s, 3H); 2.84 (t, 2H); 4.27 (t, 2H); 6.96 (d, 1H); 7.89 (s, 1H); 7.97-8.02 (m, 4H); 8.17-8.18 (m, 1H); 16.02 (s, 1H, exch).

Mass spectrum (ESI+): m/z 372 (MH$^+$, 100%).

EXAMPLE 149

(4-Chloro-3-trifluoromethyl-phenyl)-(4-hydroxy-2-methyl-1,1-dioxo-1,2-dihydro-2H-benzo[e][1,2]thiazin-3-yl)-methanone

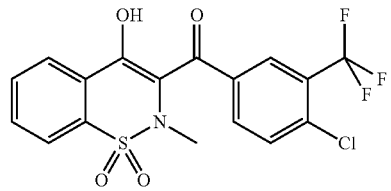 [SMILES: CN1C(C(=O)c2ccc(Cl)c(C(F)(F)F)c2)=C(O)c2ccccc2S1(=O)=O]

EXAMPLE 149A 1-(4-Chloro-3-trifluoromethyl-phenyl)-ethanol 4-chloro-3-trifluoromethyl-benzaldehyde (6.19 g, 29.7 mmol) is dissolved in 124 mL of THF under a nitrogen atmosphere. The reaction medium is cooled to −78° C. before adding dropwise MeMgBr (13 mL, 3M/Et$_2$O, 38.6 mmol), and then stirred for a further 2 hours at this low temperature, and finally neutralized by adding 60 mL of a saturated NH$_4$Cl solution. The reaction medium is extracted twice with ethyl acetate. The organic phases are combined, washed with a saturated NaCl solution, and then dried on magnesium sulfate, filtered and concentrated under reduced pressure. The thereby obtained residue is purified on a column of 120 g of silica (92 mL/min; gradient of 0% to 35% ethyl acetate in heptane in 40 min), in order to obtain the compound 149A (5.71 g, 62%).

HPLC: RT=5.71 min, 98% (colonne XBridge)

$^1$H NMR, dmso-d$_6$, δ (ppm): 1.33 (d, 3H); 4.81 (quintet, 1H); 5.46 (d, 1H, exch); 7.60-7.69 (m, 2H); 7.81 (s, 1H).

EXAMPLE 149B 1-(4-Chloro-3-trifluoromethyl-phenyl)-ethanone

The compound 149A (2.62 g, 11.7 mmol) is dissolved in 53 mL of DCM in the presence of 3.8 g of celite. PCC (3.77 g, 17.5 mmol) is added at room temperature and the reaction medium is stirred overnight before being filtered. The filtrate is concentrated under reduced pressure. The thereby obtained residue is purified on a column of 80 g of silica (32 mL/min, gradient of 0% to 30% EtOAc in heptane in 26 minutes), in order to obtain the compound 149B (2.27 g, 87%).

HPLC: RT=5.84 min, 97% (colonne XBridge)

$^1$H NMR, dmso-d$_6$, δ (ppm): 2.65 (s, 3H); 7.92 (d, 1H); 8.22-8.27 (m, 2H).

EXAMPLE 149C

2-Bromo-1-(4-chloro-3-trifluoromethyl-phenyl)-ethanone

The compound 149C was synthesized from the compound 149B according to the procedure for preparing the compound 144A, with a yield of 66%.

HPLC: RT=6.18 min, 89% (colonne XBridge)

¹H NMR, dmso-d₆, δ (ppm): 5.05 (s, 2H); 7.96 (d, 1H); 8.28 (d, 1H); 8.34 (s, 1H).

EXAMPLE 149

(4-Chloro-3-trifluoromethyl-phenyl)-(4-hydroxy-2-methyl-1,1-dioxo-1,2-dihydro-2H-benzo[e][1,2]thiazin-3-yl)-methanone The compound 149 was synthesized from saccharin and from the compound 149C according to the same sequence of steps described for preparing the compound 1, with an overall yield of 20%.

HPLC: RT=6.71 min, 99% (XBridge column)
¹H NMR, dmso-d₆, (ppm): 2.68 (s, 3H); 7.98-8.04 (m, 4H); 8.18-8.21 (m, 1H); 8.29 (d, 1H); 8.40 (s, 1H); 14.82 (s, 1H, exch).
Mass spectrum (ESI−): m/z 416 (M-H⁻, 100%); 418 (M-H⁻, 25%).

EXAMPLE 150

(7-Bromo-4-hydroxy-2-methyl-1,1-dioxo-1,2-dihydro-2H-benzo[e][1,2]thiazin-3-yl)-naphthalen-2-yl-methanone

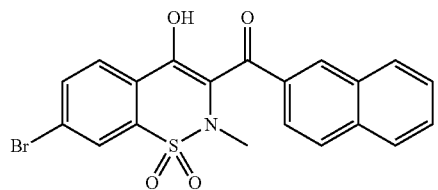 [SMILES: CN1C(C(=O)c2ccc3ccccc3c2)=C(O)c2ccc(Cl)cc2S1(=O)=O]

EXAMPLE 150A

4-Bromo-2-sulfamoyl-benzoic acid 5-bromo-2-methyl-benzenesulfonamide (2.5 g, 9.99 mmol) is dissolved in 62 mL of soda (5% in water). The reaction is heated to 100° C. and KMnO₄ (6.43 g, 25 mmol) is gradually added within 15 minutes. Heating is continued for 140 minutes. The reaction medium is cooled to room temperature and then filtered. The pH of the filtrate is brought back to 1.2 with a concentrated HCl solution, and then filtered. The precipitate is rinsed with ethyl acetate. The two phases of the filtrate are separated and the aqueous phase is extracted once with ethyl acetate. The organic phases are collected, dried on magnesium sulfate, filtered and concentrated under reduced pressure, in order to obtain the compound 150A (1.64 g, 58%).

HPLC: RT=0.29 min, 99.5%
¹H NMR, dmso-d₆, δ (ppm): 7.35 (s, 2H, exch); 7.67 (d, 1H); 7.91 (d, 1H); 8.08 (s, 1H); 13.83 (broad s, 1H, exch).
Mass spectrum (ESI−): m/z 278 (M-H⁻, 100%); 280 (M-H⁻, 87%).

EXAMPLE 150B

6-Bromo-1,1-dioxo-1,2-dihydro-2H-benzo[d]isothiazol-3-one

The compound 150A (1.59 g, 5.56 mmol) is dissolved in 6 mL of concentrated sulfuric acid at room temperature and the reaction medium is stirred for 3 hours before being poured over ice. The suspension is filtered. The precipitate is rinsed three times with water, and then dried for 24 hours at 50° C. and in vacuo. The compound 150B (1.33 g, 89%) is obtained as a white solid.

HPLC: RT=3.16 min, 96%
¹H NMR, dmso-d₆, δ (ppm): 7.85 (d, 1H); 8.08 (d, 1H); 8.48 (s, 1H).
Mass spectrum (ESI−): m/z 260 (M-H⁻, 100%); 262 (M-H⁻, 94%).

EXAMPLE 150

(7-Bromo-4-hydroxy-2-methyl-1,1-dioxo-1,2-dihydro-2H-benzo[e][1,2]thiazin-3-yl)-naphthalen-2-yl-methanone The compound 150 was synthesized from the compound 150B and from 2-bromo-1-(naphthalen-2-yl)ethanone according to the same sequence of steps described for preparing the compound 1, with an overall yield of 55%.

HPLC: RT=6.14 min, 97%
¹H NMR, dmso-d₆, δ (ppm): 2.68 (s, 3H); 7.66 (t, 1H); 7.73 (t, 1H); 8.04-8.15 (m, 5H); 8.19-8.22 (m, 2H); 8.65 (s, 1H); 15.38 (s, 1H, exch).
Mass spectrum (ESI+): m/z 444 (MH⁺, 100%); 446 (MH⁺, 99%).

EXAMPLE 151

(7-Chloro-4-hydroxy-2-methyl-1,1-dioxo-1,2-dihydro-2H-benzo[e][1,2]thiazin-3-yl)-naphthalen-2-yl-methanone

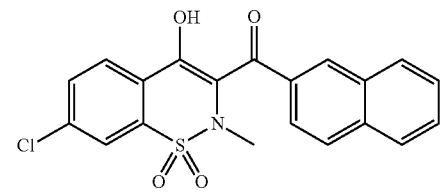

EXAMPLE 151A

6-Chloro-1,1-dioxo-1,2-dihydro-2H-benzo[d]isothiazol-3-one

Methyl 2-amino-4-chlorobenzoate (5 g, 26.9 mmol) is heated in 18 mL of HCl (20% in water) until complete dissolution, and then cooled to 0° C. A solution of NaNO₂ (1.85 g, 26.9 mmol) in 4.5 mL of water is added dropwise while maintaining the temperature between 2° C. and 6° C. The reaction medium is then stirred for 1 hour at room temperature. In a second flask, about 15 g of SO₂ gas is bubbled in 22 mL of acetic acid and 2.3 mL of water at 0° C. CuCl (666 mg, 6.7 mmol) is then added. The first reaction medium is then added to this blue-green solution between 1° C. and 3° C. Gas evolvement is observed; Stirring at low temperature is continued for 45 minutes before removing the cold bath, and then the reaction medium is poured over 100 g of ice and extracted three times with ethyl acetate. The organic phases are collected, washed with a saturated NaHCO₃ solution, dried on magnesium sulfate, filtered and concentrated under reduced pressure. The residue is taken up into 5 mL of THF at 0° C.

and 2.8 mL of a concentrated ammonia solution are added slowly. The cold bath is removed and stirring is continued for 1 hour. The reaction medium is concentrated, taken up with a saturated NaHCO₃ solution, washed once with ether, and then brought back to pH=1 with a concentrated HCl solution. The formed precipitate is filtered, rinsed with water and dried under reduced pressure at 50° C. in order to obtain the compound 151A (896 mg, 15%).

HPLC: RT=3.07 min, 99%

$^1$H NMR, dmso-d$_6$, δ (ppm): 7.94 (broad d, 2H); 8.38 (s, 1H).

Mass spectrum (ESI−): m/z 216 (M-H⁻, 100%); 218 (M-H⁻, 32%).

EXAMPLE 151

(7-Chloro-4-hydroxy-2-methyl-1,1-dioxo-1,2-dihydro-2H-benzo[e][1,2]thiazin-3-yl)-naphthalen-2-yl-methanone The compound 151 was synthesized from the compound 151A and from 2-bromo-1-(naphthalen-2-yl)ethanone according to the same sequence of steps described for preparing the compound 1, with an overall yield of 39%.

HPLC: RT=6.13 min, 95%

$^1$H NMR, dmso-d$_6$, δ (ppm): 2.68 (s, 3H); 7.66 (t, 1H); 7.74 (t, 1H); 8.03-8.16 (m, 6H); 8.21 (d, 1H); 8.65 (s, 1H); 15.41 (se, 1H, exch).

Mass spectrum (ESI−): m/z 398 (M-H⁻, 100%); 400 (M-H⁻, 32%).

EXAMPLE 152

(4-Hydroxy-2,7-dimethyl-1,1-dioxo-1,2-dihydro-2H-benzo[e][1,2]thiazin-3-yl)-naphthalen-2-yl-methanone

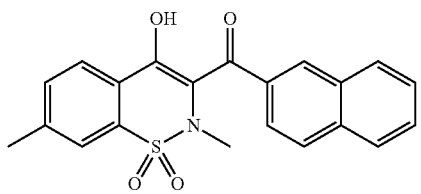 [SMILES: Cc1ccc2c(c1)S(=O)(=O)N(C)C(C(=O)c1ccc3ccccc3c1)=C2O]

EXAMPLE 152A

2-Cyano-5-methyl-benzenesulfonamide 2-amino-4-methyl-benzonitrile (2.5 g, 18.9 mmol) is heated in 12 mL of HCl (20% in water) until complete dissolution), and then cooled to 0° C. A solution of NaNO₂ (1.3 g, 18.9 mmol) in 3.2 mL of water is added dropwise while maintaining the temperature between 2° C. and 6° C. The reaction medium is then stirred for 1 hour at room temperature. In a second flask, about 15.7 g of SO₂ gas is bubbled in 15 mL of acetic acid and 1.6 mL of water at 0° C. CuCl (468 mg, 4.7 mmol) is then added. The first reaction medium is then added to this blue-green solution between 1° C. and 3° C. Gas evolvement is observed. Stirring at low temperature is continued for 45 minutes before removing the cold bath, and then the reaction mixture is poured over 70 g of ice and extracted three times with a mixture of 20% methanol in DCM. The organic phases are collected, washed with a saturated NaHCO₃ solution, dried on magnesium sulfate, filtered and concentrated under reduced pressure. The residue is taken up into 5 mL of THF at 0° C. and 2.8 mL of a concentrated ammonia solution are added slowly. The cold bath is removed and stirring is continued for 1 hour. The reaction medium is concentrated, taken up with a saturated NaHCO₃ solution, washed once with ether, and then brought back to pH=1 with a concentrated HCl solution. The formed precipitate is filtered, rinsed with water and dried under reduced pressure at 50° C. in order to obtain the compound 152A (800 mg, 21%).

HPLC: RT=3.67 min, 99% (colonne XBridge)

$^1$H NMR, dmso-d$_6$, δ (ppm): 7.61 (d, 1H); 7.77 (s, 1H); 7.99 (d, 1H); 8.77 (broad s, 2H).

Mass spectrum (ESI+): m/z 197 (MH⁺, 100%).

EXAMPLE 152B

4-Methyl-2-sulfamoyl-benzoic acid

The compound 152A (620 mg, 3.15 mmol) is dissolved in 7.5 mL of KOH (30% in water) and 530 µl of hydrogen peroxide (30% in water). The reaction medium is refluxed with heating for 4 hours, and then cooled to room temperature, brought back to pH=1 with a concentrated HCl solution and extracted three times with a mixture of 20% methanol in DCM. The organic phases are collected, dried on magnesium sulfate, filtered and concentrated under reduced pressure, in order to obtain the compound 152B (428 g, 60%).

HPLC: RT=4.11 min, 95% (colonne XBridge)

$^1$H NMR, dmso-d$_6$, δ (ppm): 2.41 (s, 3H); 7.19 (broad s, 2H, exch); 7.48 (d, 1H); 7.65 (d, 1H); 7.77 (s, 1H); 12.5-14.5 (broad s, 1H, exch).

Mass spectrum (ESI−): m/z 214 (M-H⁻, 100%).

EXAMPLE 152C

6-Methyl-1,1-dioxo-1,2-dihydro-2H-benzo[d]isothiazol-3-one

The compound 152B (428 mg, 1.94 mmol) is dissolved in 3 mL of concentrated sulfuric acid at room temperature. The reaction mixture is stirred for 2 hours and then poured over ice and filtered. The precipitate is abundantly rinsed with water and then dried in order to obtain the compound 152C (359 mg, 93%) as a pink solid.

HPLC: RT=4.00 min, 96% (XBridge column)

$^1$H NMR, dmso-d$_6$, δ (ppm): 7.74 (d, 1H); 7.89 (d, 1H); 8.00 (s, 1H).

Mass spectrum (ESI−): m/z 196 (M-H⁻, 100%).

EXAMPLE 152

(4-Hydroxy-2,7-dimethyl-1,1-dioxo-1,2-dihydro-2H-benzo[e][1,2]thiazin-3-yl)-naphthalen-2-yl-methanone The compound 152 was synthesized from the compound 152C and from 2-bromo-1-(naphthalen-2-yl)ethanone according to the same sequence of steps described for preparing the compound 1, with an overall yield of 21%.

HPLC: RT=6.87 min, 98% (XBridge column)

$^1$H NMR, dmso-d$_6$, δ (ppm): 2.55 (s, 3H); 2.64 (s, 3H); 7.66 (t, 1H); 7.72 (t, 1H); 7.80 (d, 1H); 7.84 (s, 1H); 8.05 (d, 1H); 8.11-8.11 (m, 4H); 8.67 (s, 1H); 15.75 (s, 1H, exch).

Mass spectrum (APCI+): m/z 380 (MH⁺, 24%).

EXAMPLE 153

Biphenyl-3-yl-(4-hydroxy-2-methyl-1,1-dioxo-1,2-dihydro-2H-benzo[e][1,2]thiazin-3-yl)-methanone

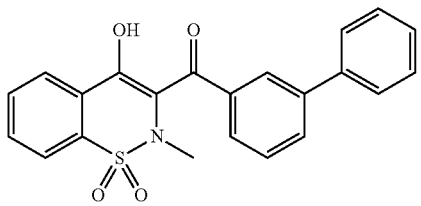 [SMILES: CN1C(C(=O)c2cccc(-c3ccccc3)c2)=C(O)c2ccccc2S1(=O)=O]

EXAMPLE 153

Biphenyl-3-yl-(4-hydroxy-2-methyl-1,1-dioxo-1,2-dihydro-2H-benzo[e][1,2]thiazin-3-yl)-methanone The compound 142 (200 mg, 0.5 mmol) is dissolved under an inert atmosphere in 1.1 mL of acetone and 1.2 mL of water in the presence of benzene boronic acid (68 mg, 0.55 mmol), of potassium carbonate (175 mg, 1.27 mmol) and palladium acetate (5 mg, 0.02 mmol). The reaction mixture is heated to 85° C. for 1 hour and 30 minutes and then brought back to room temperature, diluted with water and extracted three times with DCM. The organic phases are combined, dried on magnesium sulfate, filtered and concentrated under reduced pressure. The thereby obtained residue is purified on a column of 12 g of silica with DCM, in order to obtain the compound 153 (141 mg, 68%).

HPLC: RT=7.07 min, 96% (colonne XBridge)

$^1$H NMR, dmso-d$_6$, δ (ppm): 2.68 (s, 3H); 7.44 (t, 1H); 7.53 (t, 2H); 7.69-7.76 (m, 3H); 7.97-8.04 (m, 5H); 8.21 (broad s, 1H); 8.31 (s, 1H); 15.36 (broad s, 1H, exch).

Mass spectrum (ESI–): m/z 390 (M-H$^-$, 100%).

EXAMPLES 154 TO 169

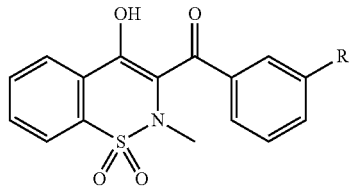

The compounds 154 to 169 were synthesized from the compound 142 and from various boronic acids according to the same method described for preparing the compound 153.

| Ex.* | R | Name of the compounds | HPLC** | Yld. | M − H$^-$ (MH$^+$) |
|---|---|---|---|---|---|
| 154 | 2-F-phenyl | (2'-Fluoro-biphenyl-3-yl)-(4-hydroxy-2-methyl-1,1-dioxo-1,2-dihydro-2H-benzo[e][1,2]thiazin-3-yl)-methanone | 6.80' 95.9% | 27% | 404 |
| 155 | 3-F-phenyl | (3'-Fluoro-biphenyl-3-yl)-(4-hydroxy-2-methyl-1,1-dioxo-1,2-dihydro-2H-benzo[e][1,2]thiazin-3-yl)-methanone | 6.93' 98.2% | 66% | 408 |
| 156 | 4-F-phenyl | (4'-Fluoro-biphenyl-3-yl)-(4-hydroxy-2-methyl-1,1-dioxo-1,2-dihydro-2H-benzo[e][1,2]thiazin-3-yl)-methanone | 6.92' 98.7% | 64% | 408 |
| 157 | 2-Cl-phenyl | (2'-Choro-biphenyl-3-yl)-(4-hydroxy-2-methyl-1,1-dioxo-1,2-dihydro-2H-benzo[e][1,2]thiazin-3-yl)-methanone | 6.99' 94.8% | 11% | (426) |
| 158 | 3-Cl-phenyl | (3'-Choro-biphenyl-3-yl)-(4-hydroxy-2-methyl-1,1-dioxo-1,2-dihydro-2H-benzo[e][1,2]thiazin-3-yl)-methanone | 7.19' 98% | 58% | (426) |

-continued

| Ex.* | R | Name of the compounds | HPLC** | Yld. | M − H⁻ (MH⁺) |
|---|---|---|---|---|---|
| 159 | 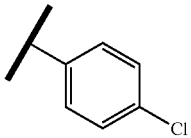 | (4'-Choro-biphenyl-3-yl)-(4-hydroxy-2-methyl-1,1-dioxo-1,2-dihydro-2H-benzo[e][1,2]thiazin-3-yl)-methanone | 7.22' 97.9% | 67% | (426) |
| 160 | 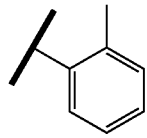 | (2'-Methyl-biphenyl-3-yl)-(4-hydroxy-2-methyl-1,1-dioxo-1,2-dihydro-2H-benzo[e][1,2]thiazin-3-yl)-methanone | 7.08' 98.4% | 61% | 404 |
| 161 | 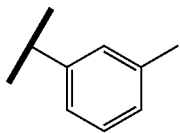 | (3'-Methyl-biphenyl-3-yl)-(4-hydroxy-2-methyl-1,1-dioxo-1,2-dihydro-2H-benzo[e][1,2]thiazin-3-yl)-methanone | 7.15' 99.6% | 60% | 404 |
| 162 | 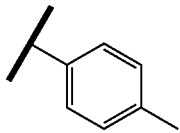 | (4'-Methyl-biphenyl-3-yl)-(4-hydroxy-2-methyl-1,1-dioxo-1,2-dihydro-2H-benzo[e][1,2]thiazin-3-yl)-methanone | 7.16' 99.5% | 70% | 404 |
| 163 | 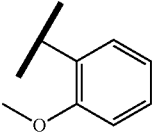 | (2'-Methoxy-biphenyl-3-yl)-(4-hydroxy-2-methyl-1,1-dioxo-1,2-dihydro-2H-benzo[e][1,2]thiazin-3-yl)-methanone | 6.85' 100% | 69% | 420 |
| 164 | 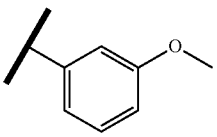 | (3'-Methoxy-biphenyl-3-yl)-(4-hydroxy-2-methyl-1,1-dioxo-1,2-dihydro-2H-benzo[e][1,2]thiazin-3-yl)-methanone | 6.86' 98.5% | 53% | 420 |
| 165 | 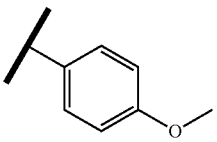 | (4'-Methoxy-biphenyl-3-yl)-(4-hydroxy-2-methyl-1,1-dioxo-1,2-dihydro-2H-benzo[e][1,2]thiazin-3-yl)-methanone | 6.83' 99.5% | 72% | 420 |
| 166 | 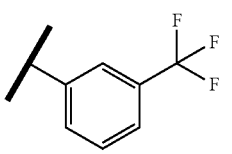 | (4-Hydroxy-2-methyl-1,1-dioxo-1,2-dihydro-2H-benzo[e][1,2]thiazin-3-yl)-(3'-trifluoromethyl-biphenyl-3-yl)-methanone | 7.17' 97.5% | 45% | 458 |
| 167 | 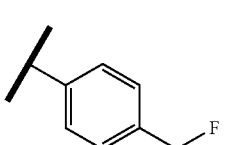 | (4-Hydroxy-2-methyl-1,1-dioxo-1,2-dihydro-2H-benzo[e][1,2]thiazin-3-yl)-(4'-trifluoromethyl-biphenyl-3-yl)-methanone | 7.22' 98.3% | 44% | 458 |
| 168 | 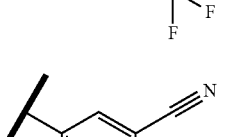 | 3'-(4-Hydroxy-2-methyl-1,1-dioxo-1,2-dihydro-2H-benzo[e][1,2]thiazine-3-carbonyl)-biphenyl-3-carbonitrile | 6.57' 99.5% | 50% | 415 |

-continued

| Ex.* | R | Name of the compounds | HPLC** | Yld. | M – H⁻ (MH⁺) |
|---|---|---|---|---|---|
| 169 | 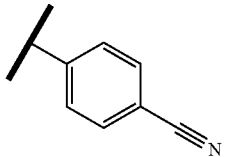 | 3'-(4-Hydroxy-2-methyl-1,1-dioxo-1,2-dihydro-2H-benzo[e][1,2]thiazine-3-carbonyl)-biphenyl-4-carbonitrile | 6.57' 97.1% | 61% | 415 |

*¹H NMR, dmso-d₆, Ex. 154: 2.68 (s, 3 H); 7.35-7.41 (m, 2 H); 7.47-7.52 (m, 1 H); 7.62 (t, 1 H); 7.75 (t, 1 H); 7.89 (d, 1 H); 7.99-8.01 (m, 3 H); 8.08 (d, 1 H); 8.21-8.22 (m, 1 H); 8.26 (s, 1 H); 15.41 (broad s, exch, 1 H). Ex. 155: 2.67 (s, 3 H); 7.28 (t, 1 H); 7.55-7.61 (m, 3 H); 7.74 (t, 1 H); 8.00-8.06 (m, 5 H); 8.21-8.23 (m, 1 H); 8.32 (s, 1 H); 15.26 (broad s, exch, 1 H). Ex. 156: 2.67 (s, 3 H); 7.37 (t, 2 H); 7.72 (t, 1 H); 7.77-7.80 (m, 2 H); 7.99-8.05 (m, 5 H); 8.20-8.23 (m, 1 H); 8.27 (s, 1 H); 15.32 (broad s, exch, 1 H). Ex.157: 2.68 (s, 3 H); 7.45-7.50 (m, 3 H); 7.63-7.65 (m, 1 H); 7.71-7.74 (m, 2 H); 7.97-7.99 (m, 3 H); 8.03 (d,1 H); 8.15 (s, 1 H); 8.19-8.20 (m, 1 H); 15.41 (broad s, exch, 1 H). Ex. 158: 2.67 (s, 3 H); 7.51 (d, 1 H); 7.57 (t, 1 H); 7.72-7.76 (m, 2 H); 7.81 (d, 1 H); 7.98-8.07 (m, 5 H); 8.21-8.23 (m, 1 H); 8.31 (s, 1 H); 15.26 (broad s, exch, 1 H). Ex. 159: 2.67 (s, 3 H); 7.59 (d, 2 H); 7.72-7.78 (m, 3 H); 7.99-8.02 (m, 4 H); 8.06 (d, 1 H); 8.20-8.23 (m, 1 H); 8.28 (s, 1 H); 15.30 (broad s, exch, 1 H). Ex. 160: 2.32 (s, 3 H); 2.68 (s, 3 H); 7.27-7.38 (m, 4 H); 7.67-7.73 (m, 2 H); 7.98-8.04 (m, 5 H); 8.20-8.22 (m, 1 H); 15.45 (broad s, exch, 1 H). Ex. 161: 2.41 (s, 3 H); 2.67 (s, 3 H); 7.25 (d, 1 H); 7.41 (t, 1 H); 7.53 (d, 1 H); 7.56 (s, 1 H); 7.71 (t, 1 H); 7.98-8.03 (m, 5 H); 8.21-8.23 (m, 1 H); 8.32 (s, 1 H); 15.35 (broad s, 1 H, exch). Ex. 162: 2.37 (s, 3 H); 2.67 (s, 3 H); 7.34 (d, 2 H); 7.63 (d, 2 H); 7.70 (t, 1 H); 7.97-8.01 (m, 5 H); 8.20-8.21 (m, 1 H); 8.30 (s, 1 H); 15.37 (broad s, 1 H, exch). Ex. 163: 2.70 (s, 3 H); 3.83 (s, 3 H); 7.09 (t, 1 H); 7.18 (d, 1 H); 7.35-7.44 (m, 2 H); 7.67 (t, 1 H); 7.79 (d, 1 H); 7.97-8.01 (m, 4 H); 8.19-8.23 (m, 1 H); 8.29 (s, 1 H); 15.58 (broad s, 1 H, exch). Ex. 164: 2.68 (s, 3 H); 3.86 (s, 3 H); 7.00 (dd, 1 H); 7.27 (s, 1 H); 7.31 (d, 1 H); 7.44 (t, 1 H); 7.72 (t, 1 H); 7.98-8.03 (m, 5 H); 8.19-8.24 (m, 1 H); 8.37 (s, 1 H); 15.32 (broad s, 1 H, exch). Ex. 165: 2.67 (s, 3 H); 3.82 (s, 3 H); 7.09 (d, 2 H); 7.66-7.71 (m, 3 H); 7.94-8.02 (m, 5 H); 8.19-8.23 (m, 1 H); 8.28 (s, 1 H); 15.38 (broad s, 1 H, exch). Ex. 166: 2.66 (s, 3 H); 7.74-7.83 (m, 3 H); 7.97-8.12 (m, 7 H); 8.19-8.24 (m, 1 H); 8.37 (s, 1 H); 15.22 (broad s, 1 H, exch). Ex. 167: 2.68 (s, 3 H); 7.78 (t, 1 H); 7.89 (d, 2 H); 7.95-8.02 (m, 5 H); 8.08-8.13 (m, 2 H); 8.19-8.24 (m, 1 H); 8.34 (s, 1 H); 15.27 (broad s, 1 H, exch). Ex. 168: 2.67 (s, 3 H); 7.73 (d, 1 H); 7.78 (d, 1 H); 7.91 (d, 1 H); 8.00 (broad s, 3 H); 8.07-8.10 (m, 3 H); 8.19-8.25 (m, 2 H); 8.32 (s, 1 H); 15.23 (broad s, 1 H, exch). Ex. 169: 2.67 (s, 3 H); 7.78 (t, 1 H); 7.94-8.03 (m, 7 H); 8.08-8.12 (m, 2 H); 8.19-8.23 (m, 1 H); 8.33 (s, 1 H); 15.23 (broad s, 1 H, exch).
** XBridge column.

EXAMPLE 170

(4-Hydroxy-7-methanesulfonyl-2-methyl-1,1-dioxo-1,2-dihydro-2H-benzo[e][1,2]thiazin-3-yl)-naphthalen-2-yl-methanone

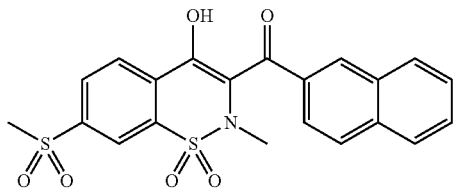 [SMILES: CN1C(C(=O)c2ccc3ccccc3c2)=C(O)c2ccc(S(C)(=O)=O)cc2S1(=O)=O]

EXAMPLE 170

(4-Hydroxy-7-methanesulfonyl-2-methyl-1,1-dioxo-1,2-dihydro-2H-benzo[e][1,2]thiazin-3-yl)-naphthalen-2-yl-methanone The compound 170 was synthesized from 5-methanesulfonyl-2-methyl-benzenesulfonyl chloride according to the same sequence of steps described for preparing the compound 17, with an overall yield of 7%.

HPLC: RT=5.43 min, 97%

¹H NMR, dmso-d₆, δ (ppm): 2.71 (s, 3H); 3.47 (s, 3H); 7.67 (t, 1H); 7.73 (t, 1H); 8.05-8.15 (m, 4H); 7.42-8.49 (m, 3H); 8.67 (s, 1H); 14.76 (se, 1H, exch).

Mass spectrum (ESI+): m/z 444 (MH+, 100%).

EXAMPLE 171

(4-Hydroxy-2-methyl-1,1-dioxo-1,2-dihydro-2H-benzo[e][1,2]thiazin-3-yl)-(1-phenyl-cyclopropyl)-methanone

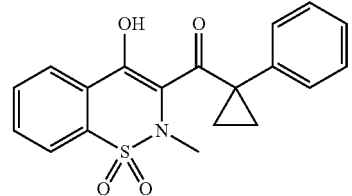 [SMILES: CN1C(C(=O)C2(c3ccccc3)CC2)=C(O)c2ccccc2S1(=O)=O]

EXAMPLE 171A 1-(1-Phenyl-cyclopropyl)-ethanone

The compound 171A was synthesized from 1-phenyl-cyclopropanecarbonitrile according to the same procedure described for preparing the compound 147B, with a yield of 40%.

HPLC: RT=4.30 min, 96% (XBridge column)

¹H NMR, dmso-d₆, δ (ppm): 1.15 (dd, 2H); 1.47 (dd, 1H); 1.92 (s, 3H); 7.23-7.40 (m, 5H).

Mass spectrum (ESI+): m/z 161 (MH⁺, 100%).

EXAMPLE 171

(4-Hydroxy-2-methyl-1,1-dioxo-1,2-dihydro-2H-benzo[e][1,2]thiazin-3-yl)-(1-phenyl-cyclopropyl)-methanone The compound 171 was synthesized from the compound 171A according to the same sequence of steps described for preparing the compound 144, with an overall yield of 6%.

HPLC: RT=6.40 min, 96% (XBridge column)

$^1$H NMR, dmso-d$_6$, δ (ppm): 1.38-1.41 (m, 2H); 1.65-1.68 (m, 2H); 2.46 (s, 3H); 7.25-7.37 (m, 5H); 7.78-7.83 (m, 1H); 7.86-7.91 (m, 2H); 8.06-8.08 (m, 1H), 15.31 (s, 1H, exch).

Mass spectrum (ESI+): m/z 356 (MH$^+$, 100%).

EXAMPLE 172

1-[3-(4-Hydroxy-2-methyl-1,1-dioxo-1,2-dihydro-2H-benzo[e][1,2]thiazine-3-carbonyl)-phenyl]-ethanone

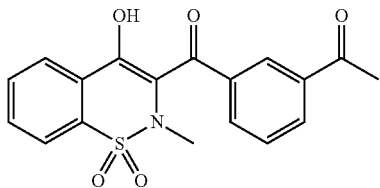 [SMILES: CC(=O)c1cccc(C(=O)C2=C(O)c3ccccc3S(=O)(=O)N2C)c1]

EXAMPLE 172

1-[3-(4-Hydroxy-2-methyl-1,1-dioxo-1,2-dihydro-2H-benzo[e][1,2]thiazine-3-carbonyl)-phenyl]-ethanone The compound 172 was synthesized from 1-(3-acetyl-phenyl)-ethanone according to the same sequence of steps described for preparing the compound 144, with an overall yield of 21%.

HPLC: RT=6.25 min, 97% (XBridge column)

$^1$H NMR, dmso-d$_6$, δ (ppm): 2.64 (s, 3H); 2.66 (s, 3H); 7.79 (t, 1H); 8.00 (broad s, 3H); 8.15-8.35 (m, 3H); 8.58 (s, 1H); 15.21 (broad s, 1H, exch).

Mass spectrum (ESI-): m/z 356 (M-H$^-$, 100%).

EXAMPLE 173

(4-Hydroxy-2-methyl-1,1-dioxo-1,2-dihydro-2H-benzo[e][1,2]thiazin-3-yl)-[3-(2,2,2-trifluoro-1-hydroxy-1-methyl-ethyl)-phenyl]-methanone

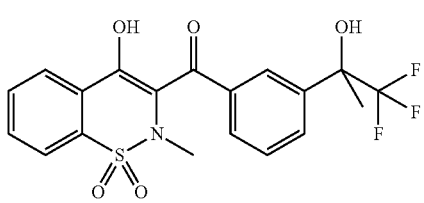 [SMILES: CN1C(C(=O)c2cccc(C(C)(O)C(F)(F)F)c2)=C(O)c2ccccc2S1(=O)=O]

EXAMPLE 173A

1-[3-(2,2,2-Trifluoro-1-hydroxy-1-methyl-ethyl)-phenyl]-ethanone 1-(3-acetyl-phenyl)-ethanone (2.5 g, 15.4 mmol) is dissolved in 120 mL of THF under a nitrogen atmosphere and at 0° C. in the presence of TMS-CF$_3$ (2.7 mL, 18.4 mmol). TBAF (1M/THF, 18.4 mL, 18.4 mmol) is added within 20 minutes by means of a syringe pump. The cold bath is removed and the reaction medium is stirred for a further 18 hours and then neutralized by adding a saturated NaHCO$_3$ solution, and finally extracted 3 times with ethyl acetate. The organic phases are combined, washed with water and then dried on magnesium sulfate, filtered and concentrated under reduced pressure. The thereby obtained residue is purified on silica (gradient of 0% to 50% ethyl acetate in heptane in 20 min), in order to obtain the partly purified compound 173A (2.87 g). It is used as such in the next step.

EXAMPLE 173B

2-Bromo-1-[3-(2,2,2-trifluoro-1-hydroxy-1-methyl-ethyl)-phenyl]-ethanone

The compound 173B was synthesized from the compound 173A according to the procedure for preparing the compound 144A, with a yield of 57%.

HPLC: RT=5.50 min, 74% (XBridge column)

$^1$H NMR, dmso-d$_6$, δ (ppm): 1.73 (s, 3H); 4.96 (s, 2H); 6.81 (broad s, 1H, exch); 7.60 (t, 1H); 7.89 (d, 1H); 8.03 (d, 1H); 8.17 (s, 1H).

EXAMPLE 173

(4-Hydroxy-2-methyl-1,1-dioxo-1,2-dihydro-2H-benzo[e][1,2]thiazin-3-yl)-[3-(2,2,2-trifluoro-1-hydroxy-1-methyl-ethyl)-phenyl]-methanone The compound 173 was synthesized from saccharin and from the compound 173B according to the same sequence of steps described for preparing the compound 1, with an overall yield of 52%.

HPLC: RT=6.05 min, 95% (XBridge column)

$^1$H NMR, dmso-d$_6$, (ppm): 1.76 (s, 3H); 2.61 (s, 3H); 6.84 (s, 1H, exch); 7.67 (t, 1H); 7.90-8.05 (m, 5H); 8.17-8.23 (m, 1H); 8.36 (s, 1H); 15.47 (broad s, 1H, exch).

Mass spectrum (ESI+): m/z 445 (MNH$_4^+$, 100%).

EXAMPLE 174

(4-Hydroxy-2-methyl-1,1-dioxo-1,2-dihydro-2H-benzo[e][1,2]thiazin-3-yl)-[3-(2,2,2-trifluoro-1-hydroxy-ethyl)-phenyl]-methanone

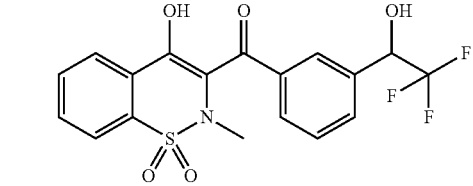 [SMILES: CN1C(C(=O)c2cccc(C(O)C(F)(F)F)c2)=C(O)c2ccccc2S1(=O)=O]

EXAMPLE 174A

1-[3-(2,2,2-Trifluoro-1-trimethylsilanyloxy-ethyl)-phenyl]-ethanone 3-acetylbenzaldehyde (1.27 g, 8.57 mmol) is dissolved in 30 mL of DMF under a nitrogen atmosphere in the presence of potassium carbonate (59 mg, 0.42 mmol) and of TMS-CF$_3$ (1.52 mL, 10.3 mmol). The reaction mixture is stirred for 30 minutes at room temperature and then neutralized with 1 mL of a saturated NH$_4$Cl solution and concentrated under reduced pressure. The residue is taken up in ethyl acetate and then washed once with HCl (1N in water), dried on magnesium sulfate, filtered and concentrated under reduced pressure in order to obtain the partly purified compound 174A (2.55 g). It is used as such in the next step.

HPLC: RT=5.15 min, 42% (OH) et 6.91 min, 40% (OTMS) (XBridge column, partial deprotection on the column).

$^1$H NMR, dmso-d$_6$, δ (ppm): 0.09 (s, 9H); 2.60 (s, 3H); 5.60 (q, 1H); 7.60 (t, 1H); 7.76 (d, 1H); 8.02 (d, 1H); 8.08 (s, 1H).

Mass spectrum (ESI+): m/z 291 (MH$^+$, 100%).

EXAMPLE 174B

2-Bromo-1-[3-(2,2,2-trifluoro-1-hydroxy-ethyl)-phenyl]-ethanone

The compound 174B was synthesized from the compound 174A according to the procedure for preparing the compound 144A, with a yield of 60%.

HPLC: RT=5.23 min, 83% (XBridge column)

$^1$H NMR, dmso-d$_6$, δ (ppm): 4.93 (s, 2H); 5.32 (q, 1H); 7.03 (broad s, 1H, exch); 7.61 (t, 1H); 7.81 (d, 1H); 8.05 (d, 1H); 8.11 (s, 1H).

EXAMPLE 174

(4-Hydroxy-2-methyl-1,1-dioxo-1,2-dihydro-2H-benzo[e][1,2]thiazin-3-yl)-[3-(2,2,2-trifluoro-1-hydroxy-ethyl)-phenyl]-methanone The compound 174 was synthesized from saccharin and from the compound 174B according to the same sequence of steps described for preparing the compound 1, with an overall yield of 33%.

HPLC: RT=5.92 min, 92% (XBridge column)

$^1$H NMR, dmso-d$_6$, δ (ppm): 2.60 (s, 3H); 5.32 (broad s, 1H); 7.05 (d, 1H, exch); 7.67 (t, 1H); 7.80 (d, 1H); 7.98 (broad s, 3H); 8.08 (d, 1H); 8.20 (broad s, 2H); 15.45 (broad s, 1H, exch).

Mass spectrum (ESI+): m/z 431 (MNH$_4^+$, 100%).

EXAMPLE 175

3-(4-Hydroxy-2-methyl-1,1-dioxo-1,2-dihydro-2H-benzo[e][1,2]thiazine-3-carbonyl)-benzoic acid

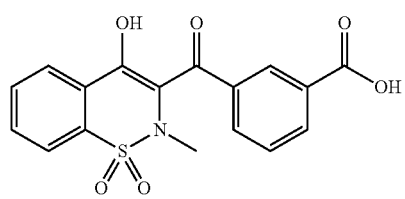 [SMILES: CN1C(C(=O)c2cccc(C(=O)O)c2)=C(O)c2ccccc2S1(=O)=O]

EXAMPLE 175

3-(4-Hydroxy-2-methyl-1,1-dioxo-1,2-dihydro-2H-benzo[e][1,2]thiazine-3-carbonyl)-benzoic acid The compound 143 (100 mg, 0.29 mmol) is dissolved in 1 mL of KOH (30% in water) in the presence of 330 μl of ethanol, and then heated to 70° C. for 18 hours. The reaction medium is diluted with 10 mL of water, washed twice with ether, brought back to pH=2 with an HCl (6N in water) and finally extracted three times with a solution of 20% methanol in DCM. The organic phases are combined, dried on magnesium sulfate, filtered and concentrated in order to obtain the compound 175 as a yellow solid (99 mg, 93%).

HPLC: RT=5.49 min, 98% (XBridge column)

$^1$H NMR, dmso-d$_6$, δ (ppm): 2.64 (s, 3H); 7.77 (t, 1H); 7.99-8.00 (m, 3H); 8.20-8.24 (m, 2H); 8.28 (d, 1H); 8.61 (s, 1H); 13.33 (s, exch, 1H); 15.32 (s, exch, 1H).

Mass spectrum (ESI−): m/z 358 (M-H$^−$, 100%).

EXAMPLE 176

3-(4-Hydroxy-2-methyl-1,1-dioxo-1,2-dihydro-2H-benzo[e][1,2]thiazine-3-carbonyl)-N-methyl-benzamide

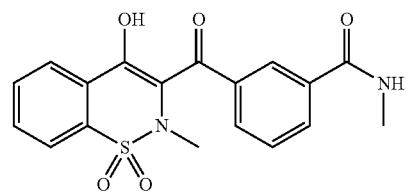 [SMILES: CNC(=O)c1cccc(C(=O)C2=C(O)c3ccccc3S(=O)(=O)N2C)c1]

EXAMPLE 176

3-(4-Hydroxy-2-methyl-1,1-dioxo-1,2-dihydro-2H-benzo[e][1,2]thiazine-3-carbonyl)-N-methyl-benzamide The compound 175 (150 mg, 0.41 mmol) is dissolved in 3 mL of DMF under an inert atmosphere in the presence of (3-dimethylamino-propyl)-ethyl-carbodiimide hydrochloride (120 mg, 0.62 mmol), of 3-hydroxy-3H-benzo[d][1,2,3]triazin-4-one (102 mg, 0.62 mmol) and iPr$_2$NEt (162 mg, 1.25 mmol), and then stirred at room temperature for 72 hours. The reaction mixture is concentrated under reduced pressure, diluted with 20 mL of DCM and washed twice with HCl (1N in water). The aqueous phases are collected and extracted DCM. The organic phases are combined, dried on magnesium sulfate, filtered and concentrated. The thereby obtained residue is purified on a column of 12 g of silica (12 mL/min, gradient of 0% to 25% acetone in DCM in 20 minutes), in order to obtain the compound 176 as a yellow solid (101 mg, 64%).

HPLC: RT=5.21 min, 97% (XBridge column)

$^1$H NMR, dmso-d$_6$, δ (ppm): 2.63 (s, 3H); 2.82 (d, 3H); 7.72 (t, 1H), 7.99 (d, 3H); 8.10 (d, 1H); 8.20-8.22 (m, 2H); 8.42 (s, 1H); 8.66 (d, 1H); 15.35 (broad s, 1H, exch).

Mass spectrum (ESI+): m/z 373 (MH$^+$, 100%).

EXAMPLES 177 TO 183

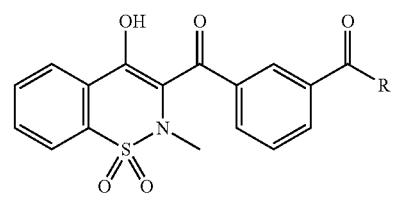

The compounds 177 to 183 were synthesized from the compound 175 and from various amines according to the same procedure described for preparing the compound 176.

| Ex.* | R | Name of the compounds | HPLC** | Yld. | MH+ |
|---|---|---|---|---|---|
| 177 | | 3-(4-Hydroxy-2-methyl-1,1-dioxo-1,2-dihydro-2H-benzo[e][1,2]thiazine-3-carbonyl)-N,N-dimethyl-benzamide | 5.33' 95.8% | 44% | 387 |
| 178 | | N-Ethyl-3-(4-hydroxy-2-methyl-1,1-dioxo-1,2-dihydro-2H-benzo[e][1,2]thiazine-3-carbonyl)-benzamide | 5.41' 96.9% | 39% | 387 |
| 179 | | 3-(4-Hydroxy-2-methyl-1,1-dioxo-1,2-dihydro-2H-benzo[e][1,2]thiazine-3-carbonyl)-N,N-diethyl-benzamide | 5.71' 96.9% | 34% | 415 |
| 180 | | N-Cyclopropyl-3-(4-hydroxy-2-methyl-1,1-dioxo-1,2-dihydro-2H-benzo[e][1,2]thiazine-3-carbonyl)-benzamide | 5.43' 96.6% | 33% | 399 |
| 181 | | N-Cyclopropylmethyl-3-(4-hydroxy-2-methyl-1,1-dioxo-1,2-dihydro-2H-benzo[e][1,2]thiazine-3-carbonyl)-benzamide | 5.71' 98.7% | 33% | 413 |
| 182 | | 3-(4-Hydroxy-2-methyl-1,1-dioxo-1,2-dihydro-2H-benzo[e][1,2]thiazine-3-carbonyl)-N-phenyl-benzamide | 6.09' 99.5% | 67% | 435 |
| 183 | | N-Benzyl-3-(4-hydroxy-2-methyl-1,1-dioxo-1,2-dihydro-2H-benzo[e][1,2]thiazine-3-carbonyl)-benzamide | 5.96' 93.8% | 6% | 449 |

*$^1$H NMR, dmso-$d_6$. Ex. 177: 2.65 (s, 3 H); 2.98 (s, 3 H); 3.03 (s, 3 H); 7.68-7.75 (m, 2 H); 7.99-8.07 (m, 4 H); 8.08 (d, 1 H); 8.20-8.21 (d, 1 H); 15.28 (broad s, exch, 1 H). Ex. 178: 1.15 (t, 3 H); 2.63 (s, 3 H); 3.29-3.36 (m, 2 H + $H_2O$); 7.71 (t, 1 H); 7.99-8.00 (m, 3 H); 8.12 (d, 1 H); 8.21-8.22 (m, 2 H); 8.42 (s, 1 H); 8.68 (t, 1 H); 15.36 (broad s, exch, 1 H). Ex. 179: 1.09-1.23 (m, 6 H); 2.64 (s, 3 H); 3.24-3.47 (m, 4 H + $H_2O$); 7.66-7.72 (m, 2 H); 7.95-8.08 (m, 5 H); 8.20-8.21 (m, 1 H); 15.28 (broad s, exch, 1 H). Ex. 180: 0.71-0.75 (m, 2 H); 0.8 (m, 2 H); 2.63 (s, 3 H); 2.86-2.91 (m, 1 H); 7.70 (t, 1 H); 7.99-8.00 (m, 3 H); 8.09 (d, 1 H); 8.20-5.21 (m, 2 H); 8.40 s (1 H); 8.66 (d, 1 H); 15.34 (broad s, exch, 1 H). Ex. 181: 0.45-0.47 (m, 2 H); 0.6 (m, 2 H); 1.06 (m, 1 H); 2.64 (s, 3 H); 3.18 (t, 2 H); 7.72 (t, 1 H); 7.99-8.00 (m, 3 H); 8.13 (d, 1 H); 8.21 (m, 2 H); 8.43 (s, 1 H); 8.78 (t, 1 H); 15.35 (broad s, exch, 1 H). Ex. 182: 2.66 (s, 3 H); 7.13 (t, 1 H); 7.38 (t, 2 H); 7.78-7.81 (m, 3 H); 8.00 (d, 3 H); 8.21-8.28 (m, 3 H); 8.52 (s, 1 H); 10.47 (s, 1 H); 15.33 (broad s, exch, 1 H). Ex. 183: 2.63 (s, 3 H); 4.52 (d, 2 H); 7.25-7.28 (m, 1 H); 7.32-7.36 (m, 4 H); 7.73 (t, 1 H); 8.00 (d, 3 H); 8.17-8.25 (m, 3 H); 8.49 (s, 1 H); 9.26-9.27 (m, 1 H); 15.34 (broad s, exch, 1 H).
** XBridge column.

EXAMPLE 184

3-(4-Hydroxy-2-methyl-1,1-dioxo-1,2-dihydro-2H-benzo[e][1,2]thiazine-3-carbonyl)-benzamide

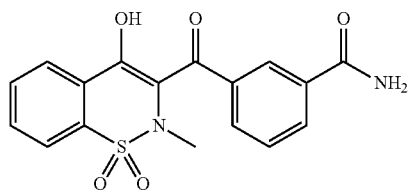 [SMILES: CN1C(C(=O)c2cccc(C(N)=O)c2)=C(O)c2ccccc2S1(=O)=O]

EXAMPLE 184

3-(4-Hydroxy-2-methyl-1,1-dioxo-1,2-dihydro-2H-benzo[e][1,2]thiazine-3-carbonyl)-benzamide The compound 175 (150 mg, 0.42 mmol) is dissolved in 3 mL of THF in the presence of PyBOP (239 mg, 0.46 mmol), of ammonia (152 µl, 1.25 mmol) and of DIEA (80 µl, 0.46 mmol) and stirred at room temperature for 4 hours. The reaction medium is diluted with 20 mL of DCM and washed with HCl (1N in water). The aqueous phase is extracted four times with DCM. The organic phases are combined, dried on magnesium sulfate, filtered and concentrated in order to obtain the compound 184 as a yellow solid (71 mg, 46%).

HPLC: RT=5.06 min, 97.4% (XBridge column)
$^1$H NMR, dmso-$d_6$, δ (ppm): 2.63 (s, 3H); 7.57 (s, 1H); 7.71 (t, 1H); 7.99 (d, 3H); 8.14-8.23 (m, 4H); 8.46 (s, 1H); 15.36 (broad s, exch, 1H).

Mass spectrum (ESI+): m/z 359 (MH+, 100%).

EXAMPLE 185

3-(4-Hydroxy-2-methyl-1,1-dioxo-1,2-dihydro-2H-benzo[e][1,2]thiazine-3-carbonyl)-benzoic acid ethyl ester

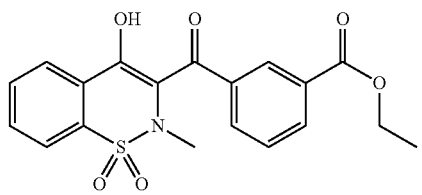 [SMILES: CCOC(=O)c1cccc(C(=O)C2=C(O)c3ccccc3S(=O)(=O)N2C)c1]

EXAMPLE 185

3-(4-Hydroxy-2-methyl-1,1-dioxo-1,2-dihydro-2H-benzo[e][1,2]thiazine-3-carbonyl)-benzoic acid ethyl ester The compound 175 (150 mg, 0.42 mmol) is dissolved in 6 mL ethanol in the presence of pTsOH (8 mg, 0.04 mmol), and refluxed with stirring for 18 hours. The reaction medium is concentrated under reduced pressure. The thereby obtained residue is purified on a column of 12 g of silica (12 mL/min, DCM), in order to obtain the compound 185 as a yellow solid (138 mg, 84%).

HPLC: RT=6.28 min, 95.8% (XBridge column)

$^1$H NMR, dmso-$d_6$, δ (ppm): 1.36 (t, 3H); 2.64 (s, 3H); 4.37 (q, 2H); 7.79 (t, 1H); 8.00 (d, 3H); 8.20-8.30 (m, 3H); 8.65 (s, 1H), 15.23 (broad s, exch, 1H).

Mass spectrum (ESI+): m/z 405 (MH$^+$, 100%).

EXAMPLE 186

(4-Hydroxy-2-methyl-1,1-dioxo-1,2-dihydro-2H-benzo[e][1,2]thiazin-3-yl)-(3-pyridin-3-yl-phenyl)-methanone

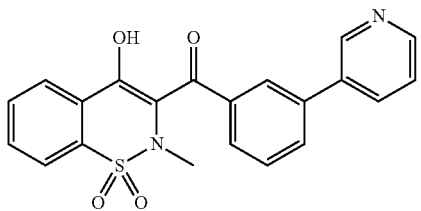 [SMILES: CN1C(C(=O)c2cccc(-c3cccnc3)c2)=C(O)c2ccccc2S1(=O)=O]

EXAMPLE 186

(4-Hydroxy-2-methyl-1,1-dioxo-1,2-dihydro-2H-benzo[e][1,2]thiazin-3-yl)-(3-pyridin-3-yl-phenyl)-methanone The compound 142 (200 mg, 0.5 mmol) is dissolved under an inert atmosphere in 1.5 mL of 1,4-dioxane in the presence of pyridin-3-ylboronic acid (104 mg, 0.76 mmol), of tripotassium orthophosphate (1.27 mol/l, 679 μl, 0.86 mmol), of tris(dibenzylideneacetone)dipalladium (23 mg, 0.025 mmol) and of tricyclo-hexylphosphine (21 mg, 0.076 mmol). The reaction medium is heated to 100° C. for 18 hours and then brought back to room temperature, diluted with DCM and washed with a saturated NH$_4$Cl solution. The organic phase is dried on magnesium sulfate, filtered and concentrated under reduced pressure. The thereby obtained residue is purified on a column of 12 g of silica (16 mL/min, gradient of 0% to 5% methanol in 7 min), in order to obtain the compound 186 (128 mg, 62%).

HPLC: RT=5.07 min, 97.5% (XBridge column)

$^1$H NMR, dmso-$d_6$, (ppm): 2.67 (s, 3H); 7.77-7.82 (m, 3H); 7.98-8.01 (m, 3H); 8.11-8.15 (m, 2H); 8.22 (dd, 1H); 8.39 (s, 1H); 8.71 (d, 2H); 15.20 (broad s, 1H, exch).

Mass spectrum (ESI+): m/z 393 (MH$^+$, 100%).

EXAMPLES 187 TO 195

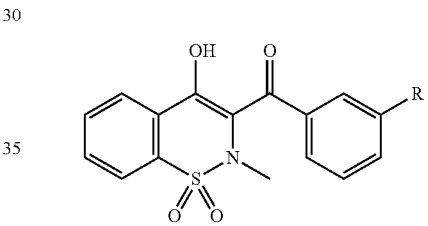

The compounds 187 to 195 were synthesized from the compound 144 and from various boronic acids according to the same method as described for preparing the compound 186.

| Ex.* | R | Name of the compounds | HPLC** | Yld. | M−H− (MH$^+$) |
|---|---|---|---|---|---|
| 187 | ![R group] | (4-Hydroxy-2-methyl-1,1-dioxo-1,2-dihydro-2H-benzo[e][1,2]thiazin-3-yl)-(3-pyridin-4-yl-phenyl)-methanone | 5.02' 97.5% | 62% | 393 |
| 188 | 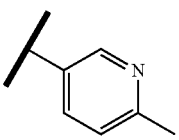 | (4-Hydroxy-2-methyl-1,1-dioxo-1,2-dihydro-2H-benzo[e][1,2]thiazin-3-yl)-[3-(6-methyl-pyridin-3-yl)-phenyl]-methanone | 5.04' 93% | 49% | 407 |

-continued

| Ex.* | R | Name of the compounds | HPLC** | Yld. | M − H−(MH+) |
|---|---|---|---|---|---|
| 189 | 5-methylpyridin-3-yl | (4-Hydroxy-2-methyl-1,1-dioxo-1,2-dihydro-2H-benzo[e][1,2]thiazin-3-yl)-[3-(5-methyl-pyridin-3-yl)-phenyl]-methanone | 5.09' 97.9% | 53% | 407 |
| 190 | 4-methylpyridin-3-yl | (4-Hydroxy-2-methyl-1,1-dioxo-1,2-dihydro-2H-benzo[e][1,2]thiazin-3-yl)-[3-(4-methyl-pyridin-3-yl)-phenyl]-methanone | 5.05' 98.1% | 60% | 407 |
| 191 | 2-methylpyridin-3-yl | (4-Hydroxy-2-methyl-1,1-dioxo-1,2-dihydro-2H-benzo[e][1,2]thiazin-3-yl)-[3-(2-methyl-pyridin-3-yl)-phenyl]-methanone | 5.02' 100% | 70% | 407 |
| 192 | 4-methoxypyridin-3-yl | (4-Hydroxy-2-methyl-1,1-dioxo-1,2-dihydro-2H-benzo[e][1,2]thiazin-3-yl)-[3-(4-methoxy-pyridin-3-yl)-phenyl]-methanone | 5.07' 100% | 21% | 423 |
| 193 | 6-fluoropyridin-3-yl | (4-Hydroxy-2-methyl-1,1-dioxo-1,2-dihydro-2H-benzo[e][1,2]thiazin-3-yl)-[3-(6-fluoro-pyridin-3-yl)-phenyl]-methanone | 6.28' 97.3% | 37% | 411 |
| 194 | 2-methoxypyridin-3-yl | (4-Hydroxy-2-methyl-1,1-dioxo-1,2-dihydro-2H-benzo[e][1,2]thiazin-3-yl)-[3-(2-methoxy-pyridin-3-yl)-phenyl]-methanone | 6.41' 96.9% | 63% | 423 |
| 195 | 6-methoxypyridin-3-yl | (4-Hydroxy-2-methyl-1,1-dioxo-1,2-dihydro-2H-benzo[e][1,2]thiazin-3-yl)-[3-(6-methoxy-pyridin-3-yl)-phenyl]-methanone | 6.35' 97.5% | 27% | 423 |

*$^1$H NMR, dmso-d$_6$, Ex. 187: 2.67 (s, 3 H); 7.77-7.82 (m, 3 H); 7.98-8.01 (m, 3 H); 8.11-8.15 (m, 2 H); 8.22 (dd, 1 H); 8.39 (s, 1 H); 8.71 (d, 2 H); 15.20 (broad s, 1 H, exch). Ex. 188: 2.54 (s, 3 H); 2.67 (s, 3 H); 7.41 (d, 1 H); 7.75 (t, 1 H); 7.98-8.07 (m, 6 H); 8.19-8.23 (m, 1 H); 8.31 (s, 1 H); 8.82 (s, 1 H); 15.28 (broad s, 1 H, exch). Ex. 189: 2.40 (s, 3 H); 2.97 (s, 3 H); 7.76 (t, 1 H); 7.98-8.09 (m, 6 H); 8.19-8.24 (m, 1 H); 8.32 (s, 1 H); 8.48 (s, 1 H); 8.76 (s, 1 H); 15.25 (broad s, 1 H, exch). Ex. 190: 2.35 (s, 3 H); 2.68 (s, 3 H); 7.42 (d, 1 H); 7.76 (d, 2 H); 7.97-8.07 (m, 5 H); 8.19-8.23 (m, 1 H); 8.46 (s, 1 H); 8.49 (d, 1 H); 15.35 (broad s, 1 H, exch). Ex. 191: (CDCl$_3$) 2.58 (s, 3 H); 2.74 (s, 3 H); 7.24 (dd, 1 H); 7.51-7.64 (m, 3 H); 7.78-7.84 (m, 2 H); 7.91-7.96 (m, 1 H); 8.10 (s, 1 H); 8.19-8.23 (m, 2 H); 8.56 (dd, 1 H); 15.75 (s, 1 H, exch). Ex. 192: 2.70 (s, 3 H); 3.93 (s, 3 H); 7.24 (d, 1 H); 7.69 (t, 1 H); 7.82 (d, 1 H); 7.96-8.00 (m, 4 H); 8.17-8.21 (m, 1 H); 8.27 (s, 1 H); 8.45 (s, 1 H); 8.51 (d, 1 H); 15.48 (broad s, 1 H, exch). Ex. 193: 2.67 (s, 3 H); 7.37 (dd, 1 H); 7.77 (t, 1 H); 8.00 (broad s, 3 H); 8.04-8.11 (m, 2 H); 8.19-8.23 (m, 1 H); 8.29 (s, 1 H); 8.32-8.39 (td, 1 H); 8.32 (s, 1 H); 15.24 (broad s, 1 H, exch). Ex. 194: 2.70 (s, 3 H); 3.95 (s, 3 H); 7.16 (dd, 1 H); 7.70 (t, 1 H); 7.82-7.89 (m, 2 H); 7.98-8.03 (m, 4 H); 8.17-8.24 (m, 2 H); 8.37 (s, 1 H); 15.53 (broad s, 1 H, exch). Ex. 195: 2.67 (s, 3 H); 3.92 (s, 3 H); 6.98 (d, 1 H); 7.73 (t, 1 H); 7.99-8.05 (m, 5 H); 8.09 (dd, 1 H); 8.21 (broad s, 1 H); 8.28 (s, 1 H); 8.55 (s, 1 H); 15.30 (broad s, 1 H, exch).

**XBridge column.

EXAMPLES 196 AND 197

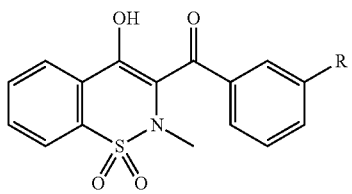

The compounds 196 and 197 were synthesized from saccharin and from 2-bromo-1-(3-chlorophenyl)ethanone and 2-bromo-1-(3-fluorophenyl)ethanone respectively according to the same method described for preparing the compound 1.

| Ex.* | R | Name of the compounds | HPLC** | Yld.[1] | M-H⁻ |
|---|---|---|---|---|---|
| 196 | Cl | (3-Chloro-phenyl)-(4-hydroxy-2-methyl-1,1-dioxo-1,2-dihydro-2H-benzo[e][1,2]thiazin-3-yl)-methanone | 6.43' 98.7% | 37% | 348/350 |
| 197 | F | (3-Fluoro-phenyl)-(4-hydroxy-2-methyl-1,1-dioxo-1,2-dihydro-2H-benzo[e][1,2]thiazin-3-yl)-methanone | 6.14' 96.5% | 19% | 332 |

[1]Overall yield for the 3 steps.
* ¹H NMR, dmso-d₆, Ex. 196: 2.66 (s, 3H); 7.67 (t, 1H); 7.78 (d, 1H); 7.99 (s, 5H); 8.15 (broad s, 1H); 15.07 (broad s, 1H, exch.). Ex. 197: 2.65 (s, 3H); 7.58 (t, 1H); 7.70 (dd, 1H); 7.76 (d, 1H); 7.90 (d, 1H); 7.99 (broad s, 3H); 8.20 (broad s, 1H); 15.15 (broad s, 1H, exch.).
** XBridge column.

The derivatives of the present invention are selective inhibitors of 11-HSD1 relatively to 11-HSD2 as shown by the results of the models described below:

1) Human Enzymatic Activity of 11β-HSD1 from Liver Microsomes after Treatment with Inhibitor Compounds (Inhibition %).

The enzymatic test is based on the conversion of cortisone into cortisol by 11β-HSD1. The enzymatic reaction is started by adding 1 μg of human hepatic microsome (Xenotech) to wells (half volume 96-well plates, reaction volume of 50 μL) containing 160 nM of cortisone in a Tris 20 mM buffer (pH 7.4) with 5 mM EDTA, 200 μM NADPH and the inhibitor compound or the carrier (1% DMSO). A calibration curve of known cortisol concentrations is produced simultaneously under the same experimental conditions. The plates are incubated for 2 hours at 37° C. (enzymatic phase). By adding 25 μL of conjugate cortisol-d2 and of 25 μL of anti-cortisol anαtibody labeled with Eu³⁺ cryptate per well, the enzymatic reaction may be stopped and after incubation of 2 hours at room temperature the formed cortisol (detection phase) may be quantified by HTRF® (CIS bio international, reference 62CO2PEC). The fluorescence measurements are conducted with a Fusion™ α(Perkin Elmer) reader. For each well, fluorescence is measured at 620 nm and at 665 nm. A ratio (λ665 nm/λ620 nm) and a specific FRET signal are calculated, with which an inhibition percentage may be determined for each concentration of evaluated inhibitor compound.

REFERENCES

Posters $IC_{50}$ determination of Carbenoxolone and Glycyrrhetinic acid on 11-beta hydroxysteroid dehydrogenase type 1 activity by HTRF®: C. Tokuda et al., Screentech, March 2004, San Diego (USA).

New Cortisol assay for 11-beta hydroxysteroid dehydrogenase type 1 activity using a new HTRF® acceptor, d2: M. Amoravain et al., SBS, 12th Annual Conference, September 2006, Seattle (USA).

2) Human Enzymatic Activity of 11β-HSD1 from Liver Microsomes after Treatment with Inhibitor Compounds (Inhibition % or $EC_{50}$).

The enzymatic test is based on the conversion of [³H] cortisone into [³H] cortisol by 11β-HSD1. The enzymatic reaction is stated by adding 1 μg (standardization of this amount in order to obtain 80% of the substrate conversion maximum under the experimental conditions) of human hepatic microsomes (Xenotech) to wells (Optiplate™ 96-well plates, reaction volume of 50 μL) containing 20 nM of [1,2-³H] cortisone (specific activity of 40-50 Ci/mmol, Amersham-GE Healthcare) in a 50 mM HEPES buffer at (pH 7.4) with 100 mM KCl, 5 mM NaCl, 2 mM MgCl₂, 1 mM NADPH and the inhibitor compound or the carrier (1% DMSO). The sealed plates are centrifuged at low speed for mixing the components and then incubated for 2 hours at 37° C. (enzymatic phase). The enzymatic reaction is stopped by adding 70 μl/well of complex [10 mg/mL of yttrium silicate SPA beads associated with the protein A (GE Healthcare) and pre-incubated with an anti-cortisol monoclonal antibody (East Coast Biologics, ME)] containing 10 μM of 18β-glycerrhitinic acid. The plates are sealed and then incubated under slow orbital stirring for 2 hours at room temperature (detection phase). After centrifugation, measurements are conducted with a scintillation counter (TopCount NXT Perkin Elmer). A percentage of inhibition for each evaluated compound concentration is calculated relatively to the standard enzymatic activity (carrier 1% DMSO) with which the potential of each compound may then be determined ($EC_{50}$ obtained by the software SigmaPlot v.11, a logistic equation with 4 parameters).

REFERENCES

Development and application of a scintillation proximity assay (SPA) for identification of selective inhibitors of 11β-hydroxysteroid dehydrogenase type 1: S. Mundt et al., ASSAY and Drug Development Technologies, volume 3, number 4, 367-375, 2005.

High-throughput screening of 11β-hydroxysteroid dehydrogenase type 1 in scintillation proximity assay format: K. Solly et al., ASSAY and Drug Development Technologies, volume 3, number 4, 377-384, 2005.

3) Human Enzymatic Activity of 11β-HSD2 from Kidney Microsomes after Treatment with the Inhibitor Compounds (Inhibition %).

The enzymatic test is based on the conversion of [³H] cortisol into [³H] cortisone by 11β-HSD2. The enzymatic reaction is started by adding 0.75 μg (standardization of this amount in order to obtain 80% of the conversion maximum of the substrate under the experimental conditions) of human kidney microsomes (Xenotech) to wells (Optiplate™ 96-well plates, a reaction volume of 50 μL) containing 8 nM [1,2,6,7-³H] cortisol (specific activity of 70-75 Ci/mmol, Amersham-GE Healthcare) in a 50 mM HEPES buffer (pH 7.4) with 100 mM KCl, 5 mM NaCl, 2 mM MgCl₂, 1 mM NAD⁺ and the inhibitor compound or the carrier (1% DMSO). The sealed plates are centrifuged at low speed in order to mix the components and then incubated for 2 hours at 37° C. (enzymatic phase). The enzymatic reaction is stopped by adding 70 μl/well of complex [10 mg/mL of yttrium silicate SPA beads associated with protein A (GE Healthcare) and pre-incubated with an anti-cortisol monoclonal antibody (East Coast Biologics, ME)] containing 10 μM of 18β-glycerrhitinic acid. The plates are sealed and then incubated under slow orbital stirring for 2 hours at room temperature (detection phase). After centrifugation, the measurements are conducted with a scintillation counter TopCount NXT (Perkin Elmer). An inhibition percentage for each evaluated compound concentration is calculated relatively to the standard enzymatic activity (carrier 1% DMSO).

REFERENCES

Development and application of a scintillation proximity assay (SPA) for identification of selective inhibitors of 11β-hydroxysteroid dehydrogenase type 1: S. Mundt et al., ASSAY and Drug Development Technologies, volume 3, number 4, 367-375, 2005.

High-throughput screening of 11β-hydroxysteroid dehydrogenase type 1 in scintillation proximity assay format: K. Solly et al., ASSAY and Drug Development Technologies, volume 3, number 4, 377-384, 2005.

Results:

The few examples which follow, selected from compounds of the present invention, illustrate the quite unexpected capability of these compounds of selectively inhibiting 11β-HSD1 relatively to 11β-HSD2:

| Exemples | 11β-HSD1/HTRF % inhib. ($10^{-6}$M) | 11β-HSD1/SPA | | 11β-HSD2/SPA % inhib. ($10^{-5}$M) |
|---|---|---|---|---|
| | | % inhib. ($10^{-6}$M) | $EC_{50}$ (nM) | |
| 1 | 99 | 97 | 16 | 42 |
| 3 | 99 | 93 | 64 | 33 |
| 9 | 98 | 88 | 60 | 5 |
| 17 | 100 | 99 | 11 | 61 |
| 18 | 100 | 91 | 69 | 25 |
| 46 | 100 | 91 | 72 | 63 |
| 54 | 100 | 97 | 27 | 71 |
| 123 | 100 | 93 | 43 | 31 |
| 142 | 100 | 87 | 21 | — |
| 192 | 100 | 98 | 17 | — |

The object of the present invention is the compounds of general formula (I) or one of their stereoisomers or one of their salts acceptable for pharmaceutical use, for their use as a drug.

The object of the present invention is also the pharmaceutical compositions containing as an active ingredient a compound of general formula (I) or one of its stereoisomers, or one of its salts acceptable for pharmaceutical use in association with a pharmaceutically acceptable carrier, as drugs. These compositions may for example assume the form of solid, liquid compositions, emulsions, lotions or creams.

These pharmaceutical compositions containing as an active ingredient a compound of general formula (I) or one of their stereoisomers or one of their salts acceptable for pharmaceutical use may be used for inhibiting 11β-hydroxysteroid dehydrogenase type 1 (11βHSD1).

These pharmaceutical compositions containing as an active ingredient a compound of general formula (I) or one of its stereoisomers or one of its salts acceptable for pharmaceutical use for both curative and preventive treatment of diabetes of type 2.

These pharmaceutical compositions containing as an active ingredient a compound of general formula (I) or one of its stereoisomers or one of its salts acceptable for pharmaceutical use for both curative and preventive treatment of disorders related to the type 1 11β-hydroxysteroid dehydrogenase (11βHSD1); or obesity; or dyslipidemias; or arterial hypertension; or atherosclerosis and clinical pathologies which result therefrom such as coronary strokes, or cerebro-vascular strokes, or arteritis of the lower limbs; or hyperglycemias; of intolerance to glucose; or insulin-resistance; or hypertriglyceridemias; or hypercholesterolemias; or restenoses, or pancreatitises; or retinopathies; or nephropathies; or neuropathies; or certain types of cancer or glaucomas.

These compositions may be administered in association with an anti-diabetic such as biguanides (for example metformine), various forms of insulin, sulfonylureas (for example carbutamide, glibornuride, glipizide, gliclazide, glibenclamide, glimepiride), meglitinides (for example nateglinide, repaglinide, mitiglinide), PPAR modulators (for example pioglitazone), inhibitors of alpha-glucosidase (for example acarbose, miglitol, voglibose), GLP-1 analogs (for example exenatide, liraglutide), DPP-4 inhibitors (for example sitagliptin, vildagliptin), analogs of amyline (for example pramLintide).

These compositions may also be administered in association with an anti-obesity agent such as for example orlistat or sibutramine.

As solid compositions for oral administration, tablets, pills, powders (gelatin capsules, tablets) or granules may be used. In these compositions, the active ingredient according to the invention is mixed with one or more inert diluents such as starch, cellulose, saccharose, lactose or silica, under an argon stream. These compositions may also comprise substances other than diluents, for example one or more lubricants such as magnesium stearate or talc, a coloring agent, a coating (dragees) or a varnish.

As liquid compositions for oral administration, pharmaceutically acceptable solutions, suspensions, emulsions, syrups and elixirs containing inert diluents such as water, ethanol, glycerol, vegetable oils or paraffin oil may be used. These compositions may comprise substances other than diluents, for example wetting products, sweeteners, thickeners, flavoring agents or stabilizers.

The sterile compositions for parenteral administration may preferably aqueous or non-aqueous solutions, suspensions or emulsions. As a solvent or carrier, water, propyleneglycol, polyethyleneglycol, vegetable oils, in particular olive oil, injectable organic esters for example ethyl oleate or other suitable organic solvents may be used. These compositions may also contain adjuvants, in particular wetting, isotonizing, emulsifying, dispersing and stabilizing agents. Sterilization may be accomplished in several ways, for example by aseptizing filtration, by incorporating to the composition sterilizing agents, by irradiation or by heating. They may also be prepared as sterile solid compositions which may be dissolved at the moment of use in sterile water or any other injectable sterile medium.

The compositions for rectal administration are suppositories or rectal capsules which contain in addition to the active product, excipients such as cocoa butter, semi-synthetic glycerides or polyethyleneglycols.

The compositions for topical administration may for example be creams, lotions, collyria, collutories, nasal drops or aerosols.

The doses depend on the sought effect, on the duration of the treatment and on the administration route used; they are generally comprised between 0.001 g and 1 g (preferably comprised between 0.005 g and 0.75 g) per day preferably orally for an adult with unit doses ranging from 0.1 mg to 500 mg of active substance. Generally, the physician will determine the suitable dosage depending on the age, the weight and all the other factors specific to the subject to be treated.

The invention claimed is:
1. Compounds fitting general formula (I):

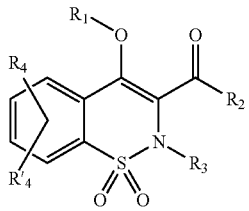

wherein:
R$_1$ represents: hydrogen; C$_1$-C$_6$ alkyl; COR$_5$; SO$_2$R$_5$; CO(CH$_2$)$_m$R$_6$; CO(CH$_2$)$_m$OR$_6$; (CH$_2$)$_m$R$_6$; (CH$_2$)$_m$CONR$_7$R$_8$; (CH$_2$)$_n$NR$_7$R$_8$; (CH$_2$)$_n$OR$_6$; CHR$_7$OR$_9$; or (CH$_2$)$_m$R$_{10}$,
m represents: 1 to 6,
n represents: 2 to 6,
R$_2$ represents: phenyl substituted with one or more groups selected from a halogen, C$_1$-C$_6$ alkyl, CN, OH, CF$_3$, OCF$_3$, SMe, COMe, CMe(OH)CF$_3$, CH(OH)CF$_3$, COOR$_7$, CONR$_7$R$_{11}$; a naphthyl, 1,2,3,4-tetrahydronaphthalene, biphenyl, phenyl pyridine or pyridine in the case where R$_1$, R$_4$ and R'$_4$ represent a hydrogen, either non-substituted or substituted with one or more groups selected from a halogen, C$_1$-C$_6$ alkyl, CN, OH, CF$_3$, OCF$_3$, OMe, SMe; a cycloalkyl either non-substituted or substituted with OH, CONH$_2$, SO$_2$Me, SO$_2$NH$_2$; C$_1$-C$_6$ alkyl aryl or cycloalkyl aryl, wherein R$_2$ is always bound to the carbonyl through a carbon atom and if R$_2$ is phenyl substituted with COOR$_7$, COOR$_7$ is not in position 4 relative to the carbonyl bonded to R$_2$,
R$_3$ represents: methyl or ethyl,
R$_4$ and R'$_4$, either identical or different, represent: hydrogen; halogen; C$_1$-C$_6$ alkyl; CN; CF$_3$; OCF$_3$; SMe; OMe; NR$_7$R$_8$; SO$_2$Me,
R$_5$ represents: C$_1$-C$_6$ alkyl; phenyl either non-substituted or substituted with one or more groups selected from halogen, C$_1$-C$_6$ alkyl, CN, OH, CF$_3$, OCF$_3$, SMe; a naphthyl, either non-substituted or substituted with one or more groups selected from halogen or C$_1$-C$_6$ alkyl, CN, OH, CF$_3$, OCF$_3$, SMe; a cycloalkyl either non-substituted or substituted with a CONH$_2$, SO$_2$Me, SO$_2$NH$_2$, heteroaryl either non-substituted or substituted with one or more groups selected from halogen, C$_1$-C$_6$ alkyl, CN, OH, CF$_3$, OCF$_3$, SMe,
R$_6$ represents: hydrogen; C$_1$-C$_6$ alkyl; phenyl either non-substituted or substituted with one or more groups selected from halogen, C$_1$-C$_6$ alkyl, CN, OH, CF$_3$, OCF$_3$, SMe; a naphthyl or heterocycle, either non-substituted or substituted with one or more groups selected from halogen or C$_1$-C$_6$ alkyl, CN, OH, CF$_3$, OCF$_3$, SMe; a cycloalkyl either non-substituted or substituted with CONH$_2$, SO$_2$Me, SO$_2$NH$_2$,
R$_7$ represents: hydrogen, C$_1$-C$_6$ alkyl,
R$_8$ represents: hydrogen, C$_1$-C$_6$ alkyl, phenyl either non-substituted or substituted with one or more groups selected from halogen, C$_1$-C$_6$ alkyl, CN, OH, CF$_3$, OCF$_3$, SMe; a naphthyl or heterocycle, either non-substituted or substituted with one or more groups selected from halogen, C$_1$-C$_6$ alkyl, CN, OH, CF$_3$, OCF$_3$, SMe; a cycloalkyl either non-substituted or substituted with CONH$_2$, SO$_2$Me, SO$_2$NH$_2$, R$_7$ and R$_8$ taken together may form a cycle of 4 to 6 members with the nitrogen atom to which they are bound and which may contain one or more heteroatoms selected from N, S or O and may either be non-substituted or substituted with one or more groups selected from C$_1$-C$_6$ alkyl, C$_1$-C$_6$ alkyl aryl or aryl,
R$_9$ represents: COOMe, COOEt,
R$_{10}$ represents: halogen, COOH, COOR$_7$, and
R$_{11}$ represents: hydrogen, C$_1$-C$_6$ alkyl, C$_1$-C$_6$ alkyl cycloalkyl, cycloalkyl, aryl, C$_1$-C$_6$ alkyl aryl,
as well as, stereoisomers and salts thereof acceptable for therapeutic use.
2. The compounds according to claim 1, wherein R$_1$ is a hydrogen.
3. The compounds according to claim 1, wherein OR$_1$ represents an ester or an ether.
4. The compounds according to any of claims 1 to 3, wherein R$_2$ represents a naphthyl or a 1,2,3,4-tetrahydronaphthalene or a biphenyl or a phenyl pyridine either non-substituted or substituted with one or more groups selected from a halogen, C$_1$-C$_6$ alkyl, CN, OH, CF$_3$, OCF$_3$, OMe, SMe; or a phenyl substituted with one or more halogens, CN, CF$_3$ or C$_1$-C$_6$ alkyl.
5. The compounds according to any of claims 1 to 3, wherein R$_4$ and R'$_4$ represent a hydrogen.
6. A compound selected from:
(4-Hydroxy-2-methyl-1,1-dioxo-2H-benzo[e][1,2]thiazin-3-yl)(naphthalen-2-yl)methanone: (4-Hydroxy-2-methyl-1,1-dioxo-2H-benzo[e][1,2]thiazin-3-yl)(adamantan-1-yl)methanone:
(4-Hydroxy-2-methyl-1,1-dioxo-2H-benzo[e][1,2]thiazin-3-yl)(4-methylphenyl)methanone:
(4-Hydroxy-2-methyl-1,1-dioxo-2H-benzo[e][1,2]thiazin-3-yl)(4-chlorophenyl)methanone:
(4-Hydroxy-2-methyl-1,1-dioxo-2H-benzo[e][1,2]thiazin-3-yl)(4-cyanophenyl)methanone;
Biphenyl-4-yl-(4-hydroxy-2-methyl-1,1-dioxo-2H-benzo[e][1,2]thiazin-3-yl)methanone;
(4-Hydroxy-2-methyl-1,1-dioxo-2H-benzo[e][1,2]thiazin-3-yl)(2,4-dichlorophenyl)methanone;
(4-Hydroxy-2-ethyl-1,1-dioxo-2H-benzo[e][1,2]thiazin-3-yl)(adamantan-1-yl)methanone;
(4-Hydroxy-2-ethyl-1,1-dioxo-2H-benzo[e][1,2]thiazin-3-yl)(naphthalen-2-yl)methanone;
(4-Hydroxy-2-ethyl-1,1-dioxo-2H-benzo[e][1,2]thiazin-3-yl)(4-methylphenyl)methanone;
(4-Hydroxy-2-ethyl-1,1-dioxo-2H-benzo[e][1,2]thiazin-3-yl)(4-chlorophenyl)methanone;
Biphenyl-4-yl-(4-hydroxy-2-ethyl-1,1-dioxo-2H-benzo[e][1,2]thiazin-3-yl)methanone;
(5-Chloro-4-hydroxy-2-methyl-1,1-dioxo-2H-benzo[e][1,2]thiazin-3-yl)(naphthalen-2-yl)methanone;
(5-Chloro-4-hydroxy-2-ethyl-1,1-dioxo-2H-benzo[e][1,2]thiazin-3-yl)(naphthalen-2-yl)methanone;
(6-Fluoro-4-hydroxy-2-methyl-1,1-dioxo-2H-benzo[e][1,2]thiazin-3-yl)(naphthalen-2-yl)methanone;
(6-Fluoro-4-hydroxy-2-ethyl-1,1-dioxo-2H-benzo[e][1,2]thiazin-3-yl)(naphthalen-2-yl)methanone;
(7-Fluoro-4-hydroxy-2-methyl-1,1-dioxo-2H-benzo[e][1,2]thiazin-3-yl)(naphthalen-2-yl)methanone;
(7-Fluoro-4-hydroxy-2-ethyl-1,1-dioxo-2H-benzo[e][1,2]thiazin-3-yl)(naphthalen-2-yl)methanone;
Benzoic acid 2-methyl-3-(naphthalene-2-carbonyl)-1,1-dioxo-2H-benzo[e][1,2]thiazin-4-yl ester;
Cyclohexanecarboxylic acid 2-methyl-3-(naphthalene-2-carbonyl)-1,1-dioxo-2H-benzo[e][1,2]thiazin-4-yl ester; tertButylcarboxylic acid 2-methyl-3-(naphthalene-2-carbonyl)-1,1-dioxo-2H-benzo[e][1,2]thiazin-4-yl ester;
4-Methylbenzoic acid 2-methyl-3-(naphthalene-2-carbonyl)-1,1-dioxo-2H-benzo[e][1,2]thiazin-4-yl ester;
4-Chlorobenzoic acid 2-methyl-3-(naphthalene-2-carbonyl)-1,1-dioxo-2H-benzo[e][1,2]thiazin-4-yl ester;
tertButylcarboxylic acid 16-fluoro-2-methyl-3-(naphthalene-2-carbonyl)-1,1-dioxo-2H-benzo[e][1,2]thiazin-4-yl ester;
Cyclohexanecarboxylic acid 6-fluoro-2-methyl-3-(naphthalene-2-carbonyl)-1,1-dioxo-2H-benzo[e][1,2]thiazin-4-yl ester;
Benzoic acid 6-fluoro-2-methyl-3-(naphthalene-2-carbonyl)-1,1-dioxo-2H-benzo[e][1,2]thiazin-4-yl ester;
4-Methylbenzoic acid 6-fluoro-2-methyl-3-(naphthalene-2-carbonyl)-1,1-dioxo-2H-benzo[e][1,2]thiazin-4-yl ester;
tertButylcarboxylic acid 6-fluoro-2-ethyl-3-(naphthalene-2-carbonyl)-1,1-dioxo-2H-benzo[e][1,2]thiazin-4-yl ester;
Cyclohexanecarboxylic acid 6-fluoro-2-ethyl-3-(naphthalene-2-carbonyl)-1,1-dioxo-2H-benzo[e][1,2]thiazin-4-yl ester;
Benzoic acid 6-fluoro-2-ethyl-3-(naphthalene-2-carbonyl)-1,1-dioxo-2H-benzo[e][1,2]thiazin-4-yl ester;
4-Methylbenzoic acid 6-fluoro-2-ethyl-3-(naphthalene-2-carbonyl)-1,1-dioxo-2H-benzo[e][1,2]thiazin-4-yl ester;
4-Chlorobenzoic acid 6-fluoro-2-methyl-3-(naphthalene-2-carbonyl)-1,1-dioxo-2H-benzo[e][1,2]thiazin-4-yl ester;
4-Chlorobenzoic acid 6-fluoro-2-ethyl-3-(naphthalene-2-carbonyl)-1,1-dioxo-2H-benzo[e][1,2]thiazin-4-yl ester;
Naphthalen-1-ylcarboxylic acid 2-methyl-3-(4-methylbenzoyl)-1,1-dioxo-2H-benzo[e][1,2]thiazin-4-yl ester;
Naphthalen-2-ylcarboxylic acid 2-methyl-3-(4-methylbenzoyl)-1,1-dioxo-2H-benzo[e][1,2]thiazin-4-yl ester;
Naphthalen-1-ylcarboxylic acid 2-methyl-3-(4-cyanobenzoyl)-1,1-dioxo-2H-benzo[e][1,2]thiazin-4-yl ester;
Naphthalen-2-ylcarboxylic acid 2-methyl-3-(4-cyanobenzoyl)-1,1-dioxo-2H-benzo[e][1,2]thiazin-4-yl ester;
4-Chlorobenzoic acid 2-methyl-3-(4-methylbenzoyl)-1,1-dioxo-2H-benzo[e][1,2]thiazin-4-yl ester;
4-Chlorobenzoic acid 2-methyl-3-(4-cyanobenzoyl)-1,1-dioxo-2H-benzo[e][1,2]thiazin-4-yl ester;
(Naphthalene-2-yloxy)acetic acid 2-methyl-3-(4-methylbenzoyl)-1,1-dioxo-2H-benzo[e][1,2]thiazin-4-yl ester;
(Naphthalene-2-yloxy)acetic acid 2-methyl-3-(4-cyanobenzoyl)-1,1-dioxo-2H-benzo[e][1,2]thiazin-4-yl ester;
(Naphthalene-1-yloxy)acetic acid 2-methyl-3-(4-methylbenzoyl)-1,1-dioxo-2H-benzo[e][1,2]thiazin-4-yl ester;
(Naphthalene-1-yloxy)acetic acid 2-methyl-3-(4-cyanobenzoyl)-1,1-dioxo-2H-benzo[e][1,2]thiazin-4-yl ester;
(4-Chlorophenoxy)acetic acid 2-methyl-3-(4-methylbenzoyl)-1,1-dioxo-2H-benzo[e][1,2]thiazin-4-yl ester;
(4-Chlorophenoxy)acetic acid 2-methyl-3-(4-cyanobenzoyl)-1,1-dioxo-2H-benzo[e][1,2]thiazin-4-yl ester;
Acetic acid 2-methyl-3-(naphthalene-2-carbonyl)-1,1-dioxo-2H-benzo[e][1,2]thiazin-4-yl ester;
2,4-Dichlorobenzoic acid 2-methyl-3-(naphthalene-2-carbonyl)-1,1-dioxo-2H-benzo[e][1,2]thiazin-4-yl ester;
4-Fluorobenzoic acid 2-methyl-3-(naphthalene-2-carbonyl)-1,1-dioxo-2H-benzo[e][1,2]thiazin-4-yl ester;
Cyclopentanoic acid 2-methyl-3-(naphthalene-2-carbonyl)-1,1-dioxo-2H-benzo[e][1,2]thiazin-4-yl ester;
2-Furanoic acid 2-methyl-3-(naphthalene-2-carbonyl)-1,1-dioxo-2H-benzo[e][1,2]thiazin-4-yl ester;
Thiophen-2-carboxylic acid 2-methyl-3-(naphthalene-2-carbonyl)-1,1-dioxo-2H-benzo[e][1,2]thiazin-4-yl ester;
3-Chlorobenzoic acid 2-methyl-3-(naphthalene-2-carbonyl)-1,1-dioxo-2H-benzo[e][1,2]thiazin-4-yl ester;
2-Chlorobenzoic acid 2-methyl-3-(naphthalene-2-carbonyl)-1,1-dioxo-2H-benzo[e][1,2]thiazin-4-yl ester
Phenoxyacetic acid 2-methyl-3-(naphthalene-2-ylcarbonyl)-1,1-dioxo-2H-benzo[e][1,2]thiazin-4-yl ester;
(4-Methoxy-2-methyl-1,1-dioxo-2H-benzo[e][1,2]thiazin-3-yl)(naphthalen-2-yl)methanone; (4-Ethoxy-2-methyl-1,1-dioxo-2H-benzo[e][1,2]thiazin-3-yl)(naphthalen-2-yl)methanone;
(4-Propyloxy-2-methyl-1,1-dioxo-2H-benzo[e][1,2]thiazin-3-yl)(naphthalen-2-yl)methanone;
(4-Butyloxy-2-methyl-1,1-dioxo-2H-benzo[e][1,2]thiazin-3-yl)(naphthalen-2-yl)methanone;
(4-(2-Chloroethoxy)-2-methyl-1,1-dioxo-2H-benzo[e][1,2]thiazin-3-yl)(p-tolyl)methanone;
(4-[2-(Naphthalen-2-yloxy)ethoxy]-2-methyl-1,1-dioxo-2H-benzo[e][1,2]thiazin-3-yl)(p-tolyl)methanone;
(4-(2-Phenoxy-ethoxy)-2-methyl-1,1-dioxo-2H-benzo[e][1,2]thiazin-3-yl)(naphthalen-2-yl)methanone;
Methyl 2-(2-methyl-3-(4-methylbenzoyl)-1,1-dioxo-2H-benzo[e][1,2]thiazin-4-yloxy)acetate;
2-(2-methyl-3-(4-methylbenzoyl)-1,1-dioxo-2H-benzo[e][1,2]thiazin-4-yloxy)acetic acid;
2-(2-Methyl-3-(4-methylbenzoyl)-1,1-dioxo-2H-benzo[e][1,2]thiazin-4-yloxy)-N-(naphthalen-1-yl)acetamide;
2-(2-Methyl-3-(4-methylbenzoyl)-1,1-dioxo-2H-benzo[e][1,2]thiazin-4-yloxy)-N-(adamantan-1-yl)acetamide;
2-(2-Methyl-3-(4-methylbenzoyl)-1,1-dioxo-2H-benzo[e][1,2]thiazin-4-yloxy)-N-(adamantan-2-yl)acetamide;
Methyl 2-(1,1-dioxo-2-methyl-3-(4-methylbenzoyl)-2H-benzo[e][1,2]thiazin-4-yloxy)acetate;
(1,1-dioxo-2-methyl-3-(4-methylbenzoyl)-2H-benzo[e][1,2]thiazin-4-yloxy) acetic acid;
2-[2-Methyl-3-(naphthalene-2-carbonyl)-1,1-dioxo-2H-benzo[e][1,2]thiazin-4-yloxy]-1-piperidin-1-yl-ethanone;
2-[2-Methyl-3-(naphthalene-2-carbonyl)-1,1-dioxo-2H-benzo[e][1,2]thiazin-4-yloxy]-1-(4-methyl-piperazin-1-yl)-ethanone;
1-(4-Benzyl-piperazin-1-yl)-2-[2-methyl-3-(naphthalene-2-carbonyl)-1,1-dioxo-2H-benzo[e][1,2]thiazin-4-yloxy]-ethanone;
(4-Chloro-phenoxy)-acetic acid 2-methyl-3-(naphthalene-2-carbonyl)-1,1-dioxo-2H-benzo[e][1,2]thiazin-4-yl ester;
(Naphthalen-1-yloxy)-acetic acid 2-methyl-3-(naphthalene-2-carbonyl)-1,1-dioxo-2H-benzo[e][1,2]thiazin-4-yl ester;
(Naphthalen-2-yloxy)-acetic acid 2-methyl-3-(naphthalene-2-carbonyl)-1,1-dioxo-2H-benzo[e][1,2]thiazin-4-yl ester;
(4-[2-(naphthalen-1-yloxy)ethoxy]-2-methyl-1,1-dioxo-2H-benzo[e][1,2]thiazin-3-yl)(p-tolyl)methanone;
(4-[2-(4-chlorophenyloxyl)ethoxy]-2-methyl-1,1-dioxo-2H-benzo[e][1,2]thiazin-3-yl)(p-tolyl)methanone;

Acetic acid 2-methyl-3-(4-methylbenzoyl)-1,1-dioxo-2H-benzo[e][1,2]thiazin-4-yl ester;
Propanoic acid 2-methyl-3-(4-methylbenzoyl)-1,1-dioxo-2H-benzo[e][1,2]thiazin-4-yl ester;
(4-methyloxy-2-methyl-1,1-dioxo-2H-benzo[e][1,2]thiazin-3-yl)(p-tolyl)methanone;
(4-ethyloxy-2-methyl-1,1-dioxo-2H-benzo[e][1,2]thiazin-3-yl)(p-tolyl)methanone;
[4-(2-Bromo-ethoxy)-2-methyl-1,1-dioxo-2H-benzo[e][1,2]thiazin-3-yl]-naphthalen-2-yl-methanone;
{4-[2-(4-Chloro-phenoxy)-ethoxy]-2-methyl-1,1-dioxo-2H-benzo[e][1,2]thiazin-3-yl}-naphthalen-2-yl-methanone;
Carbonic acid ethyl ester 1-[2-methyl-3-(naphthalene-2-carbonyl)-1,1-dioxo-2H-benzo[e][1,2]thiazin-4-yloxy]-ethyl ester;
[2-Methyl-4-(2-piperidin-1-yl-ethoxy)-1,1-dioxo-2H-benzo[e][1,2]thiazin-3-yl]-naphthalen-2-yl-methanone;
4-Chloro-benzoic acid 5-chloro-2-methyl-3-(naphthalene-2-carbonyl)-1,1-dioxo-2H-benzo[e][1,2]thiazin-4-yl ester;
Cyclohexanecarboxylic acid 5-chloro-2-methyl-3-(naphthalene-2-carbonyl)-1,1-dioxo-2H-benzo[e][1,2]thiazin-4-yl ester;
Benzoic acid 5-chloro-2-methyl-3-(naphthalene-2-carbonyl)-1,1-dioxo-2H-benzo[e][1,2]thiazin-4-yl ester;
4-Chloro-benzoic acid 6-fluoro-2-methyl-3-(naphthalene-2-carbonyl)-1,1-dioxo-2H-benzo[e][1,2]thiazin-4-yl ester;
Cyclohexanecarboxylic acid 6-fluoro-2-methyl-3-(naphthalene-2-carbonyl)-1,1-dioxo-2H-benzo[e][1,2]thiazin-4-yl ester;
Benzoic acid 6-fluoro-2-methyl-3-(naphthalene-2-carbonyl)-1,1-dioxo-2H-benzo[e][1,2]thiazin-4-yl ester;
4-Chloro-benzoic acid 7-fluoro-2-methyl-3-(naphthalene-2-carbonyl)-1,1-dioxo-2H-benzo[e][1,2]thiazin-4-yl ester;
Cyclohexanecarboxylic acid 7-fluoro-2-methyl-3-(naphthalene-2-carbonyl)-1,1-dioxo-2H-benzo[e][1,2]thiazin-4-yl ester;
Benzoic acid 7-fluoro-2-methyl-3-(naphthalene-2-carbonyl)-1,1-dioxo-2H-benzo[e][1,2]thiazin-4-yl ester;
Acetic acid 7-fluoro-2-methyl-3-(naphthalene-2-carbonyl)-1,1-dioxo-2H-benzo[e][1,2]thiazin-4-yl ester;
Phenoxy-acetic acid 7-fluoro-2-methyl-3-(naphthalene-2-carbonyl)-1,1-dioxo-2H-benzo[e][1,2]thiazin-4-yl ester;
(4-Chloro-phenoxy)-acetic acid 7-fluoro-2-methyl-3-(naphthalene-2-carbonyl)-1,1-dioxo-2H-benzo[e][1,2]thiazin-4-yl ester;
(5-Chloro-4-ethoxy-2-methyl-1,1-dioxo-2H-benzo[e][1,2]thiazin-3-yl)-naphthalen-2-yl-methanone;
(5-Chloro-4-propoxy-2-methyl-1,1-dioxo-2H-benzo[e][1,2]thiazin-3-yl)-naphthalen-2-yl-methanone;
(6-Fluoro-4-methoxy-2-methyl-1,1-dioxo-2H-benzo[e][1,2]thiazin-3-yl)-naphthalen-2-yl-methanone;
(6-Fluoro-4-ethoxy-2-methyl-1,1-dioxo-2H-benzo[e][1,2]thiazin-3-yl)-naphthalen-2-yl-methanone;
(6-Fluoro-4-propoxy-2-methyl-1,1-dioxo-2H-benzo[e][1,2]thiazin-3-yl)-naphthalen-2-yl-methanone;
(7-Fluoro-4-methoxy-2-methyl-1,1-dioxo-2H-benzo[e][1,2]thiazin-3-yl)-naphthalen-2-yl-methanone;
(7-Fluoro-4-ethoxy-2-methyl-1,1-dioxo-2H-benzo[e][1,2]thiazin-3-yl)-naphthalen-2-yl-methanone;
(7-Fluoro-4-propoxy-2-methyl-1,1-dioxo-2H-benzo[e][1,2]thiazin-3-yl)-naphthalen-2-yl-methanone;
[7-Fluoro-2-methyl-3-(naphthalene-2-carbonyl)-1,1-dioxo-2H-benzo[e][1,2]thiazin-4-yloxy]-acetic acid methyl ester;
[7-Fluoro-2-methyl-3-(naphthalene-2-carbonyl)-1,1-dioxo-2H-benzo[e][1,2]thiazin-4-yloxy]-acetic acid methyl ester;
2-[7-Fluoro-2-methyl-3-(naphthalene-2-carbonyl)-1,1-dioxo-2H-benzo[e][1,2]thiazin-4-yloxy]-1-piperidin-1-yl-ethanone;
2-[7-Fluoro-2-methyl-3-(naphthalene-2-carbonyl)-1,1-dioxo-2H-benzo[e][1,2]thiazin-4-yloxy]-1-(4-methyl-piperazin-1-yl)-ethanone;
1-(4-Benzyl-piperazin-1-yl)-2-[7-fluoro-2-methyl-3-(naphthalene-2-carbonyl)-1,1-dioxo-2H-benzo[e][1,2]thiazin-4-yloxy]-ethanone;
Benzenesulfonic acid 7-fluoro-2-methyl-3-(naphthalene-2-carbonyl)-1,1-dioxo-2H-benzo[e][1,2]thiazin-4-yl ester;
Benzenesulfonic acid 2-methyl-3-(naphthalene-2-carbonyl)-1,1-dioxo-2H-benzo[e][1,2]thiazin-4-yl ester;
4-Chloro-benzenesulfonic acid 2-methyl-3-(naphthalene-2-carbonyl)-1,1-dioxo-2H-benzo[e][1,2]thiazin-4-yl ester;
4-Methyl-benzenesulfonic acid 2-methyl-3-(naphthalene-2-carbonyl)-1,1-dioxo-2H-benzo[e][1,2]thiazin-4-yl ester;
4-Cyano-benzenesulfonic acid 2-methyl-3-(naphthalene-2-carbonyl)-1,1-dioxo-2H-benzo[e][1,2]thiazin-4-yl ester;
4-Chloro-benzenesulfonic acid 7-fluoro-2-methyl-3-(naphthalene-2-carbonyl)-1,1-dioxo-2H-benzo[e][1,2]thiazin-4-yl ester;
4-Methyl-benzenesulfonic acid 7-fluoro-2-methyl-3-(naphthalene-2-carbonyl)-1,1-dioxo-2H-benzo[e][1,2]thiazin-4-yl ester;
4-Cyano-benzenesulfonic acid 7-fluoro-2-methyl-3-(naphthalene-2-carbonyl)-1,1-dioxo-2H-benzo[e][1,2]thiazin-4-yl ester;
(4-Hydroxy-2-methyl-1,1-dioxo-7-piperidin-1-yl-2H-benzo[e][1,2]thiazin-3-yl)-naphthalen-2-yl-methanone;
(7-Dimethylamino-4-hydroxy-2-methyl-1,1-dioxo-2H-benzo[e][1,2]thiazin-3-yl)-naphthalen-2-yl-methanone;
(4-Hydroxy-2-methyl-1,1-dioxo-7-pyrrolidin-1-yl-2H-benzo[e][1,2]thiazin-3-yl)-naphthalen-2-yl-methanone;
[4-Hydroxy-2-methyl-1,1-dioxo-7-(4-phenyl-piperazin-1-yl)-2H-benzo[e][1,2]thiazin-3-yl]-naphthalen-2-yl-methanone;
(7-tertbutyl-4-hydroxy-2-methyl-1,1-dioxo-2H-benzo[e][1,2]thiazin-3-yl)(naphthalen-2-yl) methanone;
(4-hydroxy-2-methyl-1,1-dioxo-2H-benzo[e][1,2]thiazin-3-yl)(3,4-dichlorophenyl)methanone;
(4-Hydroxy-2-ethyl-1,1-dioxo-2H-benzo[e][1,2]thiazin-3-yl)(3,4-dichlorophenyl)methanone;
(4-Hydroxy-2-methyl-1,1-dioxo-2H-benzo[e][1,2]thiazin-3-yl)(benzofuran-2-yl)methanone;
(4-Hydroxy-2-ethyl-1,1-dioxo-2H-benzo[e][1,2]thiazin-3-yl)(benzofuran-2-yl)methanone;
(4-Hydroxy-2-methyl-1,1-dioxo-2H-benzo[e][1,2]thiazin-3-yl)-(5,6,7,8-tetrahydro-naphthalen-2-yl)-methanone;
(4-Hydroxy-2-methyl-1,1-dioxo-2H-benzo[e][1,2]thiazin-3-yl)-(5,5,8,8-tetramethyl-5,6,7,8-tetrahydro-naphthalen-2-yl)-methanone;

(7-Fluoro-4-hydroxy-2-methyl-1,1-dioxo-2H-benzo[e][1,2]thiazin-3-yl)-(5,6,7,8-tetrahydro-naphthalen-2-yl)-methanone;
(7-Fluoro-4-hydroxy-2-methyl-1,1-dioxo-2H-benzo[e][1,2]thiazin-3-yl)-(5,5,8,8-tetramethyl-5,6,7,8-tetrahydro-naphthalen-2-yl)-methanone;
(2,3-Dihydro-benzofuran-5-yl)-(4-hydroxy-2-methyl-1,1-dioxo-1,2-dihydro-2H-benzo[e][1,2]thiazin-3-yl)-methanone;
(2,3-Dihydro-benzofuran-5-yl)-(4-hydroxy-2-ethyl-1,1-dioxo-1,2-dihydro-2H-benzo[e][1,2]thiazin-3-yl)-methanone;
Benzo[1,3]dioxol-5-yl-(4-hydroxy-2-methyl-1,1-dioxo-1,2-dihydro-2H-benzo[e][1,2]thiazin-3-yl)-methanone;
Benzo[1,3]dioxol-5-yl-(4-hydroxy-2-ethyl-1,1-dioxo-1,2-dihydro-2H-benzo[e][1,2]thiazin-3-yl)-methanone;
(2,3-Dihydro-benzo[1,4]dioxin-6-yl)-(4-hydroxy-2-methyl-1,1-dioxo-1,2-dihydro-2H-benzo[e][1,2]thiazin-3-yl)-methanone;
(2,3-Dihydro-benzo[1,4]dioxin-6-yl)-(4-hydroxy-2-ethyl-1,1-dioxo-1,2-dihydro-2H-benzo[e][1,2]thiazin-3-yl)-methanone;
Benzo[b]thiophen-5-yl-(4-hydroxy-2-methyl-1,1-dioxo-1,2-dihydro-2H-benzo[e][1,2]thiazin-3-yl)-methanone;
Benzofuran-5-yl-(4-hydroxy-2-methyl-1,1-dioxo-1,2-dihydro-2H-benzo[e][1,2]thiazin-3-yl)-methanone;
(4-Hydroxy-2-methyl-1,1-dioxo-1,2-dihydro-2H-benzo[e][1,2]thiazin-3-yl)-(1-methyl-1H-benzoimidazol-5-yl)-methanone;
Benzo[b]thiophen-2-yl-(4-hydroxy-2-methyl-1,1-dioxo-1,2-dihydro-2H-benzo[e][1,2]thiazin-3-yl)-methanone;
(4-tert-Butyl-phenyl)-(4-hydroxy-2-methyl-1,1-dioxo-1,2-dihydro-2H-benzo[e][1,2]thiazin-3-yl)-methanone;
(3-Bromo-phenyl)-(4-hydroxy-2-methyl-1,1-dioxo-1,2-dihydro-2H-benzo[e][1,2]thiazin-3-yl)-methanone;
3-(4-Hydroxy-2-methyl-1,1-dioxo-1,2-dihydro-2H-benzo[e][1,2]thiazine-3-carbonyl)-benzonitrile;
(3,4-Dimethyl-phenyl)-(4-hydroxy-2-methyl-1,1-dioxo-1,2-dihydro-2H-benzo[e][1,2]thiazin-3-yl)-methanone;
(4-Hydroxy-2-methyl-1,1-dioxo-1,2-dihydro-2H-benzo[e][1,2]thiazin-3-yl)-(3-trifluoromethyl-phenyl)-methanone;
(4-Hydroxy-2-methyl-1,1-dioxo-1,2-dihydro-2H-benzo[e][1,2]thiazin-3-yl)-(4-trifluoromethyl-phenyl)-methanone;
Adamantan-2-yl-(4-hydroxy-2-methyl-1,1-dioxo-1,2-dihydro-2H-benzo[e][1,2]thiazin-3-yl)-methanone;
Chroman-6-yl-(4-hydroxy-2-methyl-1,1-dioxo-1,2-dihydro-2H-benzo[e][1,2]thiazin-3-yl)-methanone;
(4-Chloro-3-trifluoromethyl-phenyl)-(4-hydroxy-2-methyl-1,1-dioxo-1,2-dihydro-2H-benzo[e][1,2]thiazin-3-yl)-methanone;
(7-Bromo-4-hydroxy-2-methyl-1,1-dioxo-1,2-dihydro-2H-benzo[e][1,2]thiazin-3-yl)-naphthalen-2-yl-methanone;
(7-Chloro-4-hydroxy-2-methyl-1,1-dioxo-1,2-dihydro-2H-benzo[e][1,2]thiazin-3-yl)-naphthalen-2-yl-methanone;
(4-Hydroxy-2,7-dimethyl-1,1-dioxo-1,2-dihydro-2H-benzo[e][1,2]thiazin-3-yl)-naphthalen-2-yl-methanone;
Biphenyl-3-yl-(4-hydroxy-2-methyl-1,1-dioxo-1,2-dihydro-2H-benzo[e][1,2]thiazin-3-yl)-methanone;
(2'-Fluoro-biphenyl-3-yl)-(4-hydroxy-2-methyl-1,1-dioxo-1,2-dihydro-2H-benzo[e][1,2]thiazin-3-yl)-methanone;
(3'-Fluoro-biphenyl-3-yl)-(4-hydroxy-2-methyl-1,1-dioxo-1,2-dihydro-2H-benzo[e][1,2]thiazin-3-yl)-methanone;
(4'-Fluoro-biphenyl-3-yl)-(4-hydroxy-2-methyl-1,1-dioxo-1,2-dihydro-2H-benzo[e][1,2]thiazin-3-yl)-methanone;
(2'-Chloro-biphenyl-3-yl)-(4-hydroxy-2-methyl-1,1-dioxo-1,2-dihydro-2H-benzo[e][1,2]thiazin-3-yl)-methanone;
(3'-Chloro-biphenyl-3-yl)-(4-hydroxy-2-methyl-1,1-dioxo-1,2-dihydro-2H-benzo[e][1,2]thiazin-3-yl)-methanone;
(4'-Chloro-biphenyl-3-yl)-(4-hydroxy-2-methyl-1,1-dioxo-1,2-dihydro-2H-benzo[e][1,2]thiazin-3-yl)-methanone;
(2'-Methyl-biphenyl-3-yl)-(4-hydroxy-2-methyl-1,1-dioxo-1,2-dihydro-2H-benzo[e][1,2]thiazin-3-yl)-methanone;
(3'-Methyl-biphenyl-3-yl)-(4-hydroxy-2-methyl-1,1-dioxo-1,2-dihydro-2H-benzo[e][1,2]thiazin-3-yl)-methanone;
(4'-Methyl-biphenyl-3-yl)-(4-hydroxy-2-methyl-1,1-dioxo-1,2-dihydro-2H-benzo[e][1,2]thiazin-3-yl)-methanone;
(2'-Methoxy-biphenyl-3-yl)-(4-hydroxy-2-methyl-1,1-dioxo-1,2-dihydro-2H-benzo[e][1,2]thiazin-3-yl)-methanone;
(3'-Methoxy-biphenyl-3-yl)-(4-hydroxy-2-methyl-1,1-dioxo-1,2-dihydro-2H-benzo[e][1,2]thiazin-3-yl)-methanone;
(4'-Methoxy-biphenyl-3-yl)-(4-hydroxy-2-methyl-1,1-dioxo-1,2-dihydro-2H-benzo[e][1,2]thiazin-3-yl)-methanone;
(4-Hydroxy-2-methyl-1,1-dioxo-1,2-dihydro-2H-benzo[e][1,2]thiazin-3-yl)-(3'-trifluoromethyl-biphenyl-3-yl)-methanone;
(4-Hydroxy-2-methyl-1,1-dioxo-1,2-dihydro-2H-benzo[e][1,2]thiazin-3-yl)-(4'-trifluoromethyl-biphenyl-3-yl)-methanone;
3'-(4-Hydroxy-2-methyl-1,1-dioxo-1,2-dihydro-2H-benzo[e][1,2]thiazine-3-carbonyl)-biphenyl-3-carbonitrile;
3'-(4-Hydroxy-2-methyl-1,1-dioxo-1,2-dihydro-2H-benzo[e][1,2]thiazine-3-carbonyl)-biphenyl-4-carbonitrile;
(4-Hydroxy-7-methanesulfonyl-2-methyl-1,1-dioxo-1,2-dihydro-2H-benzo[e][1,2]thiazin-3-yl)-naphthalen-2-yl-methanone;
(4-Hydroxy-2-methyl-1,1-dioxo-1,2-dihydro-2H-benzo[e][1,2]thiazin-3-yl)-(1-phenyl-cyclopropyl)-methanone;
1-[3-(4-Hydroxy-2-methyl-1,1-dioxo-1,2-dihydro-2H-benzo[e][1,2]thiazine-3-carbonyl)-phenyl]-ethanone;
(4-Hydroxy-2-methyl-1,1-dioxo-1,2-dihydro-2H-benzo[e][1,2]thiazin-3-yl)-[3-(2,2,2-trifluoro-1-hydroxy-1-methyl-ethyl)-phenyl]-methanone;
(4-Hydroxy-2-methyl-1,1-dioxo-1,2-dihydro-2H-benzo[e][1,2]thiazin-3-yl)-[3-(2,2,2-trifluoro-1-hydroxy-ethyl)-phenyl]-methanone;
3-(4-Hydroxy-2-methyl-1,1-dioxo-1,2-dihydro-2H-benzo[e][1,2]thiazine-3-carbonyl)-benzoic acid;
3-(4-Hydroxy-2-methyl-1,1-dioxo-1,2-dihydro-2H-benzo[e][1,2]thiazine-3-carbonyl)-N-methyl-benzamide;
3-(4-Hydroxy-2-methyl-1,1-dioxo-1,2-dihydro-2H-benzo[e][1,2]thiazine-3-carbonyl)-N,N-dimethyl-benzamide;

N-Ethyl-3-(4-hydroxy-2-methyl-1,1-dioxo-1,2-dihydro-2H-benzo[e][1,2]thiazine-3-carbonyl)-benzamide;
3-(4-Hydroxy-2-methyl-1,1-dioxo-1,2-dihydro-2H-benzo[e][1,2]thiazine-3-carbonyl)-N,N-diethyl-benzamide;
N-Cyclopropyl-3-(4-hydroxy-2-methyl-1,1-dioxo-1,2-dihydro-2H-benzo[e][1,2]thiazine-3-carbonyl)-benzamide;
N-Cyclopropylmethyl-3-(4-hydroxy-2-methyl-1,1-dioxo-1,2-dihydro-2H-benzo[e][1,2]thiazine-3-carbonyl)-benzamide;
3-(4-Hydroxy-2-methyl-1,1-dioxo-1,2-dihydro-2H-benzo[e][1,2]thiazine-3-carbonyl)-N-phenyl-benzamide;
N-Benzyl-3-(4-hydroxy-2-methyl-1,1-dioxo-1,2-dihydro-2H-benzo[e][1,2]thiazine-3-carbonyl)-benzamide;
3-(4-Hydroxy-2-methyl-1,1-dioxo-1,2-dihydro-2H-benzo[e][1,2]thiazine-3-carbonyl)-benzamide;
3-(4-Hydroxy-2-methyl-1,1-dioxo-1,2-dihydro-2H-benzo[e][1,2]thiazine-3-carbonyl)-benzoic acid ethyl ester;
(4-Hydroxy-2-methyl-1,1-dioxo-1,2-dihydro-2H-benzo[e][1,2]thiazin-3-yl)-(3-pyridin-3-yl-phenyl)-methanone;
(4-Hydroxy-2-methyl-1,1-dioxo-1,2-dihydro-2H-benzo[e][1,2]thiazin-3-yl)-(3-pyridin-4-yl-phenyl)-methanone;
(4-Hydroxy-2-methyl-1,1-dioxo-1,2-dihydro-2H-benzo[e][1,2]thiazin-3-yl)-[3-(6-methyl-pyridin-3-yl)-phenyl]-methanone;
(4-Hydroxy-2-methyl-1,1-dioxo-1,2-dihydro-2H-benzo[e][1,2]thiazin-3-yl)-[3-(5-methyl-pyridin-3-yl)-phenyl]-methanone;
(4-Hydroxy-2-methyl-1,1-dioxo-1,2-dihydro-2H-benzo[e][1,2]thiazin-3-yl)-[3-(4-methyl-pyridin-3-yl)-phenyl]-methanone;
(4-Hydroxy-2-methyl-1,1-dioxo-1,2-dihydro-2H-benzo[e][1,2]thiazin-3-yl)-[3-(2-methyl-pyridin-3-yl)-phenyl]-methanone;
(4-Hydroxy-2-methyl-1,1-dioxo-1,2-dihydro-2H-benzo[e][1,2]thiazin-3-yl)-[3-(4-methoxy-pyridin-3-yl)-phenyl]-methanone;
(4-Hydroxy-2-methyl-1,1-dioxo-1,2-dihydro-2H-benzo[e][1,2]thiazin-3-yl)-[3-(6-fluoro-pyridin-3-yl)-phenyl]-methanone;
(4-Hydroxy-2-methyl-1,1-dioxo-1,2-dihydro-2H-benzo[e][1,2]thiazin-3-yl)-[3-(2-methoxy-pyridin-3-yl)-phenyl]-methanone;
(4-Hydroxy-2-methyl-1,1-dioxo-1,2-dihydro-2H-benzo[e][1,2]thiazin-3-yl)-[3-(6-methoxy-pyridin-3-yl)-phenyl]-methanone;
(3-Chloro-phenyl)-(4-hydroxy-2-methyl-1,1-dioxo-1,2-dihydro-2H-benzo[e][1,2]thiazin-3-yl)-methanone; and
(3-Fluoro-phenyl)-(4-hydroxy-2-methyl-1,1-dioxo-1,2-dihydro-2H-benzo[e][1,2]thiazin-3-yl)-methanone.

7. A method for preparing the compounds of general formula (Ia) which corresponds to formula I according to claim 1 wherein $R_1$ represents a hydrogen atom characterized in that an intermediate of general formula (IV) is condensed

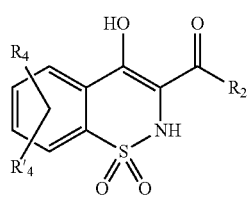

wherein $R_2$, $R_4$, and $R'_4$ are defined according to claim 1, with an intermediate of general formula $R_3$—Y wherein $R_3$ is defined according to claim 1 and Y represents a leaving group.

8. A method for preparing the compounds of general formula (Ib) which corresponds to formula I according to claim 1, wherein $R_1$ is different from a hydrogen atom characterized in that an intermediate of general formula (Ia) is condensed

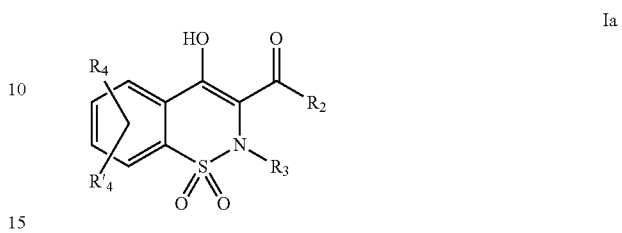

wherein $R_2$, $R_3$, $R_4$, and $R'_4$ are defined according to claim 1, with an intermediate of general formula $R_1$—Z wherein $R_1$ is defined as earlier and Z represents a leaving group.

9. A method for preparing the compounds of general formula (Ic) which corresponds to formula I according to claim 1 wherein $R_1$ represents $(CH_2)_n NR_7R_8$ or $(CH_2)_n OR_6$ characterized in that an intermediate of general formula (V) is condensed

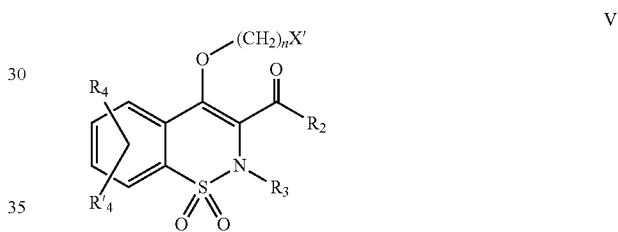

wherein $R_2$, $R_3$, $R_4$, $R'_4$, and n are defined according to claim 1 and X' represents a leaving group, with an intermediate of general formula $R_7R_8NH$ or $R_6OH$ wherein $R_7$, $R_8$, and $R_6$ are defined according to claim 1.

10. A method for preparing the compounds of general formula (Id) which corresponds to formula I according to claim 1 wherein $R_1$ represents $(CH_2)_n CONR_7R_8$ characterized in that an intermediate of general formula (VII) is condensed

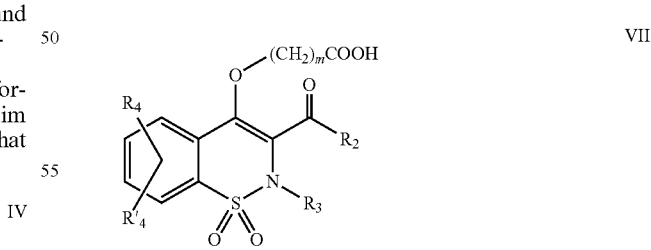

wherein $R_2$, $R_3$, $R_4$, $R'_4$ and m are defined according to claim 1, with an intermediate of general formula $R_7R_8NH$ wherein $R_7$ and $R_8$ are defined according to claim 1.

11. A method for preparing the compounds of general formula (If) which corresponds to formula I according to claim 1 wherein $R_4$ represents $NR_7R_8$ characterized in that an intermediate of general formula (Ie) is condensed

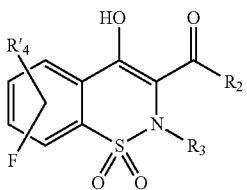

wherein $R_2$, $R_3$, and $R'_4$ are defined according to claim 1, with an intermediate of general formula $R_7R_8NH$ wherein $R_7$ and $R_8$ are defined according to claim 1.

12. A method for preparing the compounds of general formula (Ih) which corresponds to formula I according to claim 1 wherein $R_2$ represents a biphenyl or phenyl pyridine either substituted or not, characterized in that an intermediate of general formula (Ig) is condensed

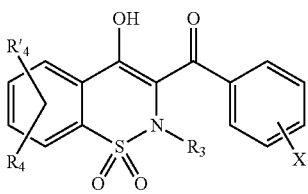

wherein $R_3$, $R_4$, and $R'_4$ are defined according to claim 1 and X represents a leaving group, with a boronic acid.

13. A method for preparing the compounds of general formula (Ik) which corresponds to formula I according to claim 1 wherein $R_2$ represents a phenyl substituted with an amide in the ortho or meta position characterized in that an intermediate of general formula (Ij) is condensed

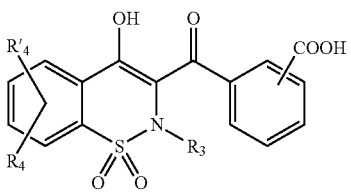

wherein $R_3$, $R_4$, and $R'_4$ are defined according to claim 1, with an amine of general formula $R_7R_{11}NH$ wherein $R_7$ and $R_{11}$ are defined according to claim 1.

14. Pharmaceutical compositions containing as an active ingredient at least one compound according to claim 1, in combination with a pharmaceutically acceptable carrier.

15. A method of inhibiting type 1 11β-hydroxysteroid dehydrogenase (11βHSD1) comprising administering a therapeutically effective amount of the pharmaceutical composition of claim 14, to a patient in need thereof.

16. A method of treating diabetes of type 2 comprising administering a therapeutically effective amount of the pharmaceutical composition of claim 14, to a patient in need thereof.

17. A method of treating disorders related to type 1 11β-hydroxysteroid dehydrogenase (11βHSD1); or of obesity; or dyslipidemias, comprising administering a therapeutically effective amount of the pharmaceutical composition of claim 14, to a patient in need thereof.

18. A method according to claim 16, wherein the administration is made in association with an anti-diabetic agent.

19. A method according to claim 16, wherein the administration is made in association with an anti-obesity agent.

20. The method of claim 18, wherein said anti-diabetic agent is selected among biguanides, various forms of insulin, sulfonylureas, meglitinides, PPAR modulators, alpha-glucosidase inhibitors, GLP-1 analogs, DPP-4 inhibitors or amyline analogs.

21. The method of claim 19, wherein said anti-obesity agent is orlistat or sibutramine.

22. Compounds fitting general formula (I):

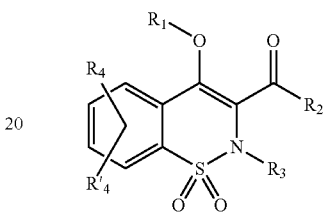

wherein:
$R_1$ represents: $C_1$-$C_6$ alkyl; $COR_5$; $CO(CH_2)_mR_6$; $(CH_2)_mR_6$; or $(CH_2)_mR_{10}$,
m represents: 1 to 6,
n represents: 2 to 6,
$R_2$ represents: phenyl substituted with one or more groups selected from a halogen, $C_1$-$C_6$ alkyl, CN, OH, $CF_3$, $OCF_3$, SMe, COMe, $CMe(OH)CF_3$, $CH(OH)CF_3$, $COOR_7$, $CONR_7R_{11}$; a naphthyl, 1,2,3,4-tetrahydronaphthalene, biphenyl, phenyl pyridine or pyridine in the case where $R_1$, $R_4$ and $R'_4$ represent a hydrogen, either non-substituted or substituted with one or more groups selected from a halogen, $C_1$-$C_6$ alkyl, CN, OH, $CF_3$, $OCF_3$, OMe, SMe; a cycloalkyl either non-substituted or substituted with OH, $CONH_2$, $SO_2Me$, $SO_2NH_2$; $C_1$-$C_6$ alkyl aryl or cycloalkyl aryl, wherein $R_2$ is always bound to the carbonyl through a carbon atom and if $R_2$ is phenyl substituted with $COOR_7$, $COOR_7$ is not in position 4 relative to the carbonyl bonded to $R_2$,
$R_3$ represents: methyl or ethyl,
$R_4$ and $R'_4$, either identical or different, represent: hydrogen; halogen; $C_1$-$C_6$ alkyl; CN; $CF_3$; $OCF_3$; SMe; OMe; $NR_7R_8$; $SO_2Me$,
$R_5$ represents: $C_1$-$C_6$ alkyl; phenyl either non-substituted or substituted with one or more groups selected from halogen, $C_1$-$C_6$ alkyl, CN, OH, $CF_3$, $OCF_3$, SMe; a naphthyl, either non-substituted or substituted with one or more groups selected from halogen or $C_1$-$C_6$ alkyl, CN, OH, $CF_3$, $OCF_3$, SMe; a cycloalkyl either non-substituted or substituted with a $CONH_2$, $SO_2Me$, $SO_2NH_2$, heteroaryl either non-substituted or substituted with one or more groups selected from halogen, $C_1$-$C_6$ alkyl, CN, OH, $CF_3$, $OCF_3$, SMe,
$R_6$ represents: hydrogen; $C_1$-$C_6$ alkyl; phenyl either non-substituted or substituted with one or more groups selected from halogen, $C_1$-$C_6$ alkyl, CN, OH, $CF_3$, $OCF_3$, SMe; a naphthyl or heterocycle, either non-substituted or substituted with one or more groups selected from halogen or $C_1$-$C_6$ alkyl, CN, OH, $CF_3$, $OCF_3$, SMe; a cycloalkyl either non-substituted or substituted with $CONH_2$, $SO_2Me$, $SO_2NH_2$, $R_7$ represents: hydrogen, $C_1$-$C_6$ alkyl, $R_8$ represents: hydrogen, $C_1$-$C_6$ alkyl, phenyl either non-substituted or substituted with one or more groups selected from halogen, $C_1$-$C_6$ alkyl, CN, OH, $CF_3$, $OCF_3$, SMe; a naphthyl or heterocycle, either non-substituted or substituted with one or more groups selected from halogen, $C_1$-$C_6$ alkyl, CN, OH, $CF_3$, $OCF_3$, SMe; a cycloalkyl either non-substituted or substituted with $CONH_2$, $SO_2Me$, $SO_2NH_2$, $R_7$ and $R_8$ taken together may form a cycle of 4 to 6 members with the nitrogen atom to which they are bound and which may contain one or more heteroatoms selected from N, S or O and may either be non-substituted or substituted with one or more groups selected from $C_1$-$C_6$ alkyl, $C_1$-$C_6$ alkyl aryl or aryl, $R_9$ represents: COOMe, COOEt, $R_{10}$ represents: halogen, COOH, $COOR_7$, and $R_{11}$ represents: hydrogen, $C_1$-$C_6$ alkyl, $C_1$-$C_6$ alkyl cycloalkyl, cycloalkyl, aryl, $C_1$-$C_6$ alkyl aryl, as well as stereoisomers and salts thereof acceptable for therapeutic use.

23. Compounds fitting general formula (I):

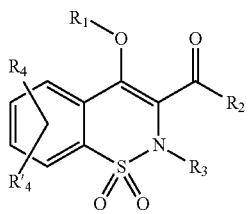

I wherein:

$R_1$ represents: hydrogen; $C_1$-$C_6$ alkyl; $COR_5$; $SO_2R_5$; $CO(CH_2)_mR_6$; $CO(CH_2)_mOR_6$; $(CH_2)_mR_6$; $(CH_2)_m$$CONR_7R_8$; $(CH_2)_nNR_7R_8$; $(CH_2)_nOR_6$; $CHR_7OR_9$; or $(CH_2)_mR_{10}$, m represents: 1 to 6, n represents: 2 to 6, $R_2$ represents: a naphthyl or a 1,2,3,4-tetrahydro-naphthalene or a biphenyl or a phenyl pyridine either non-substituted or substituted with one or more groups selected from a halogen, $C_1$-$C_6$ alkyl, CN, OH, $CF_3$, $OCF_3$, OMe, SMe; or a phenyl substituted with one or more halogens, CN, $CF_3$ or $C_1$-$C_6$ alkyl, $R_3$ represents: methyl or ethyl, $R_4$ and $R'_4$, either identical or different, represent: hydrogen; halogen; $C_1$-$C_6$ alkyl; CN; $CF_3$; $OCF_3$; SMe; OMe; $NR_7R_8$; $SO_2Me$, $R_5$ represents: $C_1$-$C_6$ alkyl; phenyl either non-substituted or substituted with one or more groups selected from halogen, $C_1$-$C_6$ alkyl, CN, OH, $CF_3$, $OCF_3$, SMe; a naphthyl, either non-substituted or substituted with one or more groups selected from halogen or $C_1$-$C_6$ alkyl, CN, OH, $CF_3$, $OCF_3$, SMe; a cycloalkyl either non-substituted or substituted with a $CONH_2$, $SO_2Me$, $SO_2NH_2$, heteroaryl either non-substituted or substituted with one or more groups selected from halogen, $C_1$-$C_6$ alkyl, CN, OH, $CF_3$, $OCF_3$, SMe, $R_6$ represents: hydrogen; $C_1$-$C_6$ alkyl; phenyl either non-substituted or substituted with one or more groups selected from halogen, $C_1$-$C_6$ alkyl, CN, OH, $CF_3$, $OCF_3$, SMe; a naphthyl or heterocycle, either non-substituted or substituted with one or more groups selected from halogen or $C_1$-$C_6$ alkyl, CN, OH, $CF_3$, $OCF_3$, SMe; a cycloalkyl either non-substituted or substituted with $CONH_2$, $SO_2Me$, $SO_2NH_2$, $R_7$ represents: hydrogen, $C_1$-$C_6$ alkyl, $R_8$ represents: hydrogen, $C_1$-$C_6$ alkyl, phenyl either non-substituted or substituted with one or more groups selected from halogen, $C_1$-$C_6$ alkyl, CN, OH, $CF_3$, $OCF_3$, SMe; a naphthyl or heterocycle, either non-substituted or substituted with one or more groups selected from halogen, $C_1$-$C_6$ alkyl, CN, OH, $CF_3$, $OCF_3$, SMe; a cycloalkyl either non-substituted or substituted with $CONH_2$, $SO_2Me$, $SO_2NH_2$, $R_7$ and $R_8$ taken together may form a cycle of 4 to 6 members with the nitrogen atom to which they are bound and which may contain one or more heteroatoms selected from N, S or O and may either be non-substituted or substituted with one or more groups selected from $C_1$-$C_6$ alkyl, $C_1$-$C_6$ alkyl aryl or aryl, $R_9$ represents: COOMe, COOEt, $R_{10}$ represents: halogen, COOH, $COOR_7$, and $R_{11}$ represents: hydrogen, $C_1$-$C_6$ alkyl, $C_1$-$C_6$ alkyl cycloalkyl, cycloalkyl, aryl, $C_1$-$C_6$ alkyl aryl, as well as stereoisomers and salts thereof acceptable for therapeutic use.

24. The method according to claim 17 wherein the disorders are hyperglycemias; or intolerance to glucose; or insulin-resistance; or hypertriglyceridemias; or hypercholesterolemias.

* * * * *